US012571017B2

(12) United States Patent (10) Patent No.: US 12,571,017 B2
Chiocchini et al. (45) Date of Patent: Mar. 10, 2026

(54) DEVICES AND METHODS FOR PRODUCING NUCLEIC ACIDS AND PROTEINS

(71) Applicants: THERMO FISHER SCIENTIFIC GENEART GMBH, Regensburg (DE); PIERCE BIOTECHNOLOGY, INC., Rockford, IL (US)

(72) Inventors: Claudia Chiocchini, Regensburg (DE); Axel Trefzer, Tegernheim (DE); Krishna Vattem, Roscoe, IL (US); Phillip Kuhn, Regensburg (DE)

(73) Assignee: Life Technologies Corporation, Carlsbad, CA (US)

( * ) Notice: Subject to any disclaimer, the term of this patent is extended or adjusted under 35 U.S.C. 154(b) by 1218 days.

(21) Appl. No.: 17/459,053

(22) Filed: Aug. 27, 2021

(65) Prior Publication Data

US 2022/0090161 A1 Mar. 24, 2022

Related U.S. Application Data

(63) Continuation of application No. 15/766,172, filed as application No. PCT/US2016/055292 on Oct. 4, 2016, now abandoned.

(60) Provisional application No. 62/334,304, filed on May 10, 2016, provisional application No. 62/237,764, filed on Oct. 6, 2015.

(51) Int. Cl.

| | |
|---|---|
| *C12P 21/02* | (2006.01) |
| *C12M 1/36* | (2006.01) |
| *C12N 15/10* | (2006.01) |
| *C12N 15/11* | (2006.01) |
| *C12N 15/67* | (2006.01) |
| *C12P 13/00* | (2006.01) |
| *C12P 19/34* | (2006.01) |
| *C12Q 1/6809* | (2018.01) |
| *C40B 50/04* | (2006.01) |

(52) U.S. Cl.
CPC .............. *C12P 21/02* (2013.01); *C12M 1/36* (2013.01); *C12N 15/1096* (2013.01); *C12N 15/11* (2013.01); *C12N 15/67* (2013.01); *C12P 13/005* (2013.01); *C12P 19/34* (2013.01); *C12Q 1/6809* (2013.01); *C40B 50/04* (2013.01)

(58) Field of Classification Search
None
See application file for complete search history.

(56) References Cited

U.S. PATENT DOCUMENTS

| | | | |
|---|---|---|---|
| 4,458,066 | A | 7/1984 | Caruthers et al. |
| 4,652,639 | A | 3/1987 | Stabinsky |
| 5,580,759 | A | 12/1996 | Yang et al. |
| 5,605,793 | A | 2/1997 | Stemmer |
| 5,624,827 | A | 4/1997 | Rosenblum et al. |
| 5,830,721 | A | 11/1998 | Stemmer et al. |
| 5,869,644 | A | 2/1999 | Shortle et al. |
| 6,083,726 | A | 7/2000 | Mills, Jr. et al. |
| 6,110,668 | A | 8/2000 | Strizhov et al. |
| 6,153,410 | A | 11/2000 | Arnold et al. |
| 6,171,820 | B1 | 1/2001 | Short |
| 6,177,263 | B1 | 1/2001 | Arnold et al. |
| 6,472,184 | B1 | 10/2002 | Hegemann |
| 6,495,318 | B2 | 12/2002 | Harney |
| 6,506,603 | B1 | 1/2003 | Stemmer |
| 6,521,427 | B1 | 2/2003 | Evans |
| 6,562,594 | B1 | 5/2003 | Short |
| 6,764,835 | B2 | 7/2004 | Short |
| 7,399,590 | B2 | 7/2008 | Piepenburg et al. |
| 7,666,598 | B2 | 2/2010 | Piepenburg et al. |
| 7,704,690 | B2 | 4/2010 | Young |
| 7,790,418 | B2 | 9/2010 | Mayer |
| 7,820,412 | B2 | 10/2010 | Belshaw et al. |
| 7,833,759 | B2 | 11/2010 | Padgett et al. |
| 7,838,210 | B2 | 11/2010 | Ludwig et al. |
| 7,947,477 | B2 | 5/2011 | Schroeder |
| 7,985,565 | B2 | 7/2011 | Mayer et al. |
| 8,143,008 | B2 | 3/2012 | Kawashima et al. |
| 8,173,368 | B2 | 5/2012 | Staehler et al. |
| 8,224,578 | B2 | 7/2012 | Raab et al. |
| 8,637,253 | B2 | 1/2014 | Piepenburg et al. |
| 8,715,934 | B2 | 5/2014 | Diehl et al. |

(Continued)

FOREIGN PATENT DOCUMENTS

| | | | |
|---|---|---|---|
| WO | WO-2000015777 | A1 | 3/2000 |
| WO | WO-2003106679 | A1 | 12/2003 |

(Continued)

OTHER PUBLICATIONS

Anonymous: "*Orpinomyces* sp. PC-2 1, 4-beta-D-glucan-cellobiohydrolase (celF) mRNA, complete CDS, GenBank U97154. 1", GenBank, Mar. 24, 2003 (Mar. 24, 2003), XP055750088, 2 pages, Retrieved from the Internet: URL: https://www.ncbi.nlm.nih.gov/nuccore/3004639?sat=13&satkey=5356499 [retrieved on Nov. 13, 2020].

(Continued)

*Primary Examiner* — Nancy J Leith

(57) ABSTRACT

The present disclosure generally relates to devices, compositions and methods for designing and producing nucleic acid molecules and the production of encoded proteins using these nucleic acid molecules. In some aspect, the disclosure relates to automation for the in vitro generation of coding DNA molecules, the in vitro transcription of these DNA molecules to generate protein coding RNA molecules, and the in vitro translation of these protein coding RNA molecules to produce proteins.

11 Claims, 36 Drawing Sheets

Specification includes a Sequence Listing.

(56)                     References Cited

U.S. PATENT DOCUMENTS

| | | | |
|---|---|---|---|
| 8,808,989 | B1 | 8/2014 | Efcavitch et al. |
| 8,809,021 | B2 | 8/2014 | Armes et al. |
| 8,895,249 | B2 | 11/2014 | Shen et al. |
| 9,057,097 | B2 | 6/2015 | Piepenburg et al. |
| 9,121,047 | B2 | 9/2015 | Schultz et al. |
| 2003/0152984 | A1 | 8/2003 | Aygun et al. |
| 2006/0115850 | A1 | 6/2006 | Schatz |
| 2006/0127920 | A1 | 6/2006 | Church et al. |
| 2007/0141557 | A1 | 6/2007 | Raab et al. |
| 2007/0231805 | A1 | 10/2007 | Baynes et al. |
| 2007/0292954 | A1 | 12/2007 | Elledge |
| 2008/0145913 | A1 | 6/2008 | Padgett et al. |
| 2009/0275086 | A1 | 11/2009 | Gibson et al. |
| 2009/0317862 | A1 | 12/2009 | Imataka et al. |
| 2010/0062495 | A1 | 3/2010 | Liu et al. |
| 2010/0216648 | A1 | 8/2010 | Staehler et al. |
| 2010/0291633 | A1 | 11/2010 | Selmer et al. |
| 2011/0124049 | A1 | 5/2011 | Li et al. |
| 2012/0053087 | A1 | 3/2012 | Gibson et al. |
| 2012/0156728 | A1 | 6/2012 | Li et al. |
| 2013/0203607 | A1 | 8/2013 | Li et al. |
| 2013/0225421 | A1 | 8/2013 | Li et al. |
| 2013/0338042 | A1 | 12/2013 | Shen et al. |
| 2014/0080717 | A1 | 3/2014 | Li et al. |
| 2014/0155297 | A1 | 6/2014 | Heinz |
| 2016/0186166 | A1 | 6/2016 | Poehmerer et al. |
| 2022/0090161 | A1* | 3/2022 | Chiocchini .......... C12Q 1/6809 |

FOREIGN PATENT DOCUMENTS

| | | | |
|---|---|---|---|
| WO | WO-2006078821 A2 | 7/2006 | |
| WO | WO-2009146892 A1 | 12/2009 | |
| WO | WO-2010040531 A2 | 4/2010 | |
| WO | WO-2010144103 A1 | 12/2010 | |
| WO | WO-2011102802 A1 | 8/2011 | |
| WO | WO-2013158313 A1 | 10/2013 | |
| WO | WO-2014153188 A2 | 9/2014 | |
| WO | WO-2016094512 A1 | 6/2016 | |

OTHER PUBLICATIONS

Bernhard, Frank et al., "Cell-Free Expression—Making a Mark", Current Opinion in Structural Biology vol. 23, 2013, 374-380.

Borovkov et al., "High-quality gene assembly directly from unpurified mixtures of microarray-synthesized oligonucleotides", Nucleic Acids Research, 2010, vol. 38, No. 19, e180, 10 pages.

Brodel, Andreas K. et al., "Cell-Free Protein Expression Based on Extracts From CHO Cells", Biotechnology and Bioengineering vol. 111, No. 1, Jan. 2014, 25-36.

Carlson, Erik D. et al., "Cell-Free Protein Synthesis: Applications Come of Age", Biotechnoloav Advances doi:10.1016/j.biotechadv. 2011.09.016, 2011, 1-10.

Catherine C. et al., "Cell-Free Expression and In Situ Immobilization of Parasite Proteins from Clonorchis sinensis for Rapid Identification of Antigenic Candidates", PLOS ONE, vol. 10, No. 11, Nov. 24, 2015 (Nov. 24, 2015), p. e0143597, XP055750389, DOI: 10.1371/journal.pone.0143597.

Crouzet M. et al., "In vitro translation more efficient with additional tRNA", Trends in Genetics, Elsevier Science, Publishers B.V. Amsterdam, NL, vol. 2, Jan. 1, 1986 (Jan. 1, 1986), p. 226, XP025996703, ISSN: 0168-9525, DOI: 10.1016/0168-9525(86)90240-4 [retrieved on Jan. 1, 1986].

Eckes, Peter et al., "Overproduction of Alfalfa Glutamine Synthetase in Transgenic Tobacco Plants", Mol. Gen. Genet, vol. 217, 1989,263-268.

Elhaik, Eran et al., "GC3 Biology in Eukaryotes and Prokaryotes", DNA Methylation-From Genomics to Technology, Mar. 8, 2012, 55-68.

EP20173826.7, Extended European Search Report, Nov. 27, 2020, 11 pages.

Fath et al., "Multiparameter RNA and Codon Optimization: A Standardized Tool to Assess and Enhance Autologous Mammalian Gene Expression", PLoS One, Mar. 2011, vol. 6, No. 3, e17596, 14 pages.

Fay At, Guy et al., "Effect of the overproduction of phenylalanyl- and threonyl-tRNA synthesis on tRNA Phe and tRNA Thr concentrations in E. coli cells", Biochimie, vol. 65, No. 3, 1983, 221-225.

Frohler, J. et al., "Genetic Analysis of Mutations Causing a Borrelidin Resistance by Overproduction of Threonyi-Transfer Ribonucleic Acid Synthetase", Journal of Bacteriology, vol. 143, No. 3, Sep. 1980, 1135-1141.

Fukuda, Ryuji et al., "Mechanism of the Rifampicin Induction of RNA Polymerase Band B' Subunit Synthesis in Escherichia coli", The Journal of Biological Chemistry, vol. 258, No. 4, Feb. 25, 1983, 2720-2728.

Hitzeman et al., "Expression of a human gene for interferon in yeast", Nature, vol. 293, pp. 717-722 (Year: 1981).

Hughes S R et al., "High-throughput screening of cellulase F mutants from multiplexed plasmid sets using an automated plate assay on a functional proteomic robotic workcell", Proteome Science, Biomed Central, GB, vol. 4, No. 1, May 2, 2006 (May 2, 2006), p. 10, XP021018504, ISSN: 1477-5956, DOI: 10.1186/1477-5956-4-10.

International Search Report and Written Opinion for Application No. PCT/US2016/055292, mailed Feb. 6, 2017, 23 pages.

Korencic, Dragana et al., "A one-step method for in vitro production of tRNA transcripts", Nucleic Acids Research, vol. 30, No. 20, Aug. 15, 2002, 1-4.

Matzas, Mark et al., "High-Fidelity Gene Synthesis by Retrieval of Sequence-Verified DNA Identified Using High-Throughput Pyrosequencing", Nature Biotechnology, vol. 28, No. 12,Dec. 2010, 1291-1294.

Mikami S et al., "A human cell-derived in vitro coupled transcription/ translation system optimized for production of recombinant proteins", Protein Expression and Purification, Academic Press, San Diego, CA, vol. 62, No. 2, Dec. 1, 2008 (Dec. 1, 2008), pp. 190-198, XP025572163, ISSN: 1046-5928, DOI: 10.1016/J.PEP.2008.09.002 [retrieved on Sep. 11, 2008].

Raina, Medha et al., "tRNAs as Regulators of Biological Processes", Frontiers in Genetics, vol. 5,Article 171,Jun. 11, 2014, 1-14.

Rosenblum G et al., "Engine out of the chassis: Cell-free protein synthesis and its uses", FEBS Letters, Elsevier, Amsterdam, NL, vol. 588, No. 2, Oct. 22, 2013 (Oct. 22, 2013), pp. 261-268, XP028669972, ISSN: 0014-5793, DOI: 10.1016/J.FEBSLET.2013. 10.016.

Stech, Marlitt et al., "A Continuous-Exchange Cell-Free Protein Synthesis System Based on Extracts from Cultured Insect Cells", PLoS ONE vol. 9, Issue 5, May 7, 2014, 1-12.

Theall, Gail et al., "Regulation of Biosynthesis of Aminoacyl-tRNA Synthetases and of tRNA in Escherichia coli", Malec. gen. Genet. vol. 169, 1979, 205-211.

Alegria-Schaffer A., et al., "Performing and Optimizing Western Blots with an Emphasis on Chemiluminescent Detection," Methods in Enzymology, 2009, vol. 463, pp. 573-599.

Angov E: "Codon usage: Nature's roadmap to expression and folding of proteins", Biotechnology Journal, 2011, vol. 6, pp. 650-659.

Beaucage SL et al., "Deoxynucleoside phosphoramidite—A new class of key intermediates for deoxypolynucleotide synthesis", Tetrahedron Letters, vol. 22, No. 20, 1981, pp. 1859-1862.

Brown EL et al., "Chemical synthesis and cloning of a tyrosine tRNA gene", Methods in Enzymology, vol. 68, 1979, pp. 109-151.

Currin A., et al., "Speedygenes: An Improved Gene Synthesis Method for the Efficient Production of Error-corrected, Synthetic Protein Libraries for Directed Evolution," Protein Engineering, Design & Selection, Aug. 2014, vol. 27, No. 9, pp. 273-280.

Diehl F., et al., "Beaming: Single-molecule Pcr on Microparticles in Water-in-oil Emulsions," Nature Methods, Jul. 2006, vol. 3, No. 7, pp. 551-559.

Dressman D., et al., "Transforming Single DNA Molecules Into Fluorescent Magnetic Particles for Detection and Enumeration of

(56) References Cited

OTHER PUBLICATIONS

Genetic Variations," Proceedings of the National Academy of Sciences of the United States of America, Jul. 22, 2003, vol. 100, No. 15, pp. 8817-8822.

Fakruddin et al., "Nucleic acid amplification: Alternative methods of polymerase chain reaction", Journal of Pharmacy and Bioallied Sciences, 2013, vol. 5, No. 4, pp. 245-252.

Goodchild: "Conjugates of Oligonucleotides and Modified Oligonucleotides: A Review of Their Synthesis and Properties", Bioconjugate Chemistry, vol. 1, No. 3, 1990, pp. 165-187.

Huang, et al., "A simple, high sensitivity mutation screeing using Ampligase mediated T7 endonuclease I and Surveyor nuclease with microfluidic capillary electrophoresis", Electroohoresis vol. 33, No. 5, Mar. 21, 2012, 788-796.

Ibba M., "Transfer RNA Comes of age," RNA, 2015, vol. 21, No. 4, pp. 648-649.

Kilb N., et al., "Protein Microarray Generation by in Situ Protein Expression from Template DNA," Engineering in Life Sciences, 2014, vol. 14, No. 4, pp. 352-364.

McCullum., et al., "Random Mutagenesis by Error-prone PCR," Methods Mol Biol. 2010, vol. 634, pp. 103-109.

Merrifield R.B., "Solid Phase Peptide Synthesis. I. The Synthesis of a Tetrapeptide," Journal of the American Chemical Society, Jul. 20, 1963, vol. 85, pp. 2149-2154.

Narang SA et al., "Improved phosphotriester method for the synthesis of gene fragment", Methods in Enzymology, vol. 68, 1979, pp. 90-99.

Neylon C., "Chemical and Biochemical Strategies for the Randomization of Protein Encoding DNA Sequences: Library Construction Methods for Directed Evolution," Nucleic Acids Research, 2004, vol. 32, No. 4, pp. 1448-1459.

Pang Y.L.J., et al., "Diverse Cell Stresses Induce Unique Patterns of tRNA Up-and Down-regulation: tRNA-seq for Quantifying Changes in tRNA Copy Number," Nucleic acids research, 2014, vol. 42, No. 22, 10 pages.

Quan J., et al., "Circular Polymerase Extension Cloning of Complex Gene Libraries and Pathways", PLOS ONE, Public Library of Science, US, vol. 4, No. 7, e6441, Jul. 30, 2009, XP002729117, 6 pages.

Saaem et al., "Error correction of microchip synthesized genes using Surveyor nuclease", Nucleic Acids Research, 2012, vol. 40, No. 3, e23, 8 pages.

Sato S., et al., "Artificial Darwinian Selection Technology on Microarray Chips Towards Directed Evolution Using Single Molecule Processing," 16th International Conference on Miniaturized Systems for Chemistry and Life Sciences, Oct. 28-Nov. 1, 2012, pp. 124-126.

Tanaka et al., "High-throughput Protein Microarrays: Feature Size Effects on Printing Arrays with in Situ Protein Synthesis," 16th International Conference on Miniaturized Systems for Chemistry and Life Sciences, Oct. 28-Nov. 1, 2012, pp. 1297-1299.

Ulrich A.K., et al., "Strains overproducing tRNA for histidine," Molecular and General Genetics, 1986, vol. 205, No. 3, pp. 540-545.

Yang et al., "Construction of recombinant DNA by exonuclease recession", Nucleic Acids Research, 1993, vol. 21, No. 8, pp. 1889-1893.

* cited by examiner

Human CCND1 Coding Region: GC Content 61.2%

Region 1
64.0% GC

ATGGAACACCAGCTCCTGTGCTGCGAAGTGGAAACCATCCGCCGCGTA    50
CCCCGATGCCAACCTCCTCAACGACCGGGTGCTGCGGGGCCATGCTGAAGG    100

Region 2
62.0% GC

CGGAGGAGACCTGCGCGCCCTGGTGTCCTACTTCAAATGTGTGCAGAAG    150
GAGGTCCTGCCGTCCATGCGGAAGATCGTCGCCACCTGGATGCTGGAGGT    200

Region 3
62.0% GC

CTGCGAGGAACAGAAGTGCCGAGGAGGAGGTCTTCCCGCTGGCCATGAACT    250
ACCTGGACCGGCTTCCTGTCGCTGGGAGCCCGTGAAAAAGAGCCGGCCTGCAG    300

Region 4
60.0% GC

CTGCTGGGGGCCACTTGCATGTTCGTGGCCTCTAAGATGAAGGAGACCAT    350
CCCCCTGACGGCGCCGAGAAGCTGTGCATCTACACCGACAACTCCATCCGGC    400

Region 5
55.0% GC

CCGAGGAGCTGCTGCAAATGGAGCTGCTCCTGGTGAACAAGCTCAAGTGG    450
AACCTGGCCCGCCAATGACCCCGCACGATTTCATTGAACACTTCCTCTCCAA    500

Region 6
54.0% GC

AATGCCAGAGGCGGAGGAGAACAAACAGATCATCCGCAAACACGCGCAGA    550
CCTTCGTTGCCCCTCTGTGCCACAGATGTGAAGTTCATTTCCAATCCGCCC    600

Region 7
63.0% GC

TCCATGGTGGCAGCGGTGGCGTGGTGGGCCAGTGCAAGGCCTGAACCT    650
GAGGAGCCCCAACAACTTCCTGTCCTACTACCGGCCTCACACGCTTCCTCT    700

Region 8
64.0% GC

CCAGAGTGATCAAGTGTGACCCGGACTGCCTCCGGGCCTGCCAGGAGCAG    750
ATCGAAGCCCTGCTGGAGTCAAGCTCGCGCCAGCCCAGAGAACATGGA    800

Region 9
68.2% GC

CCCCAAGGCCGCCGAGGAGGAGGAAGAGGAGGAGGAGGTGGACCTGG    850
CTTGCACACCCACCGACGTGCGGGACGTGGACATC    885

FIG. 3

Low GC CCND1 Coding Region: GC Content 29.7%

Region 1
30.0% GC
ATGGAACATCAATTGTTGTGTTGTTGTGAAGTTGAAACTATAAGAAGAGCTTA
CCCAGAGATGCTAATTTATTAAATGATAGAGAGTTTTAAGAGCTATGTTAAAAAG Region 2
32.0% GC
CTGAAGAAACTTGTGCTCCATCTGTTTCTTACTTTAAATGTGTTCAAAAAA
GAAGTTTTACCATCTATGAGAAAAATAGTTGCTACTTGGATGTTAGAAGT Region 3
25.0% GC
TTGTGAAGAACAAAAATGTGAAGAAGAAGTTTTTCCATTAGCTATGAATT
ACTTAGATAGATTTTATCTTTAGAACCAGTTAAAAAAATCTAGATTACAA Region 4
30.0% GC
TTGTTGGGTGCTACTTGTATGTTTGTTGCTTCTAAAAATGAAAGAAACTAT
ACCATTAACGGCTGAAAAATTATGTATATACACTGATAATTCTATAAGAC Region 5
24.0% GC
CAGAAGAATTGTTGCAAATGGAATTATTATTAGTTAATAAATTAAAAATGG
AATTTAGCTGCAATGACTCCCACATGATTTTATTGAACACATTTTTATCTAA Region 6
29.0% GC
AATGCCAGAAGCTGAAGAAATAAACAAATAATAAGAAAAACATGCTCAAA
CTTTTGTTGCTTATGTGCTACTGATGTTAAATTTATTTCTAATCCACCA Region 7
31.0% GC
TCTATGGTTGCAGCTGGTTCTGTTGTTGTTGCTGCAGTTCAAGGCTTAAATTT
AAGAATCTCCAAATAATTTTTATCTTACTACAGATTAACTAGATTTTTAT Region 8
32.0% GC
CTAGAGTTATAAAATGTGATCCAGATTGTTTGAAGAGCTTGTCAAGAACAA
ATAGAAGCTTTGTTGGAATCATCTTTAAGACAAGCTCAACAAAATATGGA Region 9
35.3% GC
TCCAAAAGCTGCTGAAGAAGAAGAAGAAGAAGAAGAAGAAGTTGATTTAG
CTTGTACTCCCAACTGATGTTAGAGAGATGTTGATATA

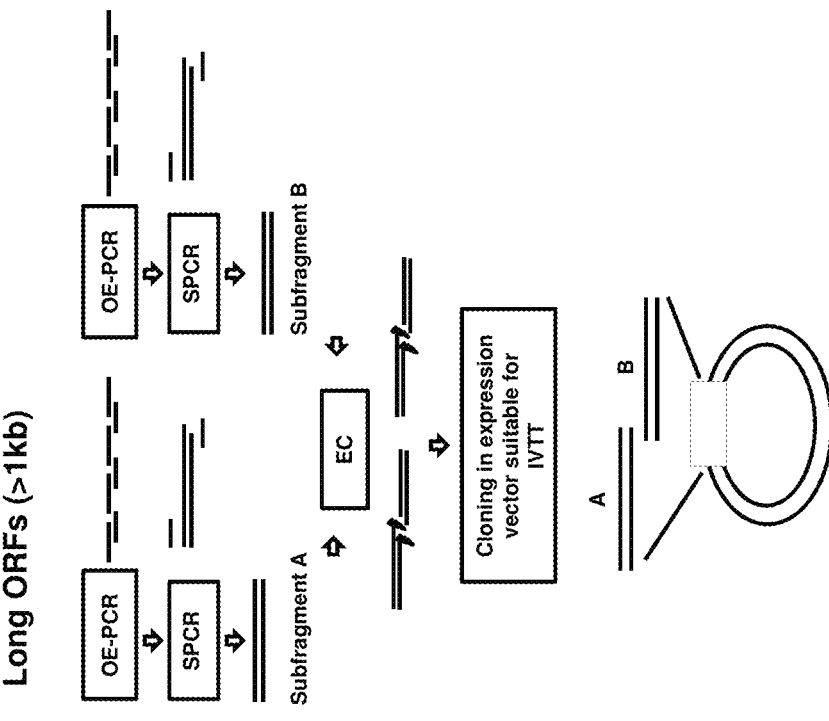
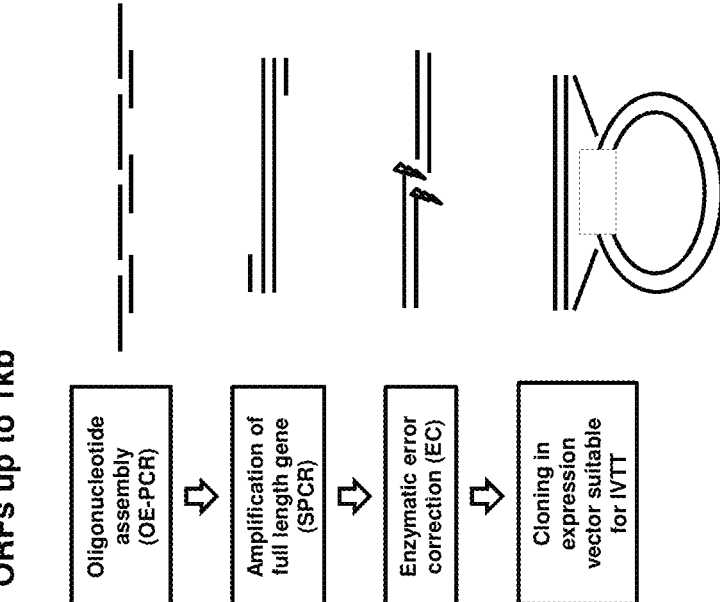
Fig. 9B

SEQUENCE LISTING

```
<160> NUMBER OF SEQ ID NOS: 20

<210> SEQ ID NO 1
<211> LENGTH: 10
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
gccaccaugg                                                            10

<210> SEQ ID NO 2
<211> LENGTH: 11
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 2
uaaggaggug a                                                              11

<210> SEQ ID NO 3
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 3

His His His His His His
1               5

<210> SEQ ID NO 4
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic His tag"
<220> FEATURE:
<221> NAME/KEY: VARIANT
<222> LOCATION: (6)..(9)
<223> OTHER INFORMATION: /replace=" "
<220> FEATURE:
<221> NAME/KEY: MISC_FEATURE
<222> LOCATION: (6)..(9)
<223> OTHER INFORMATION: /note="Variant residues given in the sequence
      have no preference with respect to those in the annotations for
      variant positions"
<220> FEATURE:
<221> NAME/KEY: MISC_FEATURE
<222> LOCATION: (1)..(9)
<223> OTHER INFORMATION: /note="This sequence may encompass 5-9 His
      residues"

<400> SEQUENCE: 4

His His His His His His His His His
1               5

<210> SEQ ID NO 5
<211> LENGTH: 134
<212> TYPE: PRT
<213> ORGANISM: Homo sapiens

<400> SEQUENCE: 5

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95
```

```
Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130

<210> SEQ ID NO 6
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 10xHis tag"

<400> SEQUENCE: 6

His His His His His His His His His His
1               5                   10

<210> SEQ ID NO 7
<211> LENGTH: 885
<212> TYPE: DNA
<213> ORGANISM: Homo sapiens

<400> SEQUENCE: 7
atggaacacc agctcctgtg ctgcgaagtg gaaaccatcc gccgcgcgta ccccgatgcc      60
aacctcctca acgaccgggt gctgcgggcc atgctgaagg cggaggagac ctgcgcgccc     120
tcggtgtcct acttcaaatg tgtgcagaag gaggtcctgc cgtccatgcg gaagatcgtc     180
gccacctgga tgctggaggt ctgcgaggaa cagaagtgcg aggaggaggt cttcccgctg     240
gccatgaact acctggaccg cttcctgtcg ctggagcccg tgaaaaagag ccgcctgcag     300
ctgctggggg ccacttgcat gttcgtggcc tctaagatga aggagaccat cccctgacg     360 gccgagaagc tgtgcatcta caccgacaac tccatccggc cgaggagct gctgcaaatg     420 gagctgctcc tggtgaacaa gctcaagtgg aacctggccg caatgacccc gcacgatttc     480
attgaacact cctctccaa aatgccagag gcggaggaga caaacagat catccgcaaa     540 cacgcgcaga ccttcgttgc cctctgtgcc acagatgtga agttcatttc caatccgccc     600
tccatggtgg cagcggggag cgtggtggcc gcagtgcaag cctgaacct gaggagcccc     660 aacaacttcc tgtcctacta ccgcctcaca cgcttcctct ccagagtgat caagtgtgac     720
ccggactgcc tccgggcctg ccaggagcag atcgaagccc tgctggagtc aagcctgcgc     780
caggcccagc agaacatgga cccaaggcc gccgaggagg aggaagagga ggaggaggag     840
gtggacctgg cttgcacacc caccgacgtg cgggacgtgg acatc                      885

<210> SEQ ID NO 8
<211> LENGTH: 885
<212> TYPE: DNA
<213> ORGANISM: Unknown
<220> FEATURE:
<221> NAME/KEY: source
<223> OTHER INFORMATION: /note="Description of Unknown:
      Codon optimized wild-type polynucleotide"

<400> SEQUENCE: 8
atggaacatc aattgttgtg ttgtgaagtt gaaactataa gaagagctta cccagatgct      60
aatttattaa atgatagagt tttaagagct atgttaaaag ctgaagaaac ttgtgctcca     120
tctgtttctt actttaaatg tgttcaaaaa gaagtttac catctatgag aaaaatagtt     180
```

-continued

```
gctacttgga tgttagaagt ttgtgaagaa caaaaatgtg aagaagaagt ttttccatta      240
gctatgaatt acttagatag attttttatct ttagaaccag ttaaaaaatc tagattacaa      300
ttgttgggtg ctacttgtat gtttgttgct tctaaaatga aagaaactat accattaacg      360
gctgaaaaat tatgtatata cactgataat tctataagac cagaagaatt gttgcaaatg      420
gaattattat tagttaataa attaaaatgg aatttagctg caatgactcc acatgatttt      480
attgaacatt ttttatctaa aatgccagaa gctgaagaaa ataaacaaat aataagaaaa      540
catgctcaaa cttttgttgc tttatgtgct actgatgtta aatttatttc taatccacca      600
tctatggttg cagctggttc tgttgttgct gcagttcaag gcttaaattt aagatctcca      660
aataattttt tatcttacta cagattaact agattttttat ctagagttat aaaatgtgat      720
ccagattgtt taagagcttg tcaagaacaa atagaagctt tgttggaatc atctttaaga      780
caagctcaac aaaatatgga tccaaaagct gctgaagaag aagaagaaga agaagaagaa      840
gttgatttag cttgtactcc aactgatgtt agagatgttg atata                       885

<210> SEQ ID NO 9
<211> LENGTH: 1666
<212> TYPE: DNA
<213> ORGANISM: Homo sapiens

<400> SEQUENCE: 9
acgccagctg gcgaaagggg gatgtgctgc aaggcgatta agttgggtaa cgccagggtt       60
ttcccagtca cgacgttgta aaacgacggc cagtgaattg taatacgact cactataggg      120
cgaattaatt ccggttattt tccaccatat tgccgtcttt tggcaatgtg agggcccgga      180
aacctggccc tgtcttcttg acgagcattc ctagggggtct ttccctctc gccaaaggaa      240 tgcaaggtct gttgaatgtc gtgaaggaag cagttcctct ggaagcttct tgaagacaaa      300
caacgtctgt agcgaccctt tgcaggcagc ggaacccccc acctggcgac aggtgcctct      360
gcggccaaaa gccacgtgta taagatacac ctgcaaaggc ggcacaaccc cagtgccacg      420
ttgtgagttg gatagttgtg aaagagtca aatggctcac ctcaagcgta ttcaacaagg      480
ggctgaagga tgcccagaag gtaccccatt gtatgggatc tgatctgggg cctcggtgca      540
catgctttac atgtgtttag tcgaggttaa aaaacgtcta ggccccccga accacgggga      600
cgtggttttc ctttgaaaaa cacgatgata atatggccac cgaacaccag ctcctgtgct      660
gcgaagtgga aaccatccgc cgcgcgtacc ccgatgccaa cctcctcaac gaccgggtgc      720
tgcgggccat gctgaaggcg gaggagacct gcgcgccctc ggtgtcctac ttcaaatgtg      780
tgcagaagga ggtcctgccg tccatgcgga agatcgtcgc cacctggatg ctggaggtct      840
gcgaggaaca gaagtgcgag gaggaggtct tcccgctggc catgaactac ctggaccgct      900
tcctgtcgct ggagcccgtg aaaaagagcc gcctgcagct gctggggggc acttgcatgt      960
tcgtggcctc taagatgaag gagaccatcc ccctgacggc cgagaagctg tgcatctaca     1020
ccgacaactc catccggccc gaggagctgc tgcaaatgga gctgctcctg gtgaacaagc     1080
tcaagtggaa cctggccgca atgacccgc acgatttcat tgaacacttc ctctccaaaa     1140
tgccagaggc ggaggagaac aaacagatca tccgcaaaca cgcgcagacc ttcgttgccc     1200
tctgtgccac agatgtgaag ttcatttcca atccgccctc catggtggca gcggggagcg     1260
tggtggccgc agtgcaaggc ctgaacctga ggagccccaa caacttcctg tcctactacc     1320
gcctcacacg cttcctctcc agagtgatca agtgtgaccc ggactgcctc cgggcctgcc     1380
```

-continued

```
aggagcagat cgaagccctg ctggagtcaa gcctgcgcca ggcccagcag aacatggacc    1440
ccaaggccgc cgaggaggag gaagaggagg aggaggaggt ggacctggct tgcacaccca    1500
ccgacgtgcg ggacgtggac atcttgcacc atcatcacca ccattgatga gatctgactg    1560
aaaaaaaaaa aaaaaaaaaa aaaaaaaaaa gtttaaacac tagtccgctg agcaataact    1620
agcataaccc cttggggcct ctaaacgggt cttgagggggt tttttg                  1666

<210> SEQ ID NO 10
<211> LENGTH: 918
<212> TYPE: DNA
<213> ORGANISM: Saccharomyces cerevisiae

<400> SEQUENCE: 10
atggccaccg aacaccaatt attgtgttgt gaagttgaaa ccattagaag agcttaccca      60
gatgctaact tgttgaacga tagagttttg agagctatgt tgaaggctga agaaacttgt     120
gctccatctg tttcttactt caagtgcgtt caaaaagaag ttttgccatc catgagaaag     180
atcgttgcta cttggatgtt ggaagtttgc gaagaacaaa agtgcgaaga agaagttttt     240
ccattggcca tgaactactt ggacagattc ttgtctttgg aaccagtcaa gaagtccaga     300
ttgcaattat tgggtgctac ctgtatgttc gttgcttcta aaatgaagga aaccattcca     360
ttgaccgctg aaaagttgtg tatctacacc gataactcca tcagacctga gaattattg     420 caaatggaat tgttgttggt caacaagttg aagtggaatt tggctgctat gactccacat     480
gatttcatcg aacatttctt gtccaaaatg ccagaagccg aagaaacaa gcaaatcatt     540 agaaagcacg cccaaacttt cgttgctttg tgtgctactg atgtcaagtt catttctaac     600
ccaccatcta tggttgctgc tggttctgtt gttgctgctg ttcaaggttt gaatttgaga     660
tctccaaaca acttcttgtc ctactacaga ttgaccagat cttgagtag agttatcaag     720 tgtgatccag attgcttgag agcttgccaa gaacaaattg aagctttgtt ggaatcctcc     780
ttgagacaag ctcaacaaaa catggatcca aaagcagctg aggaggagga ggaagaggaa     840
gaagaagttg atttggcttg tactccaacc gatgttagag atgttgatat cttgcaccat     900
catcaccacc attgatga                                                  918

<210> SEQ ID NO 11
<211> LENGTH: 918
<212> TYPE: DNA
<213> ORGANISM: Unknown
<220> FEATURE:
<221> NAME/KEY: source
<223> OTHER INFORMATION: /note="Description of Unknown:
     Codon optimized wild-type polynucleotide"

<400> SEQUENCE: 11
atggccaccg aacaccagct cctgtgctgc gaagtggaaa ccatccgccg cgcgtacccc      60
gatgccaacc tcctcaacga ccgggtgctg cgggccatgc tgaaggcgga ggagacctgc     120
gcgccctcgg tgtcctactt caaatgtgtg cagaaggagg tcctgccgtc catgcggaag     180
atcgtcgcca cctggatgct ggaggtctgc gaggaacaga gtgcgagga ggaggtcttc     240 ccgctggcca tgaactacct ggaccgcttc ctgtcgctgg agcccgtgaa aaagagccgc     300
ctgcagctgc tggggggccac ttgcatgttc gtggcctcta agatgaagga gaccatcccc     360
ctgacggccg agaagctgtg catctacacc gacaactcca tccggcccga ggagctgctg     420
caaatggagc tgctcctggt gaacaagctc aagtggaacc tggccgcaat gacccccgcac     480 gatttcattg aacacttcct ctccaaaatg ccagaggcgg aggagaacaa acagatcatc     540
```

-continued

```
cgcaaacacg cgcagacctt cgttgccctc tgtgccacag atgtgaagtt catttccaat      600
ccgccctcca tggtggcagc ggggagcgtg gtggccgcag tgcaaggcct gaacctgagg      660
agccccaaca acttcctgtc ctactaccgc ctcacacgct tcctctccag agtgatcaag      720
tgtgacccgg actgcctccg ggcctgccag gagcagatcg aagccctgct ggagtcaagc      780
ctgcgccagg cccagcagaa catggacccc aaggccgccg aggaggagga agaggaggag      840
gaggaggtgg acctggcttg cacacccacc gacgtgcggg acgtggacat cttgcaccat      900
catcaccacc attgatga                                                   918
```

```
<210> SEQ ID NO 12
<211> LENGTH: 1275
<212> TYPE: DNA
<213> ORGANISM: Saccharomyces cerevisiae

<400> SEQUENCE: 12
atggccacca ttgctggtcc agaatggttg ttggatagac catctgttaa caactcccaa       60
ttggttgttt ctgttgctgg tactgttgaa ggtactaatc aagacatctc cttgaagttc      120
ttcgaaatcg atttgacttc tagaccagct catggtggta aaactgaaca aggtttgtct      180
ccaaagtcta agccatttgc tactgattct ggtgctatgt ctcataagtt ggaaaaggct      240
gatttgttga aggccatcca agaacaattg attgccaacg ttcattccaa cgatgattac      300
ttcgaagtta tcgatttcgc ttccgatgct actattactg atagaaacgg taaggtttac      360
ttcgccgata aggatggttc tgttactttg ccaactcaac cagtccaaga atttttgttg      420
tctggtcacg ttagagtcag accatacaaa gaaaagccaa tccaaaatca agccaagtcc      480
gttgatgttg aatacactgt tcaattcact ccattgaacc cagatgatga ttttagacca      540
ggtttgaagg ataccaagtt gttgaaaact ttggccattg gtgataccat cacctcccaa      600
gaattattgg ctcaagctca atccatcttg aacaagaatc atccaggtta caccatctac      660
gaaagagatt cttctatcgt tacccacgat aacgatatct tcagaaccat tttgccaatg      720
gaccaagaat tcacctacag agttaagaac agagaacaag cctacagaat caacaaaaag      780
tccggtttga acgaagaaat caacaacacc gatttgatct ccgaaaagta ctacgtttttg      840 aaaaagggtg aaaagccata cgatccattc gatagatctc acttgaagtt gttcaccatc      900
aagtatgttg atgtcgacac caacgaatta ttgaagtccg aacaattatt gaccgcctcc      960
gaaagaaatt tggatttcag agacttgtac gacccaagag ataaggctaa gttgttgtat     1020
aacaatttgg acgccttcgg tatcatggat tatactttga ctggtaaggt cgaagataac     1080
cacgatgata ccaacagaat tatcaccgtc tacatgggta aaagaccaga aggtgaaaac     1140
gcttcttatc atttggctta cgataaggac agatacaccg aagaagaaag agaagtctac     1200
tcctacttga gatataccgg tactccaatt ccagataacc aaaacgataa gcaccatcat     1260
caccaccatt gatga                                                     1275
```

```
<210> SEQ ID NO 13
<211> LENGTH: 1275
<212> TYPE: DNA
<213> ORGANISM: Unknown
<220> FEATURE:
<221> NAME/KEY: source
<223> OTHER INFORMATION: /note="Description of Unknown:
      Codon optimized wild-type polynucleotide"

<400> SEQUENCE: 13
```

-continued

```
atggccacca ttgctgggcc tgagtggctg ctggacaggc catcagtgaa caatagccag      60
ctggtggtct ctgtgccggg aactgtcgaa ggcaccaacc aggatatctc tctgaaattc     120
tttgagattg acctgactag tcgccctgct cacggaggga agaccgagca gggactgtct     180
cccaagagta aacctttcgc taccgattcc ggagcaatgt ctcacaagct ggaaaaagcc     240
gacctgctga aggctatcca ggagcagctg attgcaaacg tgcattcaaa tgacgattac     300
ttcgaagtca tcgattttgc aagcgacgcc accatcacag atagaaacgg aaaagtgtac     360
ttcgccgata aggacggcag tgtgaccctg cccacacagc ctgtccagga gtttctgctg     420
agcgggcatg tgcgggtcag accatacaag gaaaaaccca tccagaacca ggctaagagc     480
gtggacgtgg agtatacagt gcagttcact ccactgaatc ccgacgatga ctttaggccc     540
ggcctgaagg ataccaaact gctgaagaca ctggccatcg gggacactat taccagccag     600
gaactgctgg cccaggctca gtccatcctg aacaaaaatc accccggcta caccatctat     660
gagcgggata gctccattgt gacacatgat aacgacatct tcagaactat tctgcctatg     720
gaccaggagt tcacctacag ggtgaagaat cgcgagcagg cctatcgaat caacaagaaa     780
tccggactga atgaggaaat caacaacact gatctgatct ctgaaaagta ctatgtgctg     840
aagaaaggcg agaagcctta cgatccattc gaccgcagcc acctgaaact gtttaccatt     900
aagtatgtgg atgtcgacac aaacgaactg ctgaaaagtg agcagctgct gaccgcctca     960
gaacgaaatc tggatttccg ggacctgtac gatccacggg acaaggctaa actgctgtat    1020
aacaatctgg atgcatttgg catcatggac tacacactga ctgggaaggt ggaggacaac    1080
cacgatgaca ctaatcgcat cattaccgtc tatatgggga aacgacccga aggagagaac    1140
gcatcctacc atctggccta tgataaggac agatacacag aggaagagag ggaagtctat    1200
tcctacctga gatacactgg cactcccatc cccgacaatc ccaatgacaa acaccatcat    1260
caccaccatt gatga                                                     1275
```

```
<210> SEQ ID NO 14
<211> LENGTH: 726
<212> TYPE: DNA
<213> ORGANISM: Saccharomyces cerevisiae

<400> SEQUENCE: 14
```

```
atggccaccg aatctgatga atctggtttg ccagctatgg aaattgaatg tagaattacc      60
ggtactttga acggtgtcga atttgaattg gttggtggtg gtgaaggtac tccagaacaa     120
ggtagaatga ctaacaaaat gaagtctacc aagggtgctt tgactttctc tccatatttg     180
ttgtctcacg ttatgggtta cggtttctac cattttggta cttatccatc cggttacgaa     240
aacccatttt tacatgctat taacaacggt ggttacacca acaccagaat cgaaaagtat     300
gaagatggtg tgtcttgca cgtttcattc tcttatagat atgaagccgg tagagttatc     360
ggtgatttta aggttatggg tactggtttc ccagaagatt ctgttatttt caccgacaag     420
atcatcagat ctaacgctac tgttgaacac ttgcatccaa tgggtgataa tgatttggat     480
ggttctttta ccagaacctt ctcattgaga gatggtggtt attactcctc cgttgttgat     540
tctcatatgc atttcaagtc cgccattcat ccatctatct tgcaaaatgg tggtccaatg     600
tttgccttca aagagttga agaagatcac tctaataccg aattgggtat cgttgaatac     660
caacatgctt caaaactcc agatgctgat gctggtgaag aacaccatca tcaccaccat     720
tgatga                                                               726
```

-continued

```
<210> SEQ ID NO 15
<211> LENGTH: 726
<212> TYPE: DNA
<213> ORGANISM: Unknown
<220> FEATURE:
<221> NAME/KEY: source
<223> OTHER INFORMATION: /note="Description of Unknown:
      Codon optimized wild-type polynucleotide"

<400> SEQUENCE: 15
atggccaccg agagcgacga gagcggcctg cccgccatgg agatcgagtg ccgcatcacc      60
ggcaccctga acggcgtgga gttcgagctg gtgggcggag agagggaac  ccctgagcag     120 ggccgcatga ccaacaagat gaagagcacc aaaggcgccc tgaccttcag cccctacctg     180
ctgagccacg tgatgggcta cggcttctac cacttcggca cctaccccag cggctacgag     240
aaccccttcc tgcacgccat caacaacggc ggctacacca caccccgcat cgagaagtac     300
gaggacggcg gcgtgctgca cgtgagcttc agctaccgct acgaggccgg ccgcgtgatc     360
ggcgacttca aggtgatggg caccggcttc cccgaggaca gcgtgatctt caccgacaag     420
atcatccgca gcaacgccac cgtggagcac ctgcacccca tgggcgataa cgatctggat     480
ggcagcttca cccgcacctt cagcctgcgc gacggcggct actacagctc cgtggtggac     540
agccacatgc acttcaagag cgccatccac cccagcatcc tgcagaacgg gggccccatg     600
ttcgccttcc gccgcgtgga ggaggatcac agcaacaccg agctgggcat cgtggagtac     660
cagcacgcct tcaagacccc cggatgcagat gccggtgaag aacaccatca tcaccaccat     720
tgatga                                                                 726

<210> SEQ ID NO 16
<211> LENGTH: 963
<212> TYPE: DNA
<213> ORGANISM: Saccharomyces cerevisiae

<400> SEQUENCE: 16
atggccaccg cctctaaagt ttatgatcca gaacaaagaa agagaatgat cactggtcca      60
caatggtggg ctagatgtaa acaaatgaac gttttggact ccttcatcaa ctactacgat     120
tccgaaaaac atgctgaaaa cgccgttatt ttcttgcatg gtaatgctac ctcttcatac     180
ttgtggagac atgttgttcc acatattgaa ccagttgcca gatgcattat tccagatttg     240
attggtatgg gtaaatccgg taaatctggt aacggttcct acagattatt ggaccattac     300
aagtatttga ccgcctggtt cgaattattg aacttgccaa gaagatcat  cttcgttggt     360 catgattggg gttctgcttt ggcttttcat tatgcttacg aacaccaaga tagaatcaag     420
gccatagttc acatggaatc cgttgttgat gttatcgaat cttggatggg ttggccagat     480
attgaagaag aattggcctt gatcaagtcc gaagaaggtg aaaaaatggt cttggaaaac     540
aacttcttcg tcgaaacttt gttgccatcc aagatcatga gaaagttgga accagaagaa     600
ttcgctgctt atttggaacc attcaaagaa aagggtgaag tcagaagacc aactttgtct     660
tggcctagag aaattccatt ggttaagggt ggtaaaccag atgttgttca aatcgtcaga     720
aactacaacg cttacttgag agcttctgat gatttgccaa agttgttcat cgaatctgat     780
ccaggttttt tctccaacgc tatcgttgaa ggtgctaaga agtttccaaa taccgaattc     840
gttaaggtca agggtttaca cttcttacaa gaagatgctc cagacgaaat gggaaagtac     900
attaagtctt tcgtcgaaag agtcttgaag aacgaacaac accatcatca ccaccattga     960
tga                                                                   963
```

-continued

```
<210> SEQ ID NO 17
<211> LENGTH: 963
<212> TYPE: DNA
<213> ORGANISM: Unknown
<220> FEATURE:
<221> NAME/KEY: source
<223> OTHER INFORMATION: /note="Description of Unknown:
      Codon optimized wild-type polynucleotide"

<400> SEQUENCE: 17
atggccaccg cctccaaggt ctacgacccc gagcagcgca agcgcatgat caccggcccc      60
cagtggtggg cccgctgcaa gcagatgaac gtcctcgact ccttcatcaa ctactacgac     120
tccgagaagc acgccgagaa cgccgtcatc ttcctccacg gcaacgccac ctcctcctac     180
ctctggcgcc acgtcgtccc ccacatcgag cccgtcgccc gctgcatcat ccccgacctc     240
atcggcatgg gcaagtccgg caagtccggc aacggctcct accgcctcct cgaccactac     300
aagtacctca ccgcctggtt cgagctcctc aacctcccca agaagatcat cttcgtcggc     360
cacgactggg gctccgccct cgccttccac tacgcctacg agcaccagga ccgcatcaag     420
gccatcgtcc acatggagtc cgtcgtcgac gtcatcgagt cctggatggg ctggcccgac     480
atcgaggagg agctcgccct catcaagtcc gaggagggcg agaagatggt cctcgagaac     540
aacttcttcg tcgagaccct cctcccctcc aagatcatgc gcaagctcga gcccgaggag     600
ttcgccgcct acctcgagcc cttcaaggag aagggcgagg tccgcagacc caccctctcc     660
tggcccagag agatccccct cgtcaagggc ggcaagcccg acgtcgtcca gatcgtccgc     720
aactacaacg cctacctccg cgcctccgac gacctcccca agctcttcat cgagtccgac     780
cccggcttct tctccaacgc catcgtcgag ggcgccaaga agttccccaa caccgagttc     840
gtcaaggtca agggcctcca cttcctccag gaggacgccc ccgacgagat gggcaagtac     900
atcaagtcct tcgtcgagcg cgtcctcaag aacgagcagc accatcatca ccaccattga     960
tga                                                                  963

<210> SEQ ID NO 18
<211> LENGTH: 474
<212> TYPE: DNA
<213> ORGANISM: Saccharomyces cerevisiae

<400> SEQUENCE: 18
atggccaccg aagctgaagc tgaaagaggt aaattgccag gtaaaaagtt gccattggaa      60
gtcttgattg aattggaagc taatgctaga aaggctggtt gtactagagg ttgtttgatt     120
tgcttgtcca agattaagtg taccgccaag atgaagaagt acattccagg tagatgtgct     180
gattatggtg gtgataagaa aactggtcaa gctggtatag ttggtgccat agttgatatt     240
ccagaaatct ccggtttcaa agaaatggaa cctatggaac aattcattgc ccaagttgat     300
agatgcgctg aatgtactac tggttgtttg aaaggtttgg ctaacgttaa gtgctccgat     360
ttgttgaaaa aatggttgcc aggtagatgc gctactttcg ctgataagat tcaatccgaa     420
gttgacaaca ttaagggttt ggctggtgat caccatcatc accaccattg atga           474

<210> SEQ ID NO 19
<211> LENGTH: 474
<212> TYPE: DNA
<213> ORGANISM: Unknown
<220> FEATURE:
<221> NAME/KEY: source
<223> OTHER INFORMATION: /note="Description of Unknown:
      Codon optimized wild-type polynucleotide"
```

-continued

```
<400> SEQUENCE: 19
atggccaccg aggccgaggc cgagaggggc aagctgcccg gcaagaagct gcccctggag      60
gtgctgatcg agctggaggc caacgccagg aaggccggct gcaccagggg ctgcctgatc     120
tgcctgagca agatcaagtg caccgccaag atgaagaagt acatccccgg caggtgcgcc     180
gactacggcg gcgacaagaa gaccggccag gccggcatcg tgggcgccat cgtggacatc     240
cccgagatca gcggcttcaa ggagatggag cccatggagc agttcatcgc ccaggtggac     300
cgctgtgcgg aatgcaccac cggctgcctg aagggcctgg ccaacgtgaa gtgcagcgac     360
ctgctgaaga agtggctgcc gggtcgctgt gctaccttcg ccgacaagat ccagagcgag     420
gtggacaaca tcaaagggtt agcgggcgac caccatcatc accaccattg atga           474

<210> SEQ ID NO 20
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
aaaaaaaaaa                                                             10
```

DEVICES AND METHODS FOR PRODUCING NUCLEIC ACIDS AND PROTEINS

CROSS-REFERENCE TO RELATED APPLICATIONS

This application is a continuation of U.S. patent application Ser. No. 15/766,172 filed Oct. 4, 2016, which is a 371 National Phase Application of International Application No. PCT/US2016/055292 filed Oct. 4, 2016, which claims priority to U.S. Provisional Application No. 62/334,304, filed on May 10, 2016 and also claims to priority to U.S. Provisional Application No. 62/237,765 filed Oct. 6, 2015, which disclosures are herein incorporated by reference in their entirety.

SEQUENCE LISTING

The instant application contains a Sequence Listing which has been submitted electronically in ASCII format and is hereby incorporated by reference in its entirety. Said ASCII copy, created on Sep. 30, 2016, is named LT01052PCT_SL.txt and is 21,362 bytes in size.

FIELD OF THE INVENTION

The present disclosure generally relates to devices, compositions and methods for designing and producing nucleic acid molecules and the production of encoded proteins using these nucleic acid molecules. In some aspect, the disclosure relates to automation for the in vitro generation of coding DNA molecules, the in vitro transcription of these DNA molecules to generate protein coding RNA molecules, and the in vitro translation of these protein coding RNA molecules to produce proteins.

BACKGROUND

There are two main approaches to in vitro protein synthesis. These are based on whether the starting genetic material is RNA or DNA. Standard translation systems, such as HeLa cell lysates, CHO cell lysates, reticulocyte lysates and wheat germ extracts, use RNA as a template, whereas "coupled" and "linked" systems start with DNA templates, which are transcribed into RNA then translated. Each of these systems is discussed below.

Rabbit reticulocyte lysate based translation systems are often used to produce proteins. These are efficient in vitro eukaryotic protein synthesis systems used for translation of exogenous produced RNA templates. Reticulocytes are specialized cells primarily responsible for the synthesis of hemoglobin. These immature red cells contain no nucleus, but do contain mRNA and have the ability to translate this mRNA into globin. Further, exogenous proteins are synthesized at a rate close to that observed in intact reticulocyte cells.

Coupled transcription/translation systems use DNA as a template, RNA is transcribed from the DNA and subsequently translated without any in process purification. Such systems typically combine a prokaryotic phage RNA polymerase and promoter (T7, T3, or SP6) with eukaryotic or prokaryotic extracts to synthesize proteins from exogenous DNA templates. DNA templates for transcription/translation reactions may be cloned into plasmid vectors or generated, for example, by PCR.

Coupled systems are two-step reactions, typically based on transcription with an RNA polymerase, followed by translation using, for example, a rabbit reticulocyte or wheat germ lysate. Transcription and translation reactions are separated in eukaryotic cells because mRNAs are typically produced in the nucleus but translation occurs in the cytoplasm. This is not true, however, in prokaryotic organisms.

In *E. coli*, for example, transcription and translation occur simultaneously within the cell. During transcription, the 5' end of the RNA becomes available for ribosomal binding and undergoes translation while its 3' end is still being transcribed. This early binding of ribosomes to the RNA maintains transcript stability and promotes efficient translation. This bacterial translation system gives efficient expression of either prokaryotic or eukaryotic gene products in a short amount of time. Protein yield and initiation fidelity are often enhanced by the DNA template containing a Shine-Dalgarno ribosome binding site upstream of the initiator codon. Capping of eukaryotic RNA is not required.

There are a number of differences between prokaryotic and eukaryotic mRNA transcripts. Typically, eukaryotic mRNAs are characterized by two post-transcriptional modifications: a 5'-7 methyl-guanylate cap ($m^7G$) and a 3' poly (A) tail. Both modifications are believed to contribute to the stability of the mRNA by preventing degradation. Additionally, the 5' cap structure is believed to enhance the translation of mRNA by helping to bind the eukaryotic ribosome and assuring recognition of the proper AUG initiator codon. This function can vary with the translation system and with the specific mRNA being synthesized. The consensus sequence 5'-GCCACCAUGG-3' (SEQ ID NO: 1), also known as the "Kozak" sequence, is considered to be the strongest ribosomal binding signal in eukaryotic mRNA. For efficient translation initiation, the key elements are the G residue at the +1 position and the A residue at the −3 position. mRNA that lacks the Kozak consensus sequence may be translated efficiently in eukaryotic cell-free systems if it possesses a moderately long 5'-untranslated region (UTR) that lacks stable secondary structure.

In bacteria, the ribosomes tend to be guided to the AUG initiation site by a purine-rich region called the Shine-Dalgarno (SD) sequence. This sequence is complementary to the 3' end of the 16s rRNA in the 30S ribosomal subunit. Upstream from the initiation AUG codon, the SD region has the consensus sequence 5'-UAAGGAGGUGA-3' (SEQ ID NO: 2). Specific mRNAs vary considerably in the number of nucleotides that complement the anti-Shine-Dalgarno sequence of 16S rRNA, ranging from as few as two to nine or more. The position of the ribosome binding site (RBS) in relation to the AUG initiator is very important for efficiency of translation (usually from −6 to −10 relative to the A of the initiation site).

Current in vitro transcription, in vitro translation and coupled in vitro transcription/translation have a number of deficiencies, including the rate at which workflows related to them can be performed and the yield of nucleic acid and protein molecules that they generate. Features of systems set out herein address these and other technical issues.

SUMMARY

The present disclosure relates, in part, to compositions and methods for designing nucleic acid molecules containing protein coding regions and for the production of nucleic acid molecules having the designed coding regions, as well as the use of these nucleic acid molecules for the production of proteins.

In some instances, the invention includes devices, compositions (e.g., reagents) and methods for producing one or more desired proteins. In some instances, compositions and methods of the invention are directed to automated processes that begins with the desire to obtain a particular protein, followed by the design and production of a nucleic acid molecule encoding the particular protein, then followed by transcription of this nucleic acid to generate a messenger RNA (mRNA) molecule and translation of this mRNA to produce the protein. The protein may or may not be separated from various workflow components (e.g., polymerases, ribosomes, transfer RNA molecules, free amino acids, adenosine triphosphate, etc.).

In some specific instances, the invention is directed to methods of producing proteins. These methods may comprise: (a) designing of nucleic acid molecules encoding one or more proteins of interest, (b) generating oligonucleotides encoding subportions of the nucleic acid molecules, (c) assembling the oligonucleotides to produce populations of nucleic acid molecules encoding the proteins, (d) contacting the populations of nucleic acid molecules encoding the proteins with a first mixture suitable for the in vitro transcription and translation (IVTT) of members of the populations of nucleic acid molecules encoding the proteins to form a second mixture, and (e) incubating the second mixture of (d) under conditions suitable for the production of (1) mRNA encoding the proteins and (2) the proteins. In some instances, the first mixture suitable for the in vitro transcription and translation of members of the populations of nucleic acid molecules comprises cellular components (e.g., cellular components suitable for transcription of DNA to form mRNA molecules and translation of the resulting mRNA molecules to produce proteins) of a first organism. Also, some or all of the codons of the nucleic acid molecules encoding the proteins may be optimized for translation in cells of a second organism. Further, the first organism and the second organism may be of the same species or of different species.

In some aspects, the populations of nucleic acid molecules encoding the proteins are linear. In other aspects, the populations of nucleic acid molecules encoding the proteins are circular nucleic acid molecules, such as plasmids. Circular nucleic acid molecules may be synthetically generated by methods of the invention or may be composed of synthetically generated "inserts" that are introduced into or assembled with other nucleic acid components. In some instances, nucleic acid molecules (linear and circular) used in IVTT (or IVTr or IVTl) reactions do not have a region that functions as an origin of replication. This will often be the case where the nucleic acid molecules are produced only for the production of proteins. In instances where one desires to obtain a replicable nucleic acid molecule that encodes proteins of interest, nucleic acid molecules may be generated that contain one or more origins of replication (e.g., a prokaryotic origin of replication and/or a eukaryotic origin of replication). Exemplary origins of replication that may be used in the practice of the invention include E. coli oriC, E. coli ColE1, phage fl, Salmonella pSC101, yeast ARSs, and Epstein-Barr virus oriP.

In many instances, linear nucleic acid molecules will be used in IVTT (and/or IVTr or IVTl) reactions.

Further, nucleic acid molecules used in the practice of the invention may comprise a promoter operable linked to the protein coding regions. One diagrammatic example of a nucleic acid molecule format suitable for use in the practice of the invention is shown in FIG. 12.

It has been observed that the use of certain codons results in increased protein production levels, even when the codons used are not the most optimal codons of cells from which the IVTT (and/or IVTr or IVTl) machinery (e.g., cellular extracts containing ribosomes, tRNA synthetases, charged and uncharged tRNA molecules, RNA polymerases, etc.) is derived from. Thus, in some instances, in vitro transcription and/or translation reagents (e.g., cell extracts) may be generated using cells of a first organism but nucleic acid molecules used in the IVTT (and/or IVTr or IVTl) reactions may contain an increased number (as compared to wild-type coding sequences) of codon that are "optimal" for a second organism.

The invention also includes method of producing proteins, the methods comprising: (a) assembling the oligonucleotides to produce a population of nucleic acid molecules encoding the protein, (b) contacting the population of nucleic acid molecules encoding the protein with a first mixture suitable for the in vitro transcription and translation of members of the population of nucleic acid molecules encoding the protein to form a second mixture, and (c) incubating the second mixture of (d) under conditions suitable for the production of (1) mRNA encoding the protein and (2) the protein, wherein (i) the first mixture suitable for the in vitro transcription and translation of members of the population of nucleic acid molecules comprises cellular components from cells of a first organism and/or (ii) some or all of the codons of the nucleic acid molecules encoding the protein are optimized for translation in a second organism, and wherein the first organism and the second organism are of different species.

Further, during the practice of the invention, tRNA molecules may be exogenously added to reaction mixtures used for IVTT (or IVTl). When tRNA are exogenously added, they may have nucleotide sequences that are the same as tRNA molecules that are present in the cells used to supply the IVTT (or IVTl) machinery (e.g., cell extracts) or different nucleotide sequences. Further, the tRNA molecules may be generated from expression constructs or may be obtained from cells. One example of a commercial tRNA preparation obtained from cells is "Yeast tRNA" (cat. no. AM7119) available from THERMO FISHER SCIENTIFIC®. Thus, in some methods of the invention exogenously added tRNA molecules may be obtained from an organism other than the first organism (e.g., a fungus, such as a yeast). In some instances, the tRNA molecules may be obtained from the second organism (e.g., a fungus, such as a yeast). Further, in some instances, the invention includes reaction mixtures containing at least one synthetically produced transfer RNA molecule. In many instances, synthetically produced transfer RNA molecules will be produced by transcription of DNA molecules.

It has been observed that, generally, the use of nucleic acid molecules having codons having a lower GC content result in the production of more protein than when nucleic acid molecules having a higher GC content are used. This appears to be the case even when the IVTT (and/or IVTr or IVTl) machinery is derived from a cell having preferred codons with a higher GC content. Coding regions may be designed in a number of different ways. One way is that codons may be selected based upon factors such as GC content. In some instances, the lowest GC content codons for all twenty amino acids and/or stop codons may be used. In many instances, high or low GC content (high GC content in particular) may result in a coding sequence that has one or a number of undesirable properties (e.g., repetitive regions, hairpin forming regions, etc.). Thus, the GC content of coding regions will often be balanced against other factors. In many instances, one goal will be to generate a coding sequence with low GC content that may be efficiently manufactured and expressed to produce proteins.

Another way is to choose low GC content codons that are used by and/or are preferred codons for a particular organism (e.g., an organism with preferred codons that average a low GC content, such as *Saccharomyces cerevisiae*). This has the advantage that tRNA molecules may be isolated from that organism and used in IVTT (and/or IVTr or IVTl) reaction mixtures. As noted above, in some instances, some or all of the codons of the nucleic acid molecules encoding desired proteins are optimized for translation in cells of the second organism (e.g., *Saccharomyces cerevisiae*) that has an average GC content below 55%. In additional instances, at least half of the codons of the population of nucleic acid molecules encoding may be the most preferred codons of *Saccharomyces cerevisiae*. Thus, in some aspects, the invention relates to the use of nucleic acid molecules that have at least a 5%, 10%, 15%, 20%, 25%, 30%, or 35% (e.g., from about 5% to about 35%, from about 5% to about 30%, from about 10% to about 35%, from about 10% to about 30%, from about 10% to about 25%, from about 15% to about 35%, from about 20% to about 35%, etc.) lower level of GC bases than the wild-type coding region of a nucleic acid molecule for a cell from which the IVTT (and/or IVTr or IVTl) machinery is derived from. By way of example, as shown in FIG. 3, the codons of the wild-type human CCND1 is composed of 63% GC bases and a nucleic acid molecule with optimized codons for expression in *Saccharomyces cerevisiae* is composed of 29.7% GC bases (see FIG. 4). This results in a difference of 33.3%. Thus, the nucleic acid molecule with optimized codons for expression in *Saccharomyces cerevisiae* is said to have a 33.3% lower level of GC bases than the human wild-type CCND1 coding region.

It has also been observed that alteration of the GC content of nucleic acid coding regions can result in the generation of more protein during IVTT over wild-type coding regions. The invention thus includes compositions and methods where, for at least 75% of proteins, expression of nucleic acid molecules containing preferred codons of the first organism (e.g., the organism from which the IVTT (and/or IVTr or IVTl) machinery is derived from) results in the production of less protein than expression of nucleic acid molecules containing codons for preferred codons of the second organism (e.g., *Saccharomyces cerevisiae*). In many instances, the preferred codons for the second organism will have a lower GC content than the preferred codons for the first organism. Also, in many instances, the first organism will be an animal, such as an insect cell or a mammalian cell. In some instances, the first organism will be human (e.g., HeLa cells).

Table 15 shows the GC content of preferred codons from a number of organisms. The average GC content of the twenty codons and the preferred stop codon of human cells is about 63%. The average GC content of the preferred codons from *Saccharomyces cerevisiae* is about 30%.

The invention further includes compositions and methods where expression of nucleic acid molecules containing codons for preferred codons of the first organism (e.g., human) results in the production of less protein than expression of nucleic acid molecules containing codons for preferred codons of the second organism (e.g., *Saccharomyces cerevisiae*) and wherein the difference in protein production averages greater than about 5%, 10%, 15%, 20%, 30%, or 40% (e.g., from about 5% to about 40%, from about 10% to about 40%, from about 15% to about 40%, from about 20% to about 40%, from about 25% to about 40%, from about 5% to about 35%, from about 15% to about 35%, from about 20% to about 35%, from about 25% to about 35%, etc.).

The invention further includes methods, as well as compositions for performing these methods, for producing proteins comprising: (a) contacting nucleic acid molecules encoding the proteins with a first mixture (Steve, the first and second mixtures are confusing to me) suitable for the in vitro transcription and translation to form a second mixture, and (b) incubating the second mixture of (a) under conditions suitable for the production of (1) mRNAs encoding the proteins and (2) the proteins. In some instances, the first mixture suitable for the in vitro transcription and translation comprises cellular components from cells of a first organism. In some instances, some or all of the codons of the nucleic acid molecules encoding the proteins may be optimized for translation in cells of a second organism that is different than the organism from which the in vitro transcription and translation mixture is derived from. In some instances, transfer RNA molecules derived from the second organism are included in the second mixture during step (b).

The invention further includes reaction mixture comprising: (a) one or more cell extracts obtained from one or more mammalian cells (e.g., human cells), (b) nucleic acid molecules encoding proteins, wherein at least half of the codons encoding the proteins are not preferred codons of the mammalian cells, and (c) transfer RNA molecules obtained from one or more non-mammalian cells (e.g., a yeast such as *Saccharomyces cerevisiae*); wherein the average GC content of the codons encoding the proteins is less than 35%, 40%, 45% or 50%. In some instances, the mammalian cells used to prepare the reaction mixtures will be human cells (e.g., HeLa cells). In some instances, the nucleic acid molecules encoding proteins in the reaction mixtures will be linear or circular nucleic acid molecules or a mixture of the two. In some instances, the coding regions of the nucleic acid molecules encoding proteins will be operable linked to one or more promoter.

The invention further includes mechanical devices that perform work flows of the invention (see, e.g., FIG. 1 and FIG. 2). In some embodiments, these mechanical devices comprise:

(a) one or more control device capable of performing one or more of the following functions: (1) accepting the input of nucleotide or amino acid sequence data, (2) designing nucleic acid molecules corresponding to the input nucleotide sequence or encoding the amino acid sequence, (3) directing reagent flows and incubation times for the synthesis and assembly of nucleic acid molecules designed in (2), and (4) directing reagent flows and incubation times for the in vitro transcription and translation of nucleic acid molecules synthesized by the device using the reagent flows and incubation times for directed in (3), (b) one or more reagent storage reservoirs, (c) one or more reaction sites for the synthesis and assembly of nucleic acid molecules and the in vitro transcription and translation of nucleic acid molecules to produce proteins, and (d) one or more ports for the removal of a nucleic acid molecules and/or proteins produced by the device.

As set out in the workflow shown in FIG. 2, mechanical devices of the invention may further include means for protein detection and/or purification. Protein detection may be qualitative, semi-quantitative, or quantitative. In other words, protein detection may be employed to determine whether there are detectable amounts of protein or may be employed to generate an estimate of the actual amount of protein present. When protein detective is semi-quantitative, not only will the detectability of the protein of interest be determine, a rough amount of the protein of interest (e.g., +/− from about 10% to about 50%, from about 15% to about 50%, from about 20% to about 50%, from about 25% to about 50%, from about 25% to about 70%, from about 15% to about 70%, etc. of the actual amount of protein present) will be yielded.

Protein purification may employ one or more of number of means. Exemplary methods include precipitation, affinity tag (e.g., His tag) purification, protein specific purification (e.g., antibody based affinity chromatography), and molecular weight separations.

In some instances, the control device is further capable of directing reagent flows and incubation times for one or more error correction and/or selection processes. In some instances, the device further comprises a waste reservoir for the storage of reagents that have been removed from one or more reaction site. In some instances, the device comprises one or more reagent reservoirs contain one or more reagent selected from the group consisting of: (a) a washing solution, (b) a mis-match repair endonuclease, (c) a cellular extract suitable for in vitro transcription and/or in vitro translation, and (d) one or more nucleoside phosphoramidite.

In many instances, oligonucleotides will be obtained separately and then introduced into a device of the invention. In such instances, reagent storage related to oligonucleotide synthesis, for example, will not be necessary but may be present when a device capable of generating nucleic acid molecules is designed so that an operator may enter workflows at various points.

The invention further comprises methods, as well as devices for performing such methods, for the production of proteins using mechanical devices, these method comprise entry of amino acid sequences of the protein into the mechanical device, wherein the mechanical device: (a) designs of a nucleic acid molecule encoding the amino acid sequence, (b) generates the nucleic acid molecule encoding the amino acid sequence, and (c) performs in vitro transcription and translation reactions using the nucleic acid molecule generated in step (b).

The invention also includes method for identifying nucleic acid molecules encoding proteins of interest, these methods include those that comprise (a) generating an array of nucleic acid molecules in an expressible format, (b) performing in vitro transcription and translation on a plurality of the arrayed nucleic acid molecules to produce proteins encoded by the nucleic acid molecules, (c) screening the proteins produced in step (b) to identify one or more proteins of interest, and (d) identifying one or more nucleic acid molecules encoding one or more of the one or more proteins of interest. In some instances, each locus of the array may be designed to encode nucleic acid molecules having the same amino acid sequence. Further, the array may be designed to encode a plurality of nucleic acid molecules comprising a library (e.g., a cDNA library). In other instances, the array may be designed to contain nucleic acid molecules encoding a plurality of variants of one or more proteins. Further, such variants of one or more proteins may be designed to differ in amino acid sequence at one or more locations. Additionally, such variants of one or more proteins may be designed to contain different amino acids at a single location or at two or more locations. Further, in such variants, an amino acid that naturally occurs at one or more loci of the variants of one or more proteins is designed to be replaced with an amino acid that does not naturally occur at the one or more loci. Also, the one or more nucleic molecules are attached to solid supports located in wells of a multiwell plate.

Once one or more nucleic acid molecule encoding a protein of interest is identified, the invention may further comprise methods comprising isolating one or more or the one or more nucleic molecules encoding at least one of the one or more proteins of interest.

Further, the GC content of one or more coding regions of one or more the nucleic acid molecules of (a) above (generating an array of nucleic acid molecules in an expressible format) may be in a range selected from the group consisting of from about 30% to about 54%, from about 35% to about 54%, from about 35% to about 50%, from about 40% to about 54%, from about 40% to about 50%, from about 30% to about 45%, and from about 35% to about 54%.

In vitro transcription and translation may be performed in various methods of the invention using a reaction mixture comprising (a) a cell extract obtained from mammalian cells, (b) a nucleic acid molecule encoding a protein, wherein at least half of the codons encoding the protein are not preferred codons of the mammalian cells, and (c) transfer RNA molecules obtained from non-mammalian cells; wherein the average GC content of the codons of one or more of the nucleic acid molecules encoding the one or more proteins of interest is less than 50%.

The invention further includes methods for identifying one or more nucleic acid molecules encoding one or more proteins of interest. Such methods may comprise (a) generating an array of nucleic acid molecules in an expressible format, (b) performing in vitro transcription and translation on a plurality of the arrayed nucleic acid molecules to produce proteins encoded by the nucleic acid molecules, (c) screening the proteins produced in step (b) to identify one or more protein of interest, (d) identifying one or more nucleic acid molecules encoding the proteins of interest, and (e) isolating one or more of the one or more nucleic acid molecules encoding the proteins of interest identified in (d). Further, isolation of the one or more of the one or more nucleic acid molecules encoding the proteins of interest may be mediated by cleavage of the nucleic acid molecules from a surface of a well of a multiwell plate. Also, isolation of the one or more of the one or more nucleic acid molecules encoding the proteins of interest is mediated by the removal of one or more beads from a well of a multiwell plate.

Removal of the one or more beads from a well of a multiwell plate may be mediated by a mechanical device (e.g., a suction device or tweezers). Removal of the one or more beads from a well of a multiwell plate may occur by lifting of the beads with gas bubbles. Further, such the gas bubbles may be generated by electrical current in the well. Also, beads may be lifted from the well into a flow stream. Along such lines, the beads may be transported to one or more locations where nucleic acid molecules may be released from the beads.

Once collected, the one or more nucleic acid molecules may be linked to one or more other nucleic acid molecules. Further, at least one of the one or more other nucleic acid molecules may have an origin of replication. Also, at least one of the one or more other nucleic acid molecules may be one or more plasmid.

BRIEF DESCRIPTION OF THE DRAWINGS

For a more complete understanding of the principles disclosed herein, and the advantages thereof, reference is made to the following descriptions taken in conjunction with the accompanying drawings, in which:

FIG. 3 shows the nucleotide sequence of a *Homo sapiens* CCND1 coding (SEQ ID NO: 7). The coding region contains no introns and is divided into nine sub-regions, eight of which are 100 nucleotides in lengths (11.2% of the total length of the coding region) and one of which is 85 nucleotides in length (9.6% of the total length of the coding region). The overall GC content is 61.2% and the nine regions that the coding region is divided into have GC contents ranging from 54% to 68.2%.

FIG. 4 shows the nucleotide sequence of a yeast codon optimized CCND1 coding region (SEQ ID NO: 8), incorporating preferred codons set out in Table 15. The overall GC content is 29.7% and the nine regions that the coding region is divided into have GC contents ranging from 24% to 35.3%.

FIGS. 5A and 5B is an alignment of the two nucleotide sequences set out in FIG. 3 (SEQ ID NO: 7) and FIG. 4 (SEQ ID NO: 8). Differences between the two sequences are shown as white letters on a black background.

FIGS. 9A and 9B show workflows for assembly and error correction of nucleic acid molecules. On the left side of FIG. 9A, ORFs up to 1 kb are synthesized from one single oligonucleotide set. After oligonucleotide assembly (e.g. by overlap-extension PCR) (OE-PCR) the full length open reading frame is amplified in the presence of terminal primers, referred to herein as sub-assembly PCR (SPCR). An error correction step is performed to remove the errors and the correct DNA template is fused to the UTR regions to build a functional expression cassette, referred to as strings. On the right side of FIG. 9B, ORFs larger than 1 kb are broken up into subfragments (up to three) and synthesized starting from different oligonucleotide sets.

As shown in FIG. 9B, amplified subfragments are optionally combined into a single reaction mix before they are subjected to one or more error correction (EC) cycles. During the error correction, all subfragments are contemporarily treated with a mismatch cleaving endonuclease (such as T7 Endonuclease I) and finally combined with the 5'- and 3' UTRs (e.g. in a fusion PCR step in the presence of terminal primers encoding the 5'- and 3' UTRs) to build the final string assembly.

Figure 16A:
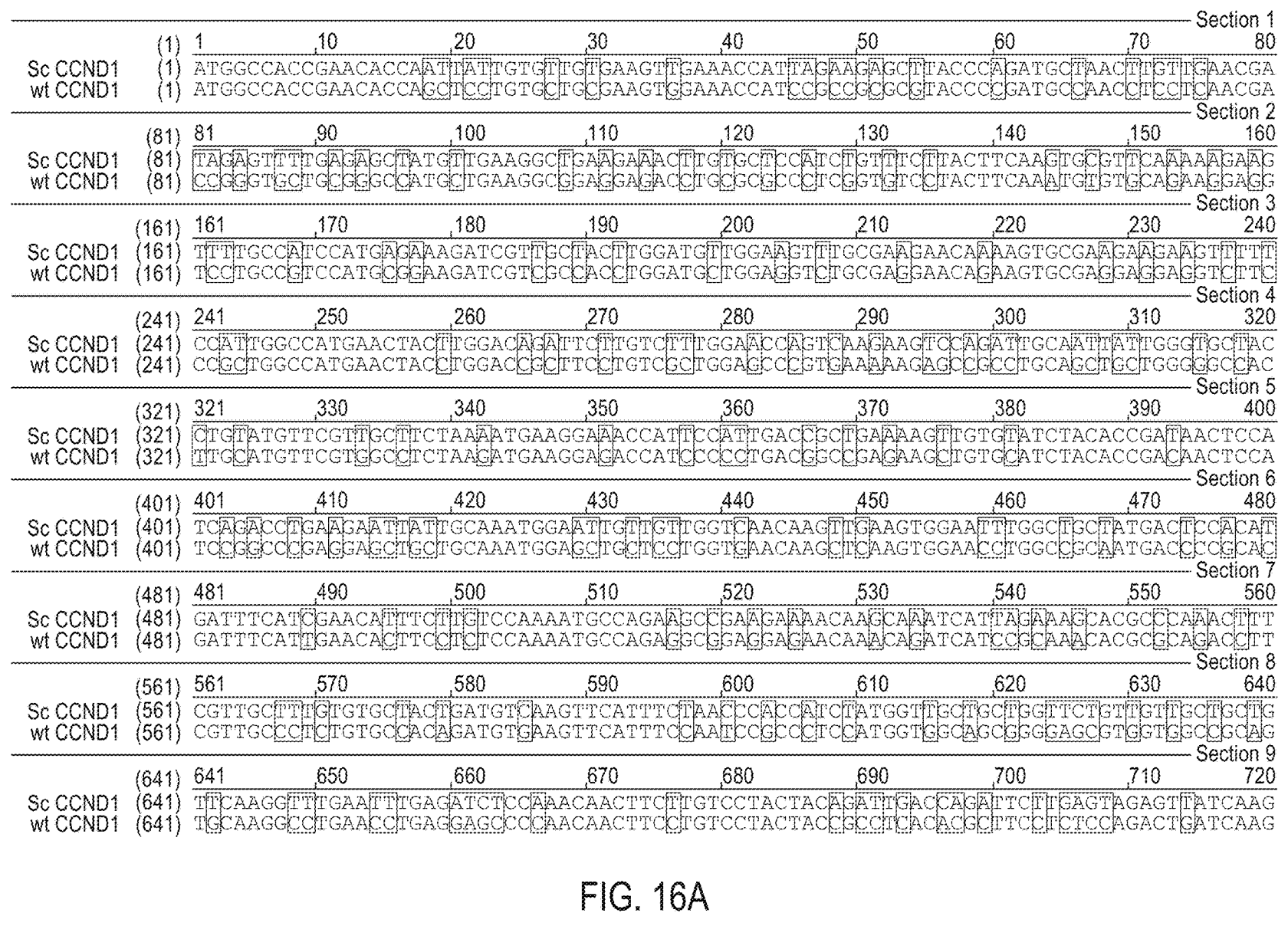
Figure 16B:
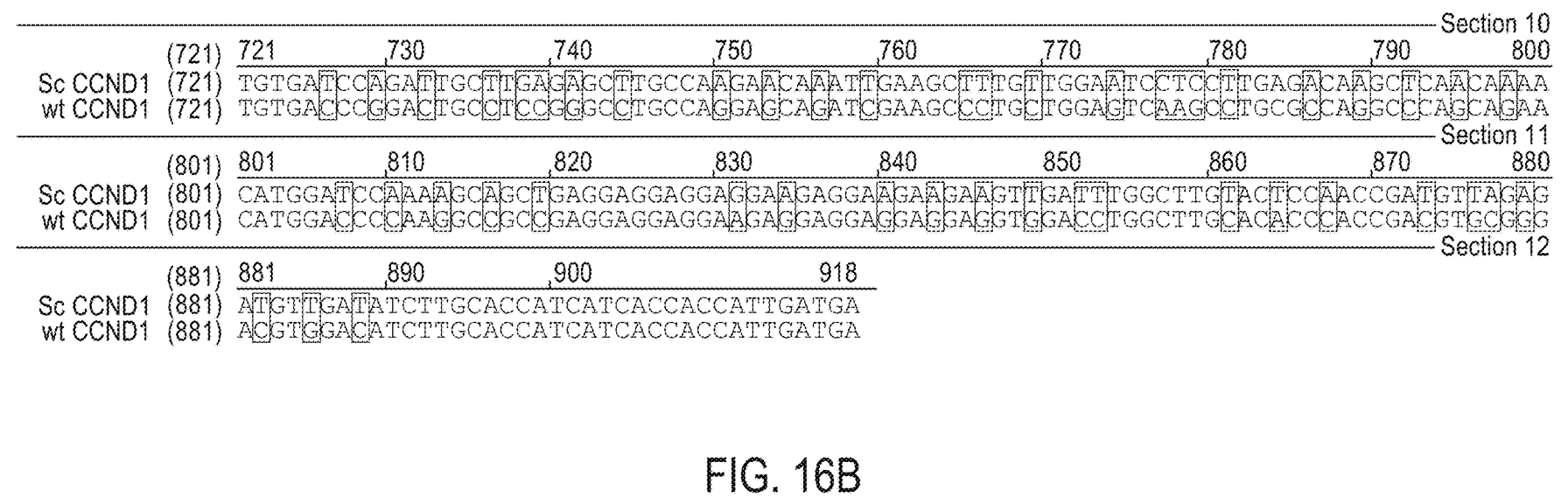

FIGS. 16A-16B shows an alignment of a wild-type (wt) (SEQ ID NO: 11) and a *Saccharomyces cerevisiae* (Sc) (SEQ ID NO: 10) codon optimized nucleotide sequence encoding CCDN1. The GC content of the wt sequence is 60.9% (excluding the stop codon). The GC content of the Sc optimized sequence is 41.0% (excluding the stop codon).

Figure 17A:
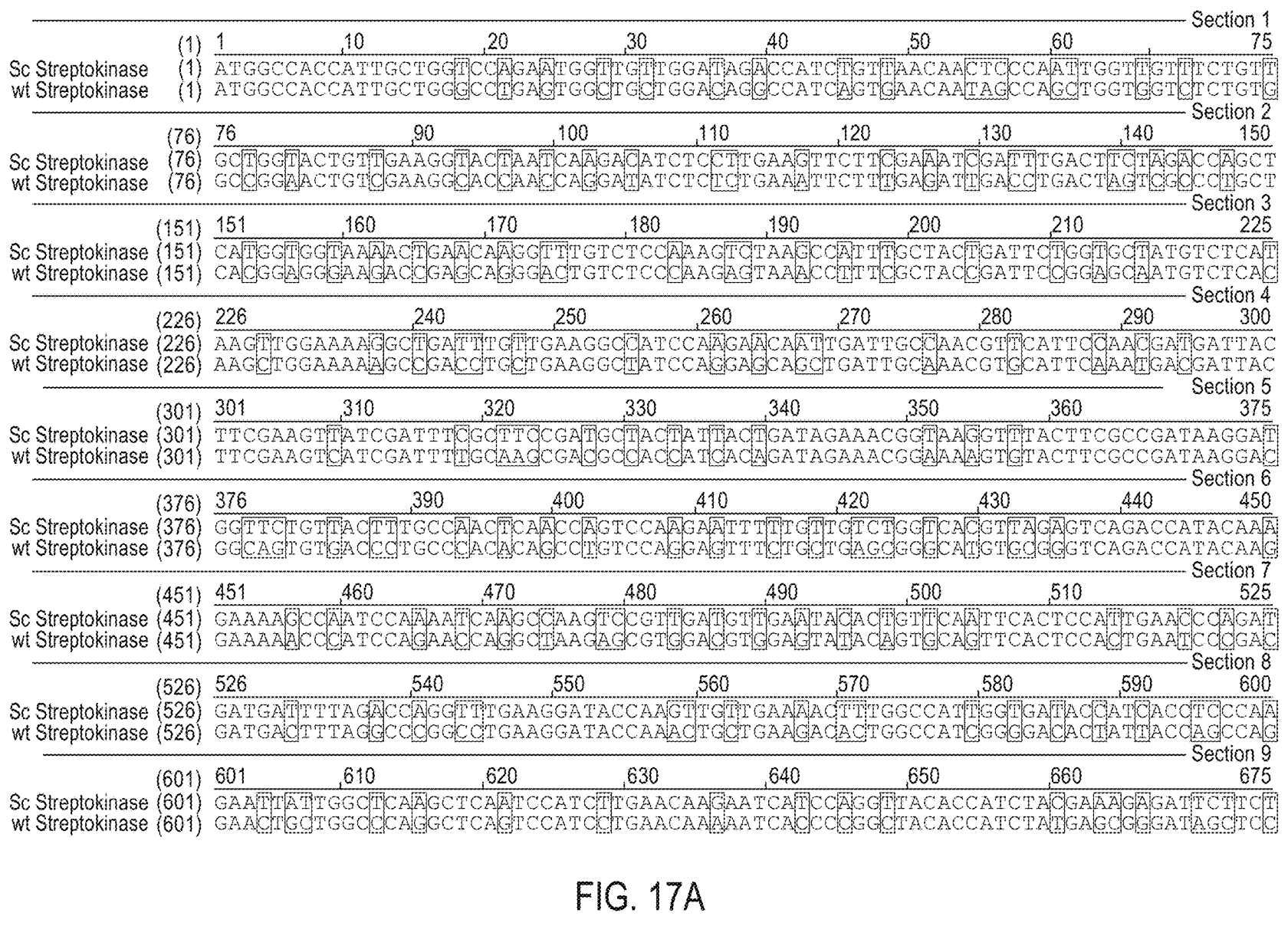
Figure 17B:
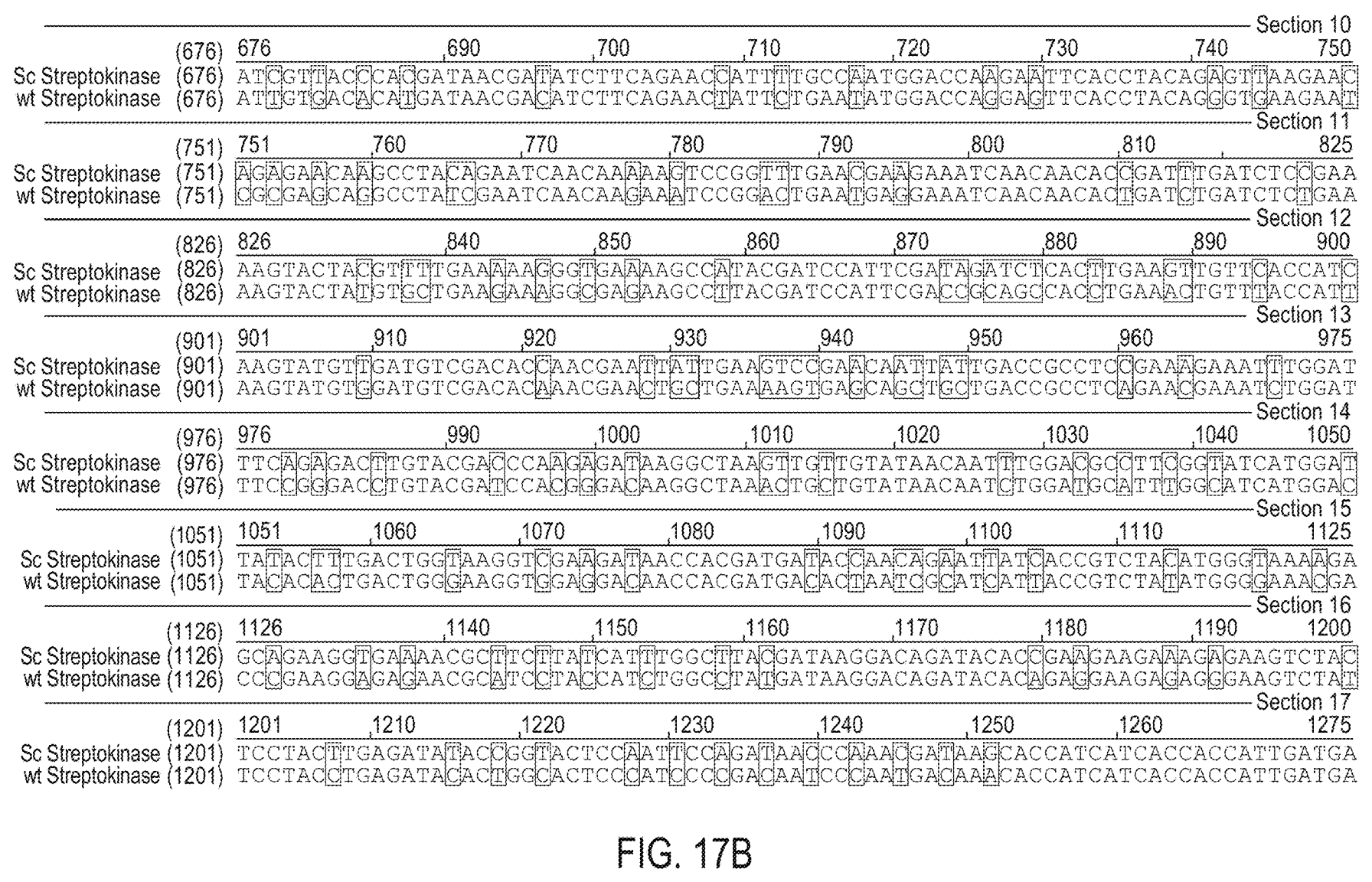

FIGS. 17A-17B show an alignment of a wild-type (wt) (SEQ ID NO: 13) and a *Saccharomyces cerevisiae* (Sc) (SEQ ID NO: 12) codon optimized nucleotide sequence encoding streptokinase. The GC content of the wt sequence is 50.8% (excluding the stop codon). The GC content of the Sc optimized sequence is 40.6% (excluding the stop codon).

Figure 18:
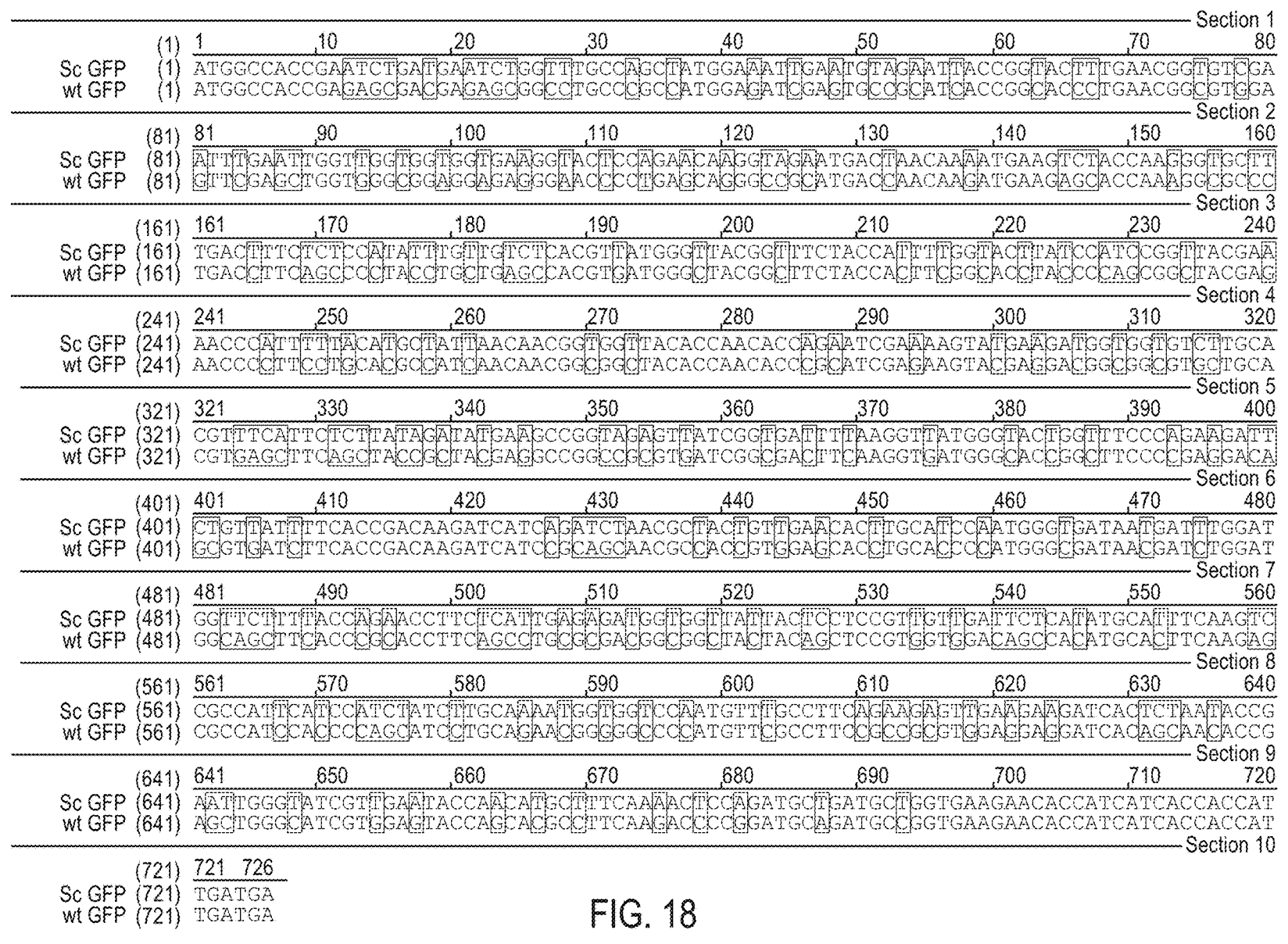

FIG. 18 show an alignment of a wild-type (wt) (SEQ ID NO: 15) and a *Saccharomyces cerevisiae* (Sc) (SEQ ID NO: 14) codon optimized nucleotide sequence encoding GFP. The GC content of the wt sequence is 63.3% (excluding the stop codon). The GC content of the Sc optimized sequence is 40.8% (excluding the stop codon)

Figure 19A:
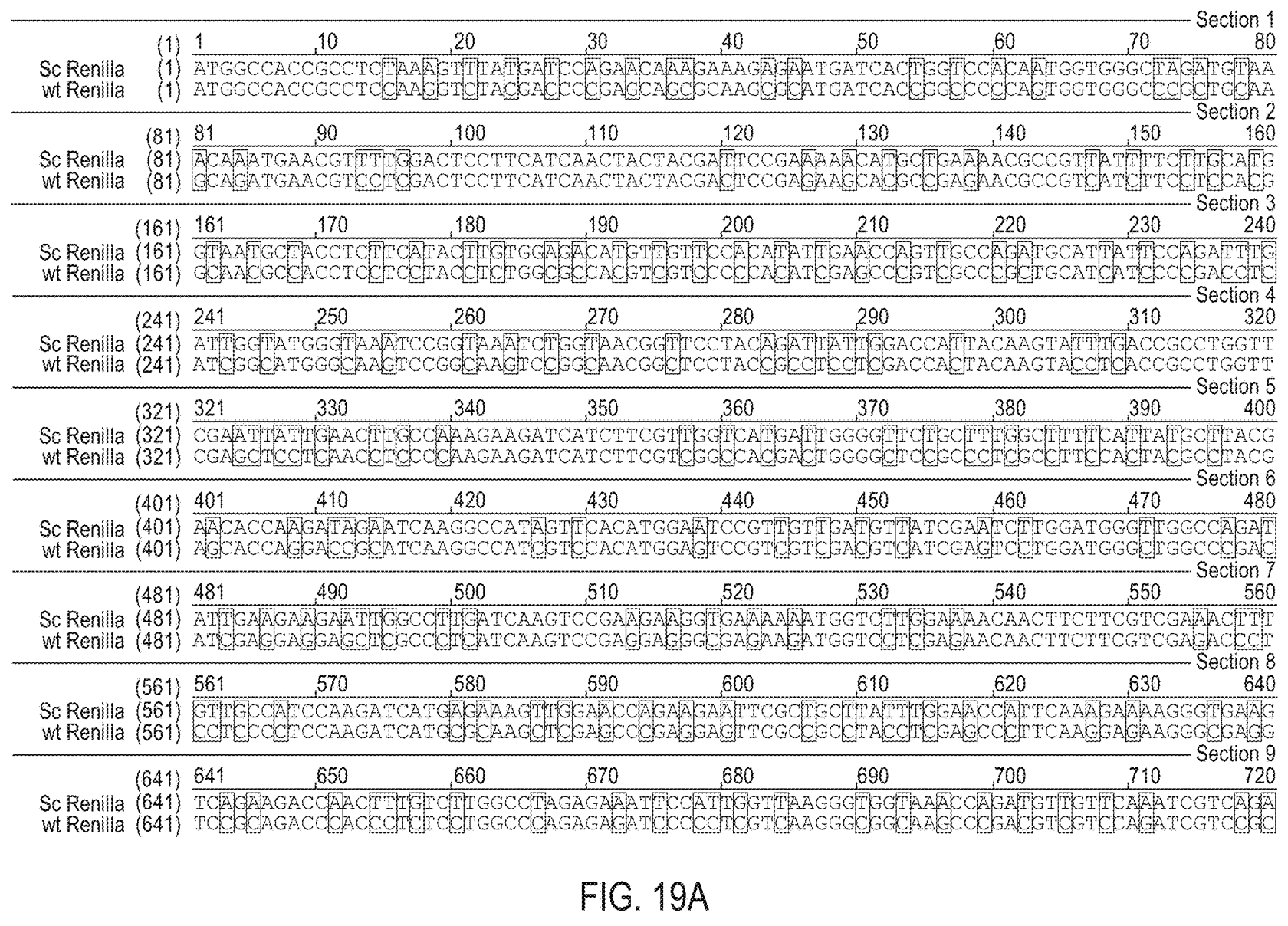
Figure 19B:
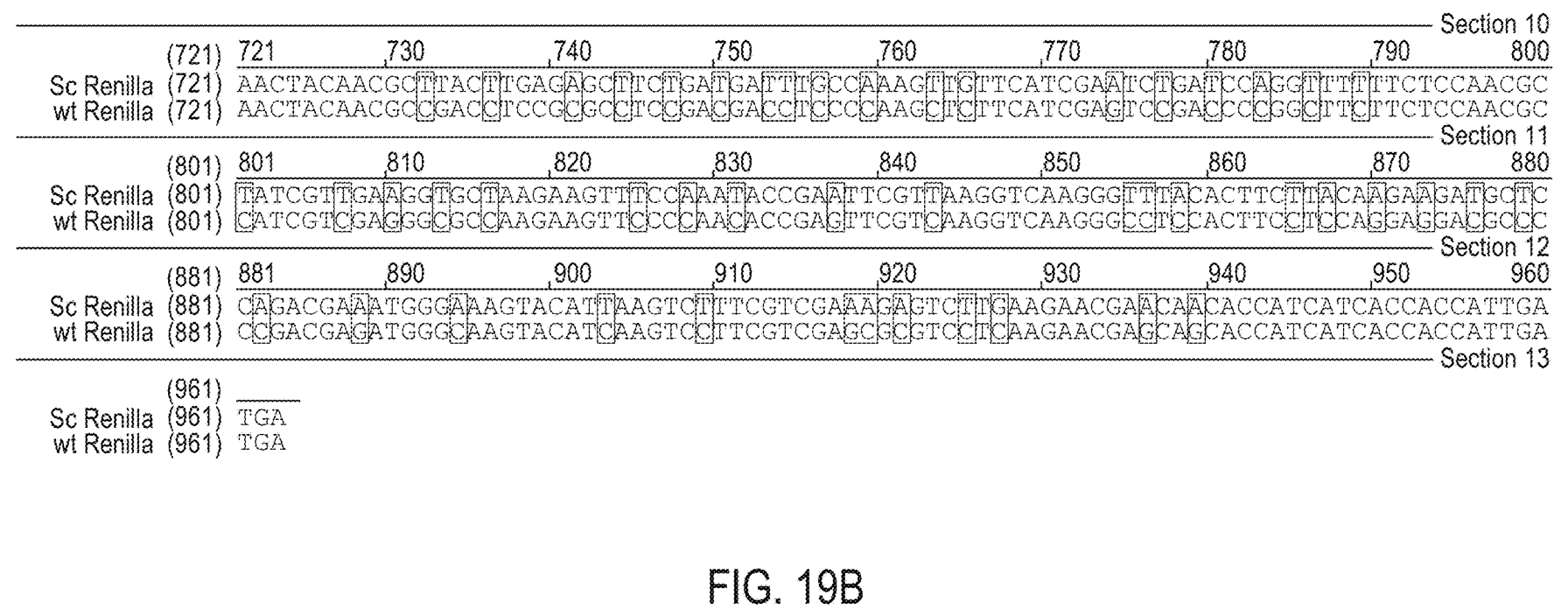

FIG. 19A-19B show an alignment of a wild-type (wt) (SEQ ID NO: 17) and a *Saccharomyces cerevisiae* (Sc) (SEQ ID NO: 16) codon optimized nucleotide sequence encoding Green *Renilla*. The GC content of the wt sequence is 63.0% (excluding the stop codon). The GC content of the Sc optimized sequence is 40.6% (excluding the stop codon).

Figure 20:
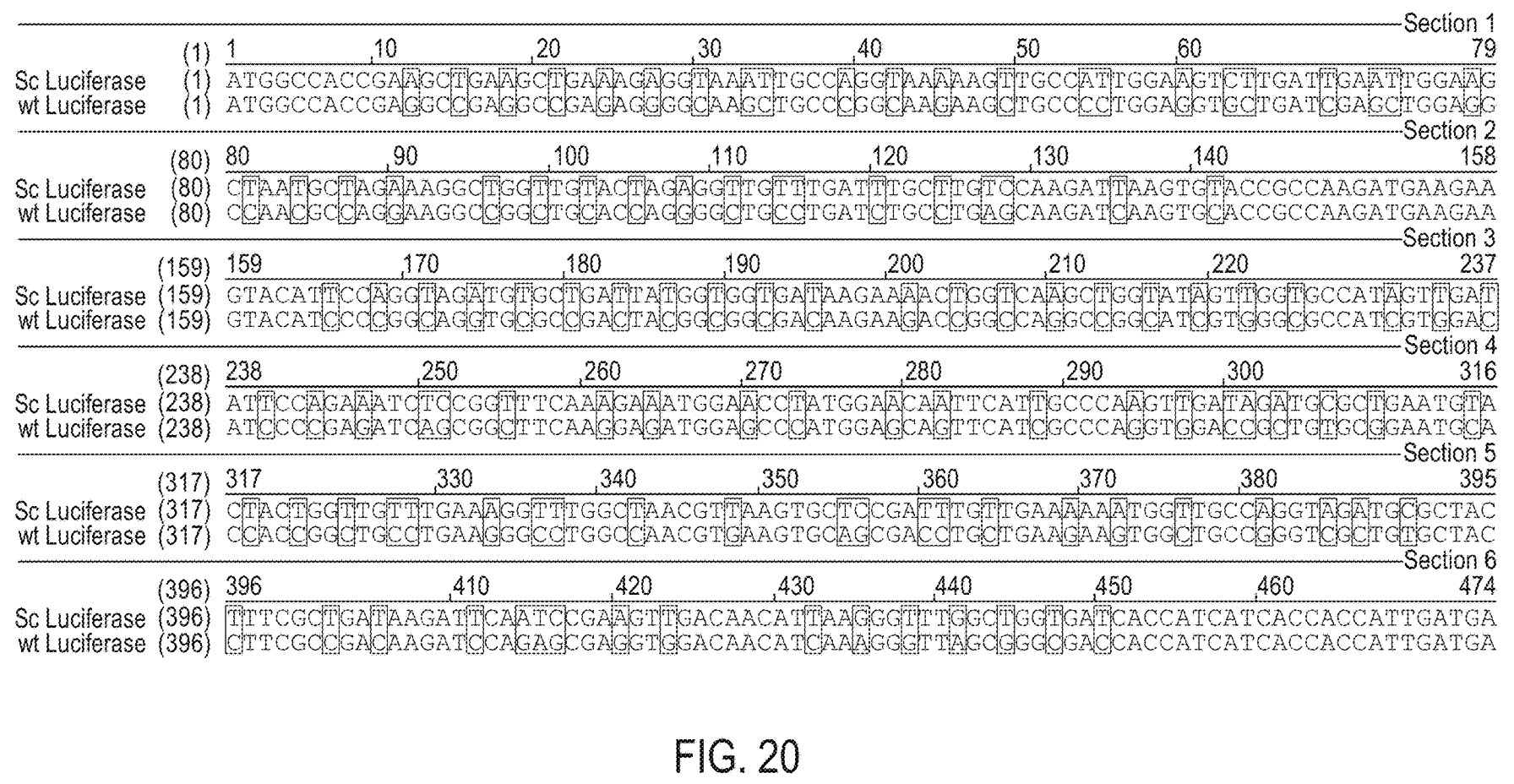

FIG. 20 shows an alignment of a wild-type (wt) (SEQ ID NO: 19) and a *Saccharomyces cerevisiae* (Sc) (SEQ ID NO: 18) codon optimized nucleotide sequence encoding lucifer-ase. The GC content of the wt sequence is 64.1% (excluding the stop codons). The GC content of the Sc optimized sequence is 41.7% (excluding the stop codons).

DETAILED DESCRIPTION

Figure 1:
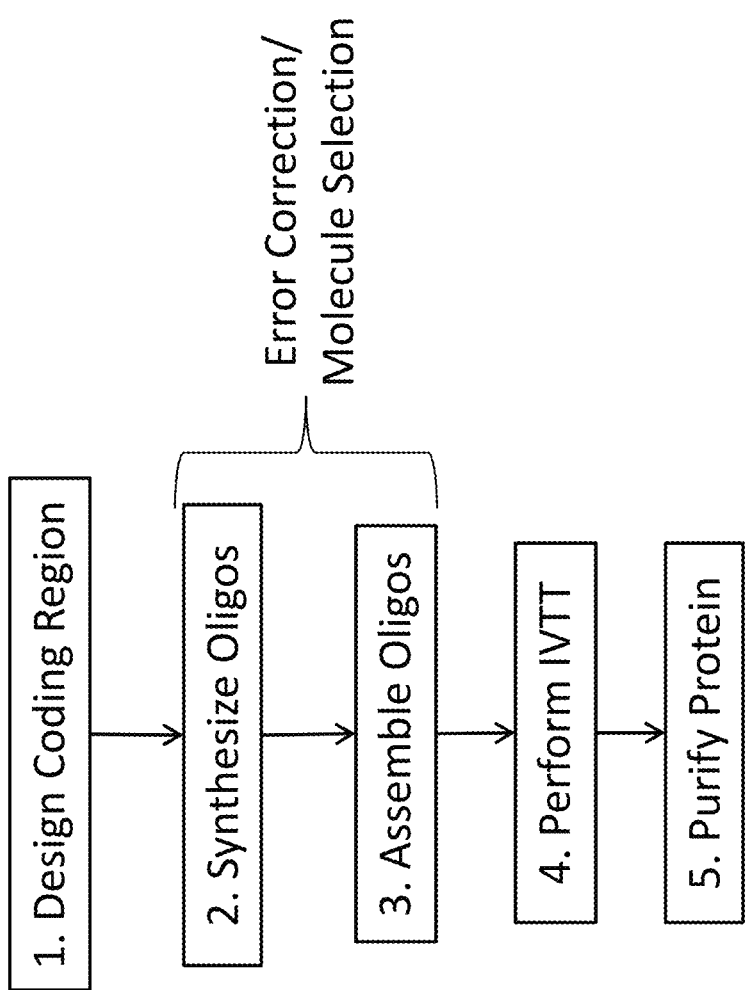
FIG. 1 shows a diagrammatic overview of some aspects of work flows of the invention.

Definitions:

As used herein the term "in vitro transcription and trans-lation (IVTT)" refers the generation of messenger RNA (mRNA) molecules and the production of proteins from these mRNA molecules. Typically, IVTT will employ cel-lular extracts that contain transcription and translation "machinery" (e.g., ribosomes, tRNA synthetases, charged and uncharged tRNA molecules, RNA polymerases, etc.). These are cellular components capable of performing tran-scription and translation reactions. Together with transcrip-tion components that include T7 RNA polymerase and nucleotides, IVTT can be employed transcribe and translate genes that are supplied in the form of a purified DNA molecule. Cellular components used in IVTT reactions may obtained for essentially any cell type and may be supple-mented with various reagents (e.g., buffers, amino acids, tRNA molecules, etc.).

IVTT reactions are composed of two sub-components: (1) "in vitro transcription" (IVTr) and (2) "in vitro translation" (IVTl). These processes may occur in a single reaction mixture or may be performed in separate reaction mixtures.

As used herein, the term "preferred codon" refers to the most prevalent codon for a particular amino acid used in naturally occurring protein coding nucleic acids within an organism. These codons will not necessarily correlate with the intracellular abundance of tRNA molecules with the cognate anti-codon or translational efficiency.

As used herein, the term "nucleic acid" refer to polyde-oxyribonucleotides (containing 2-deoxy-D-ribose) "DNA", polyribonucleotides (containing D-ribose) "RNA", and to any other type of polynucleotide that is an N glycoside of a purine or pyrimidine base. This term refer only to the primary structure of the molecule. Thus, these double- and single-stranded DNA, as well as double- and single-stranded RNA are included. Further included are linear and circular DNA and RNA. For use in the present invention, a nucleic acid molecule can comprise nucleotide analogs in which the base, sugar or phosphate backbone is modified as well as non-purine or non-pyrimidine nucleotide analogs.

The term "oligonucleotide," as used herein, also refers to DNA and RNA, and to any other type of polynucleotide that is an N-glycoside of a purine or pyrimidine base but will typically be DNA. Oligonucleotides are thus a subset of nucleic acid molecules and will be DNA and single-stranded. Oligonucleotides are less than 100 nucleotides in length. Thus, primers will generally fall into the category of oligonucleotide.

Oligonucleotides can be prepared by any suitable method, including direct chemical synthesis by a method such as the phosphotriester method of Narang et al., *Meth. Enzymol.* 68:90-99 (1979); the phosphodiester method of Brown et al., *Meth. Enzymol.* 68:109-151 (1979); the diethylphosphora-midite method of Beaucage et al., *Tetrahedron Letters* 22:1859-1862 (1981); and the solid support method of U.S. Pat. No. 4,458,066, each incorporated herein by reference. A review of synthesis methods of conjugates of oligonucle-otides and modified nucleotides is provided in Goodchild, *Bioconjugate Chemistry* 1:165-187 (1990).

The term "primer," as used herein, refers to an oligo-nucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is generally composed of single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)$_n$ sequence, where n is in the range from about 20 to about 200). The region of the primer that is sufficiently complementary to the template to hybridize is referred to herein as the hybridizing region.

The term "promoter" refers to a cis-acting DNA sequence that directs RNA polymerase and other trans-acting transcription factors to initiate RNA transcription from the DNA template that includes the cis-acting DNA sequence.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

As used herein, "translation template" refers to an RNA product of transcription from an expression template that can be used by ribosomes to synthesize polypeptide or protein.

As used herein, the term "cap" (or "5'-cap") refers to a chemical modification of the 5'-terminus of a translation template. A cap for eukaryotic translation templates can include a guanine nucleotide connected to the mRNA via a 5' to 5' triphosphate linkage ("5',5'-GpppG" or "G(5')ppp(5') G"). The N-7 position guanine cap can methylated ("m$^7$GpppG" or "m$^7$G(5)ppp(5')G"). Translation templates that include cap can be designated by 5',5'-GpppG-, G(5') ppp(5')G-, m$^7$G(5')ppp(5')G- or m$^7$GpppG-translation templates.

As used herein, "cap-dependent," as the term modifies "translation" or "translation template," refers to the requirement of the translation template to include a 5'-cap for efficient protein synthesis from that translation template.

As used herein, "cap-independent," as the term modifies "translation" or "translation template," refers to the lack of a requirement that the translation template include a 5'-cap for efficient protein synthesis from that translation template.

As used herein, "GC content," as the term modifies "nucleic acids," refers to the average number of bases or base pairs that are either guanine or cytosine. For example, if a double-stranded DNA molecule is 100 base pairs in length and has 60 G-C base pairs and 40 A-T base pairs, the DNA molecules has a GC content of 60%.

As used herein, the term "solid support" refers to a porous or non-porous material on which polymers such as nucleic acid molecules can be synthesized and/or immobilized. As used herein "porous" means that the material contains pores which may be of non-uniform or uniform diameters (for example in the nm range). Porous materials include paper, synthetic filters, etc. In such porous materials, the reaction may take place within the pores. The solid support can have any one of a number of shapes, such as pin, strip, plate, disk, rod, fiber, bends, cylindrical structure, planar surface, concave or convex surface or a capillary or column. The solid support can be a particle, including bead, microparticles, nanoparticles and the like. The solid support can be a non-bead type particle (e.g., a filament) of similar size. The support can have variable widths and sizes. For example, sizes of a bead (e.g., a magnetic bead) which may be used in the practice of the invention are described elsewhere herein. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers such as filter paper, chromatographic paper or the like. The support can be immobilized at an addressable position of a carrier. The support can be loose (such as, e.g., a resin material or a bead in a well) or can be reversibly immobilized or linked to the carrier (e.g. by cleavable chemical bonds or magnetic forces etc.).

In some embodiments, solid support may be fragmentable. Solid supports may be synthetic or modified naturally occurring polymers, such as nitrocellulose, carbon, cellulose acetate, polyvinyl chloride, polyacrylamide, cross linked dextran, agarose, polyacrylate, polyethylene, polypropylene, poly (4-methylbutene), polystyrene, polymethacrylate, poly (ethylene terephthalate), nylon, poly(vinyl butyrate), polyvinylidene difluoride (PVDF) membrane, glass, controlled pore glass, magnetic controlled pore glass, magnetic or non-magnetic beads, ceramics, metals, and the like; either used by themselves or in conjunction with other materials.

In some embodiments, the support can be in a chip, array, microarray or microwell plate format. In many instances, a support generated by methods of the invention will be one where individual nucleic acid molecules are synthesized on separate or discrete areas to generate features (i.e., locations containing individual nucleic acid molecules) on the support.

15

Overview:

The invention relates, in part, to devices, compositions and methods related to the production of proteins from nucleic acid molecules, as well as production of the nucleic acid molecules themselves.

A starting point for the production of a protein is often the identification of the protein that one wishes to produce. Once that has occurred, the protein of interest may be produced and/or obtained by any number of means. For example, the protein of interest may be purified from a cell that either naturally expresses it or a cell that have been altered to express it (e.g., via insertion of an expression construct).

In many instances, once a protein that one wishes to produce is selected, a nucleic acid molecule encoding this protein will be either obtained from a natural source or synthesized For purposes of illustration, FIG. 1 shows an exemplary general workflow of the invention. In this exemplary work flow, once a protein of interest is selected for production, nucleic acid is designed that encodes the protein, oligonucleotides are then produced for assembly of the coding region, the oligonucleotides are then assembled to form the coding region, the assembled coding region is then used to generate RNA and ultimately protein from the RNA using an in vitro transcription/translation system. Of course, numerous variations of this exemplary work flow are possible. Further, the workflow may be entered or stopped at any point and materials may be removed at various points. As an example, if a coding region has already been prepared, then it can be introduced directly into step 4 of the workflow. Further, nucleic acid molecules may be removed from the workflow (e.g., for sequence verification, introduction into a vector, introduction into a cell, etc.) at or after step 3.

In many circumstances, when a protein is produced, the codon usage and the expression system are not important. However, in some instance, the codon usage and the expression system are important. For example, if the protein is post-translationally modified (e.g., glycosylated), then the expression may be important because different cells types are typically capable of generating proteins with different post-translational modifications.

Some aspects of the invention include the design of protein coding regions designed for ease of synthesis and efficient translation in an IVTT (and/or IVTr or IVTl) system, as well as the use of IVTT (and/or IVTr or IVTl) systems that allow for desired post-translational modifications. Additional aspects of the invention are directed to the automation of the in silico design of nucleic acid molecules, the production of these nucleic acid molecules, and/or the production of proteins using these nucleic acid molecules.

As explained herein, a number of advantageous features have been identified. One of these advantages is that more protein is typically generated in IVTT systems by nucleic acid molecules having codons optimized for the species from which the pool of tRNA for IVTT is sourced. For example, where tRNA was sourced from yeast, more protein was found to be generated in IVTT systems by nucleic acid molecules having codons optimized for expression in yeast cell as compared to codons optimized for mammalian cells, even when mammalian cell extracts are used for IVTT. Although any tRNA system and open reading frame codon-optimized for that tRNA system may be combined in methods and compositions of the invention, an advantage has been observed for those codon systems exhibiting a lower GC content. For example, using tRNA pools from yeast together with a yeast-optimized IVTT (and/or IVTl) template will typically result in a nucleotide composition with an average GC content below 55%, whereas mammalian-optimized open reading frames will typically have a higher GC content as described elsewhere herein. The GC content and more general, the base composition of a template used for IVTT (and/or IVTr or IVTl) may be critical for efficient assembly of the oligonucleotides as well as for subsequent in vitro transcription/translation which may have even larger implications or synergies where assembly and IVTT (and/or IVTr or IVTl) are combined in automated workflows as described herein. For example, oligonucleotides exhibiting a high GC content may comprise a high number of GC stretches or GC-rich repetitive regions which may cause mis-hybridization or interfere with PCR-based assembly. Furthermore, open reading frames with high GC content may exhibit a high level of secondary structures in transcribed RNA molecules which may interfere with subsequent translation thereby decreasing the entire IVTT (and/or IVTr or IVTl) workflow efficiency. It is therefore an aim of the invention to provide nucleic acid templates (e.g., linear templates or closed-circular templates, etc.) for IVTT (and/or IVTr or IVTl) that are 1) efficiently assembled and 2) efficiently in vitro-transcribed and translated in the context of a given IVTT/tRNA system.

Coding Region Design and Design Considerations

Often, one of the first steps in producing a nucleic acid molecule or protein of interest after the molecule(s) has been identified is nucleic acid molecule design. A number of factors go into design of the coding region and the oligonucleotides used to generate the coding region. These factors include one or more of the following: (1) the AT/GC content of all or part of the nucleic acid molecule (e.g., the coding region, (2) the presence or absence of restriction endonuclease cleavage sites (including the addition and/or removal of restriction sites), (3) preferred codon usage for the particular protein production system that is to be employed, (4) junctions of the oligonucleotide being assembled, (5) the number and lengths of the oligonucleotides used to produce the coding region, (6) minimization of undesirable regions (e.g., "hairpin" sequences, regions of sequence homology to cellular nucleic acids, repetitive sequences, etc.) and (7) coding region flanking segments that may be used for attachment of 5' and 3' components (e.g., restriction endonuclease sites, recombination sites, etc.).

In many instances, parameters will be input into a computer and software will generate an in silico nucleotide sequence that balances the input parameters. The software may place "weights" on the input parameters in that, for example, what is considered to be a nucleic acid molecule that closely matches some of the input criteria may be difficult or impossible to assemble. Exemplary nucleic acid design methods are set out in U.S. Pat. No. 8,224,578.

One main aspect of nucleic acid molecule design is the probability that the nucleic acid molecule can be produced in a "single-run". Put another way, the probability that a particular synthesis and assembly cycle will result in the generation of the designed nucleic acid molecule. This may be estimated by the use of data derived from past synthesis and assembly cycles and characteristics of the designed nucleic acid molecules. One factor that results in some synthesis assembly failures is high GC content. A number of nucleic acid design parameters are set out in Fath et. al., *PLoS One,* 6:e17596 (2011).

Further, nucleic acid molecules design factors may be considered across the length of the nucleic acid molecule or in specific regions for the molecule. For example, GC content may be limited across the length of the nucleic acid molecule to prevent synthesis "failures" resulting from specific locations within the molecule. Thus, synthesizability of the nucleic acid molecule is a characteristic of the entire nucleic acid molecule in that a regional "failure to assemble" results in the designed nucleic acid molecule not being assembled. From a regional perspective, codon may be selected for optimal translation but this may conflict with, for example, region limitation of GC content.

Assembly success often involves multiple parameters and regional characteristics of the desired nucleic acid molecule. Total and regional GC content is only one example of a parameter. For example, the total GC content of a nucleic acid molecule may be 50% but the GC content in a particular region of the same nucleic acid molecule may be 75%. Thus, in many instances, GC content will be "balanced" across the entire nucleic acid molecule and may vary regionally by less than 15%, 10%, 8%, 7%, or 5% from the total GC content.

When assessing regional GC content, the length of the region needs to be considered. As an example, there is only one codon for the amino acid methionine (ATG). Thus, if a region of three nucleotides is considered and the three nucleotide "region" is a methionine codon, then the GC content is 33.3%. If the total GC content is 50%, the methionine codon varies by 16.6% from the total GC content. For this reason, when regional GC content is assessed, the region is often of a length that is at least 8%, 10% or 15% of either the total length of the nucleic acid molecule or the total length of the coding region (when present).

Assume for purposes of illustration that a nucleic acid molecule that is 1,000 nucleotides in length is generated, containing no introns, and that it encodes a protein that is 285 amino acids in length. The coding region is 855 nucleotides in length (not including the stop codon). Also assume that there are 100 nucleotides 5' to the coding region and 42 nucleotides 3' to the coding region. 10% of the total entire nucleic acid molecule is 100 nucleotides and 10% of the coding region is 85.5 nucleotides. Thus, in this instance, the phrase "at least 10% of the coding region" encompasses a region of 86 or more nucleotides.

Figure 5A:
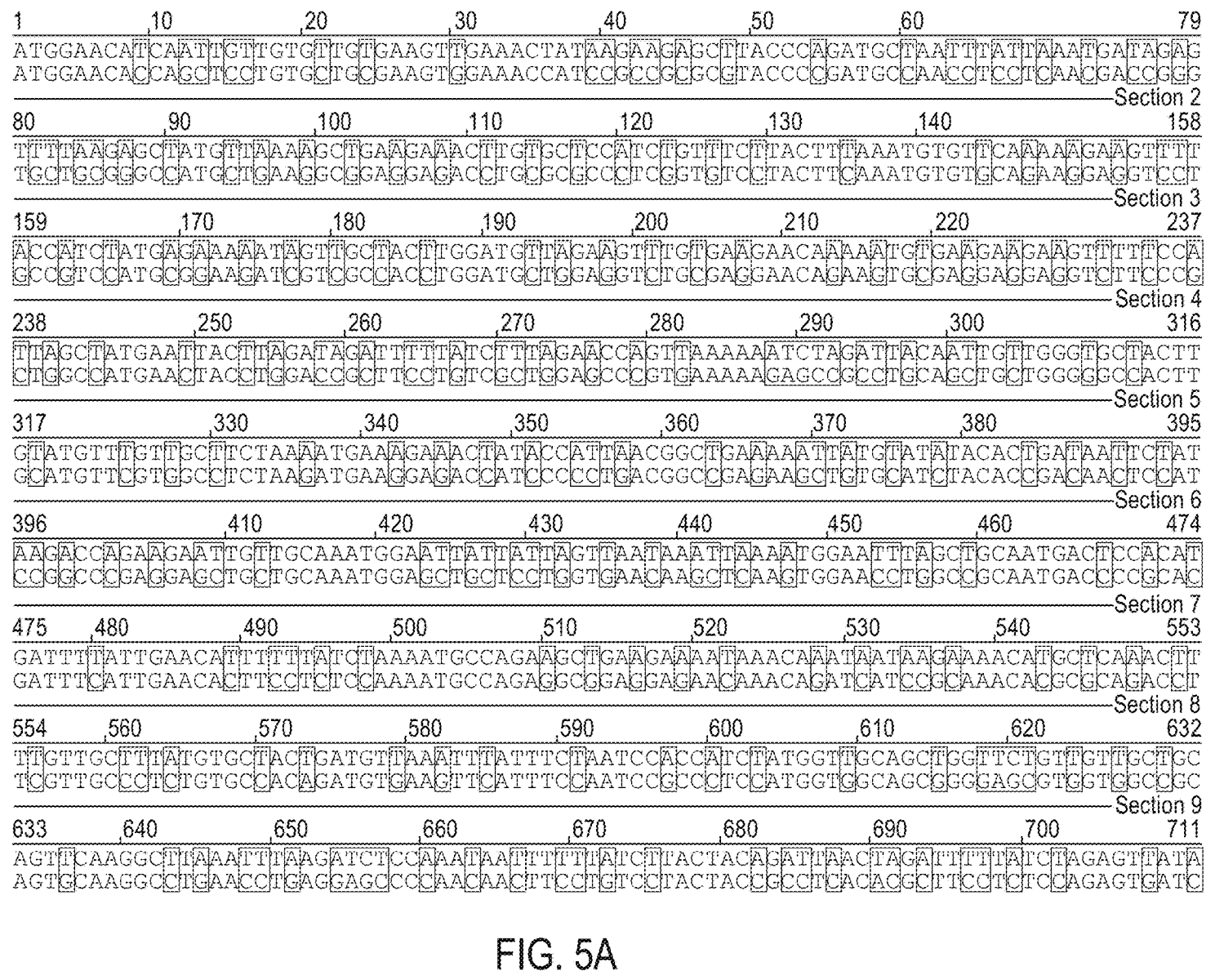
Figure 5B:
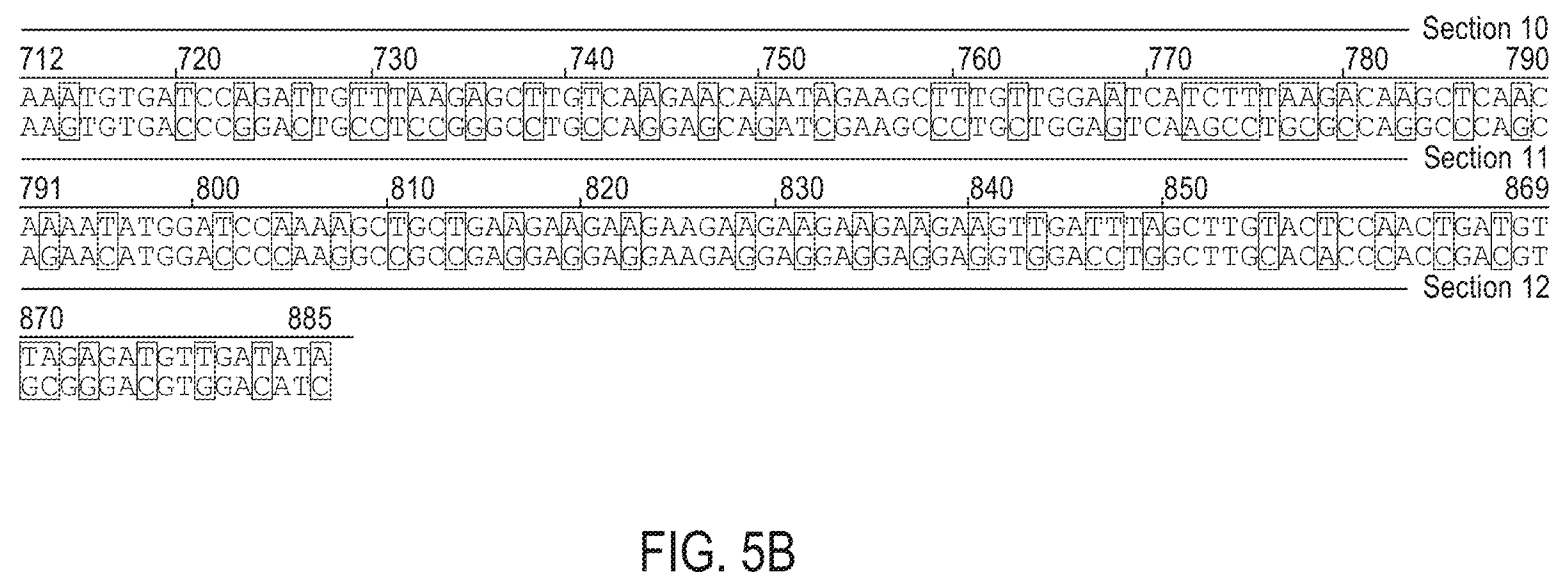
Figure 6:
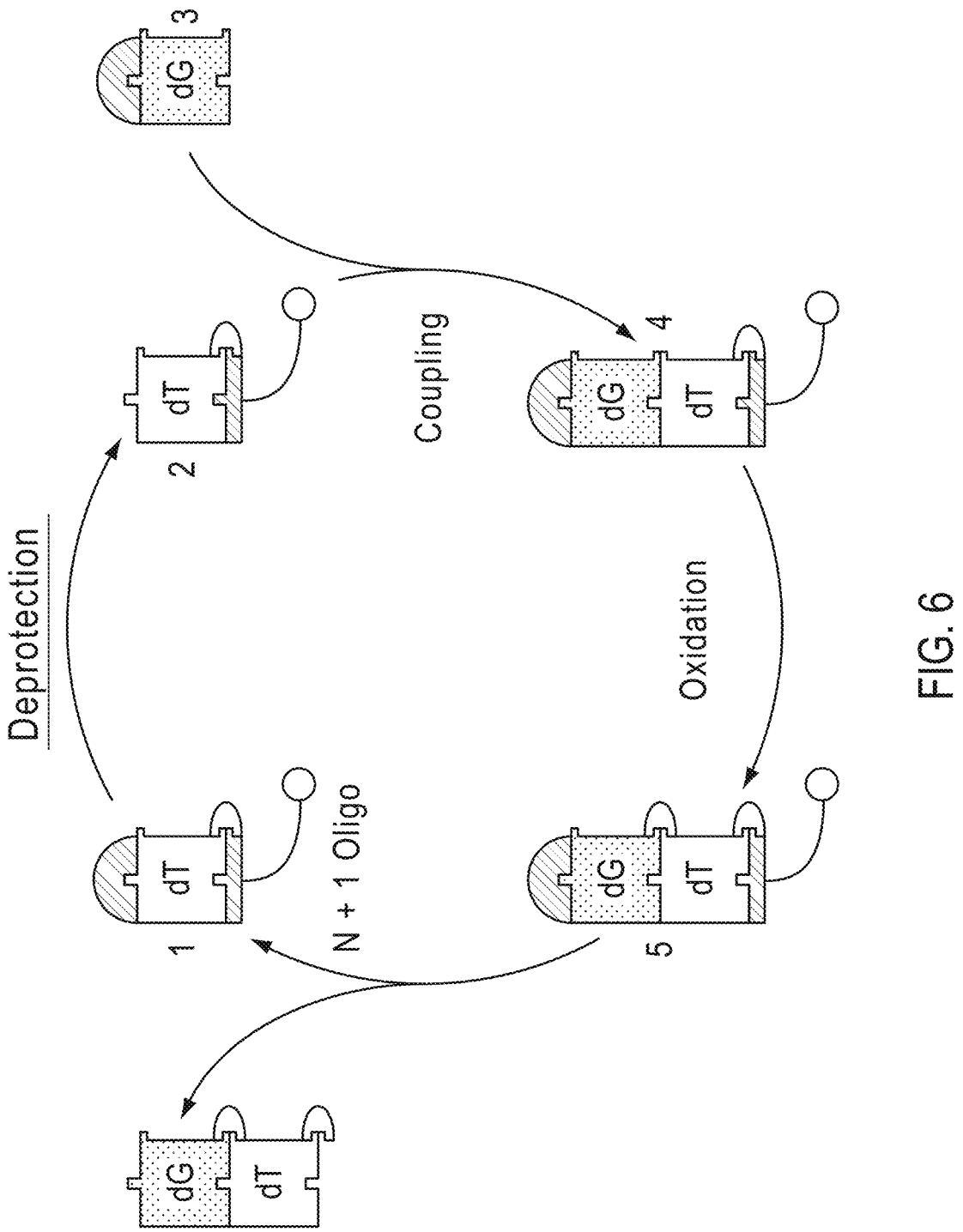
FIG. 6 nucleic acid synthesis process. Compound 1 is composed of deoxythymidine linked to a solid support (the small shaded circle). The half-circle on the top of Compound 1 is a protecting group that prevents the addition of bases. Compound 1 undergoes a deprotection step that removes the protecting group to form Compound 2. Compound 3, deoxyguanosine that also contains a protecting group, is coupled to Compound 2 to form Compound 4. Compound 4 is then oxidized to for a phosphodiester bond (shown as the small sideways half circle) between the two bases thereby forming Compound 5. In this figure Compound 5 is then released from the solid support. However, this cycle may be repeated to produce longer oligonucleotides with a desired nucleotide sequence.

For purposes of illustration, the wild-type human CCND1 coding region is shown in FIGS. 5A and 5B. This coding region has been divided into nine regions and eight regions of 100 nucleotides and one region of 85 nucleotides. The eight regions of 100 nucleotides vary in GC content from 54.0% to 64.0% and one region of 85 nucleotides has a GC content of 68.2%. Thus, the 100 nucleotide regions show an 11% variation. FIG. 6 shows a yeast codon optimized version of the same coding sequence. In this instance, the eight regions of 100 nucleotides vary in GC content from 24.0% to 32.0% and one region of 85 nucleotides has a GC content of 35.3%. Thus, the 100 nucleotide regions show an 8% variation. These two codon regions have a difference in 100 nucleotide region GC content of about 27% (8/11=72.7, 72.7−100=27.3%). The invention thus includes the preparation and use of codon regions where regions GC content (e.g., over 100 nucleotide regions) are decreased by at least 5%, 10%, 15%, 20%, 25% or 30%.

The invention also includes nucleic acid molecules where the GC content varies by no more than 10% across the total length of the nucleic acid molecule or regions of the total nucleic acid molecule or the coding region, wherein the regions comprise at least 10% of either the total length of the nucleic acid molecule or the total length of the coding region.

Further, the designed nucleic acid molecule may be based upon a naturally occurring nucleic acid molecule and modifications are made to the naturally occurring to enhance synthesizability. In some instances, naturally occurring nucleic acid molecules are not considered in the production of a coding region and only synthesis and expression factors are used in the design process.

A synthetic gene ought therefore to be optimized in relation to the codon usage and the GC content and, on the other hand, substantially avoid the problems associated with DNA motifs and sequence repeats and inverse complementary sequence repeats. These requirements cannot, however, ordinarily be satisfied simultaneously and in an optimal manner. When a limited set of codons is used, often the repetitive nature of a coding sequence increases. Thus, alteration of a coding sequence to what is considered preferred codon usage may lead to a highly repetitive sequence and a considerable difference from the desired GC content. As an example, the low GC content nucleotide sequence shown in FIG. 4 contains the sequence AAAT seventeen times and the wild-type sequence shown in FIG. 3 contains this sequence only twice. Further, coding regions designed to have either low GC or high GC content will exacerbate this problem by limiting the codons used by base type.

The aim therefore is to reach a compromise which is as optimal as possible between satisfying the various requirements. However, the large number of amino acids in a protein leads to a combinatorial explosion of the number of possible DNA sequences which—in principle—are able to express the desired protein. For this reason, various computer-assisted methods have been proposed for ascertaining an optimal codon sequence. Further factors which may influence the result of expression are DNA motifs and repeats or inverse complementary repeats in the base sequence. Certain base sequences produce in a given organism certain functions which may not be desired within a coding sequence. Examples are cis-active sequence motifs such as splice sites or transcription terminators. The presence of a particular motif may reduce or entirely suppress expression or even have a toxic effect on the host organism. Sequence repeats may lead to lower genetic stability and impede the synthesis of repetitive segments owing to the risk of incorrect hybridizations. Inverse complementary repeats may lead to the formation of unwanted secondary structures at the RNA level or cruciform structures at the DNA level, which impede transcription and lead to genetic instability, or may have an adverse effect on translation efficiency.

Repetitive sequence segments may, for example, lead to low genetic stability. The synthesis of repetitive segments is also made distinctly difficult because of the risk of faulty hybridization. Therefore, the assessment of a test sequence includes whether it comprises identical or mutually similar sequence segments at various points. The presence of corresponding segments can be established for example with the aid of a variant of a dynamic programming algorithm for generating a local alignment of the mutually similar sequence segments. Such an algorithm is set out in U.S. Patent Publication No. 2007/0141557. Typically, to calculate the criterion weight relating to the repetitive elements, the individual weights of all the local alignments where the alignment weight exceeds a certain threshold value are summed. Addition of these individual weights gives the criterion weight which characterizes the repetitiveness of the test sequence.

Inverse complementary repeats present the potential formation of secondary structures and the RNA level or cruciform structures at the DNA level can be recognized on the test sequence by the presence of such inverse complementary repeats (inverse repeats). Cruciform structures at the DNA level may impede translation and lead to genetic instability. Further, the formation of secondary structures at the RNA level may have adverse effects on translation efficiency. In this connection, inverse repeats of particular importance are those which form hairpin loops or cruciform structures. Faulty hybridizations or hairpin loops may also have adverse effects in the synthesis of the former from oligonucleotides. As an example, the low GC content nucleotide sequence shown in FIG. 4 contains the sequence AAAAA five times and the wild-type sequence shown in FIG. 3 contains this sequence only once. Further, the nucleotide sequence shown in FIG. 4 contains the sequence TTTTT five times and the wild-type sequence shown in FIG. 3 does not contain this sequence.

Typically, nucleic acid molecules will be designed to have an estimated and/or actual synthesis and assembly cycle success rate of at least 90% (e.g., from about 90% to about 99.5%, from about 92% to about 99.5%, from about 93% to about 99.5%, from about 94% to about 99.5%, from about 95% to about 99.5%, from about 90% to about 98%, from about 92% to about 98%, from about 93% to about 98.5%, from about 94% to about 98.5%, etc.).

As noted herein one important feature of the coding region is codon usage. Codon usage varies with a number of factors, including the particular organism and the type of gene being expressed within that organism. For example, it has been found in both Drosophila and Caenorhabditis that codon bias plays a major role in the selection of highly expressed genes. Further, "optimal" codons typically correspond to the tRNA molecules that are most abundant in a cell. These observations support the translation selection hypothesis which states that codon usage has been shaped by selection to improve the efficiency of translation of certain proteins. Thus, protein expression levels within cells appear to be partly controlled by the codons of the particular gene. Also, expression efficiency is also thought to increase with the use of preferred codons for a particular cell type and there is evidence that low-frequency-usage codons within a coding sequence provides for genetic instruction that regulates the rate of protein synthesis. (Reviewed in Angov, "Codon usage: Nature's roadmap to expression and folding of proteins, "Biotechnol. J., 6:650-659 (2011).)

Codon usage may be adjust across a coding region and/or in portions of coding regions to match desired codons, as set out elsewhere herein. In many instances, this will be done while maintaining a desired level of synthesizability.

As set out elsewhere herein, the invention includes compositions and methods for the production of protein from mRNA molecules. In some instances, the amount of protein produced per unit amount of mRNA is substantially increased over many prior protein expression methods (see FIG. 15). The increased production of protein ties, in part, to the tailoring of the codon usage in the coding region to in vitro translation system that is used. As such, the coding region may be designed to "match" features of the in vitro translation system used.

From Tables 14 and 15, it can be seen that in E. coli the most commonly used codons for the following amino acids are as follows TGC for Cys, CGG and CGT for Arg, CCG for Pro, CTG for Leu, and GCC for Ala and in S. cerevisiae the most commonly used codons for the following amino acids are as follows TGT for Cys, AGA for Arg, CCA for Pro, TTA and TTG for Leu, and GCT for Ala. The preferred codons for these amino acids have a higher GC content in E. coli than they do in S. cerevisiae. Table 15 elaborates on this point by comparing the preferred codons of humans, S. cerevisiae, and E. coli.

As can be seen, the GC content of the preferred codons for (1) human cells is about 63%, (2) S. cerevisiae is about 30%, (3) Pichia pastoris is about 37%, and (4) E. coli is about 53%. Further, as shown in Table 16, there are three human and E. coli codons that contain three G and/or C bases, where the same codons in yeast contain no G or C bases. In fact, no preferred yeast codons set out in Table 15 contain three G and/or C bases and only two preferred yeast codons contain two G and/or C bases. The average GC content of the preferred yeast codons is 30% (assuming each codon is used once to generate a twenty amino acid polypeptide).

In some embodiments of the invention, codon usage is determined by balancing the AT/GC content of a nucleic acid molecule with the use of codons that are preferred for the IVTT (and/or IVTl) system. Further, low GC codons may be selected to enhance the amount of protein produced in IVTT systems, even when the transcription and translation "machinery" is obtained from cells that typically have preferred codons with higher GC content.

Nucleic Acid Synthesis

A number of methods for synthesizing oligonucleotides are known. In many instances, oligonucleotide synthesis is performed by a stepwise addition of nucleotides to the 5'-end of the growing chain until oligonucleotides of desired length and sequence are obtained. Further, each nucleotide addition can be referred to as a synthesis cycle (see FIG. 6) and often consists of four chemical reactions: (1) De-Blocking/De-Protection, (2) Coupling, (3) Capping, and (4) Oxidation. One example of chemical oligonucleotide synthesis chemical processes is set out below.

Nucleic acid synthesis typically starts with selection of synthesis components or "building blocks" used to produce oligonucleotides. Often 3'-O—(N,N-diisopropyl phosphoramidite) derivatives of nucleosides (nucleoside phosphoramidites) are used as building blocks in phosphite triester methodologies. To prevent undesired side reactions, all other functional groups present in the nucleosides are normally rendered unreactive (protected) by the attachment of protecting groups. Upon oligonucleotide synthesis completion, remaining protecting groups are removed to yield the desired oligonucleotides free of protein groups.

5'-hydroxyl groups are often protected by an acid-labile DMT (4,4'-dimethoxytrityl) group. Phosphite group are often protected by a base-labile 2-cyanoethyl group.

De-blocking/De-protection: DMT groups are often removed with a solution of one or more acid, such as trichloroacetic acid (TCA) or dichloroacetic acid (DCA), present in an inert solvent (dichloromethane or toluene), resulting in the solid support-bound oligonucleotide precursor bearing a free 5'-terminal hydroxyl group. A washing step typically follows.

Coupling: In an exemplary process, a solution of nucleoside phosphoramidite in acetonitrile is activated by a solution of an acidic azole catalyst (e.g., 1-H-tetrazole, 2-ethylthiotetrazole, 2-benzylthiotetrazole, or 4,5-dicyanoimidazole) and then brought in contact with the solid support where free 5'-hydroxy group reacts with the activated phosphoramidite moiety of the incoming nucleoside phosphoramidite to form a phosphite triester linkage. The coupling reaction of 2'-deoxynucleoside phosphoramidites is rapid and goes to near completion in about 20 seconds. Upon the completion of the coupling, unbound reagents and by-products are typically removed by washing.

Capping: Typically, after the completion of the coupling reaction, a small percentage (generally in the range of 0.1 to 1%) of the solid support-bound 5'-OH groups is unreacted and must be permanently blocked from further chain elon- gation so as to prevent the formation of oligonucleotides with an internal base deletion commonly referred to as (n–1) shortmers. Unreacted 5'-hydroxy groups are, to a large extent, acetylated by the capping mixture. Capping steps are often performed by treating the solid support-bound material with a mixture of acetic anhydride and 1-methylimidazole.

Oxidation: The newly formed tricoordinated phosphite triester linkage typically formed by chemical synthesis is not natural and is relatively unstable. Treatment with reagents containing iodine and water in the presence of a weak base (e.g., pyridine, lutidine, or collidine) oxidizes the phosphite triester linkage into a tetracoordinated phosphate triester, which is a protected precursor of naturally occurring phosphodiester internucleosidic linkages.

Once synthesis of nucleic acid molecules is complete, these molecules are typically released from the solid support. The method of release is often specific for the linking group through which the oligonucleotide is linked to the solid support. The linker may have a specific base attached as the starting base of the oligonucleotide (a universal support). In such instances, a solid support (e.g., once having a dA, dT, dC, dG, or dU) is selected based upon the starting base of the oligonucleotide being synthesized. In many instances, the oligonucleotide is cleaved from the solid support using gaseous ammonia, aqueous ammonium hydroxide, aqueous methylamine, or mixtures thereof.

After completion of oligonucleotide synthesis reactions, support-associated (e.g., solid support-associated) oligonucleotides may be subject to further processing. For example, individual solid supports may be pooled; the oligonucleotide may cleaved from the solid support using, for example, gaseous ammonia, aqueous ammonium hydroxide, aqueous methylamine, or mixtures thereof, followed by assembly to form larger nucleic acid molecules.

In some embodiments of the invention, nucleic acid molecules are attached to the solid support (e.g., a magnetic or non-magnetic bead) via succinyl groups. In certain embodiments, a universal linker may be located between the succinyl group and the nucleic acid molecules. The succinyl linker may be cleaved by the use of, for example, concentrated aqueous ammonium hydroxide. The reaction is usually carried out at temperatures between 50° C. and 80° C. for at least one to about eight hours. In certain embodiments, the succinyl linker may be cleaved by the use of ammonia gas, using increased heat and pressure, such as, for example, a temperature of about 80° C., and a pressure of about 3 bars for a time of about 2 hours.

Depending on the nucleic acid molecule to be assembled, the number of solid supports that may be pooled prior to release of synthesize nucleic acid molecules may vary widely and includes from about 10 to about 50, from about 50 to about 100, from about 100 to about 1000, from about 50 to about 10,000, from about 100 to about 10,000, or from about 500 to about 10,000 individual supports. In some instances, nucleic acid molecules will be release form synthesis supports and then pooled as unbound nucleic acid molecules.

A number of variations to the oligonucleotide synthesis process may be made. For example, electrochemically generated acid (EGA) or photogenerated (PGA) may be used to remove the protecting group (e.g., DMT) before the next amidite is added to the nucleic acid molecule attached to the solid support. In some embodiments, at least one proton carrier, such as 2-chloro-6-methylpyridine or diphenylamine, may be present in the solution with the EGA or PGA. The at least one proton carrier may act to reduce the effect of DNA degradation by accepting protons from the EGA or PGA, thereby adjusting the acidity of the solution.

EGA and PGA deprotection reagents and methods for generating such acids, as well as their use in oligonucleotide synthesis are set out in U.S. Appl. No. 62/145,359, filed Apr. 9, 2015, the entire disclosure of which is incorporated herein by reference.

While in many instances oligonucleotides may be produced using phosphoramidite synthesis chemistry, as well as variations thereof, other methods may also be used to produce oligonucleotides, including PCR, restriction enzyme digest, exonuclease treatment, or template-independent synthesis using a nucleotidyl transferase enzyme. Exemplary methods of template-independent synthesis using a nucleotidyl transferase enzyme are set out in U.S. Pat. No. 8,808,989. The nucleotidyl transferase enzyme (e.g., terminal deoxynucleotidyl transferase) is used to incorporate nucleotide analogs having an unmodified 3' hydroxyl and a cleavable protecting group. Because of the protecting group, synthesis pauses with the addition of each new base, whereupon the protecting group is cleaved, leaving a polynucleotide that is essentially identical to a naturally occurring nucleotide (i.e., is recognized by the enzyme as a substrate for further nucleotide addition). Thus, in certain embodiments, the invention includes methods in which oligonucleotides are produced by enzymatic reaction.

Nucleotide triphosphates (e.g., deoxynucleotide triphosphates) (NTPs) suitable for use with enzymatic oligonucleotide synthesis methods will have protecting groups that do not prevent the NTPs from being used by a nucleotidyl transferase as a substrate and can be efficiently removed to allow for addition to an oligonucleotide chain. Thus, in certain embodiments, the invention includes methods where nucleotide addition occurs via enzymatic reaction. In some instances, EGA is generated as part of the deprotection process. Further, in certain instances, all or part of the oligonucleotide synthesis reaction may be performed in aqueous solutions. In other instances, organic solvents will be used.

Nucleic Acid Assembly and Error Correction

Once the chemical synthesis phase has been completed, the resulting nucleic acid molecules will typically be assembled into larger nucleic acid molecules. The final product nucleic acid may be a composite in the sense that all of the components are synthesized and assembled or only some of the components are synthesized and these components are then assembled with other nucleic acid molecules (e.g., nucleic acid molecules generated by PCR or propagated within cells). Using the DNA molecule shown in FIG. 12 for purposes of illustration, the coding region (labeled "Gene of Interest") may be chemically synthesized and then connected to the other nucleic acid components shown.

Figure 12:
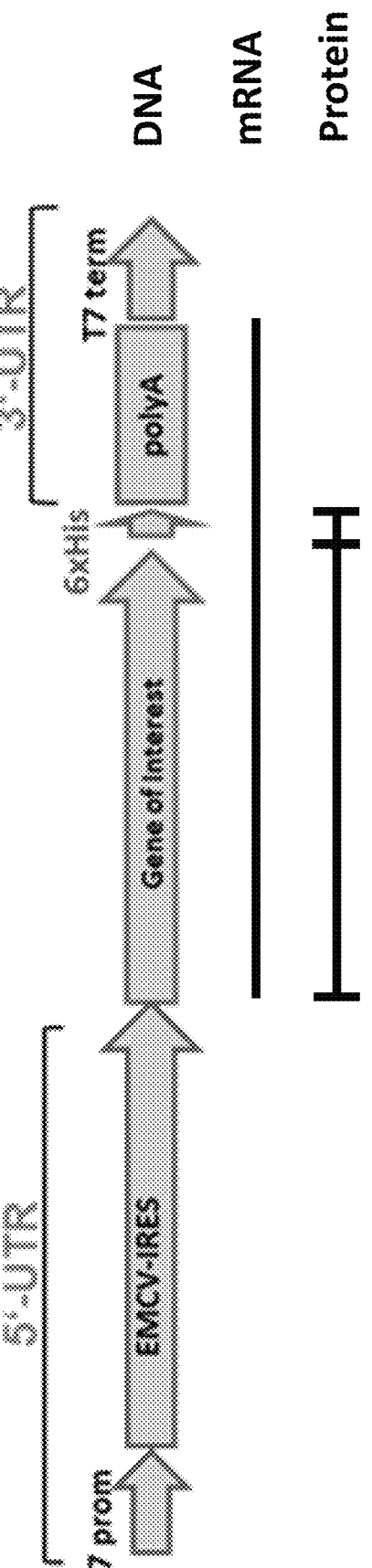
FIG. 12 is an expression cassette generated by and used in methods of the invention. The 5' untranslated region (UTR) contains a T7 promoter and encodes an encephalomyocarditis virus internal ribosome entry site (EMCV-IRES). The coding region is labeled "Gene of Interest" and is shown as encoding a six histidine tag (SEQ ID NO: 3). The 5' untranslated region (UTR) encodes a polyA tail for the mRNA that is to be transcribed and T7 polymerase terminator. A line is shown below the DNA region that indicates the portions of the DNA molecule that are transcribed to form the mRNA molecule. The line at the bottom of the figure represents the protein translation products, including the carboxyl histidine tag.
Figure 13A:
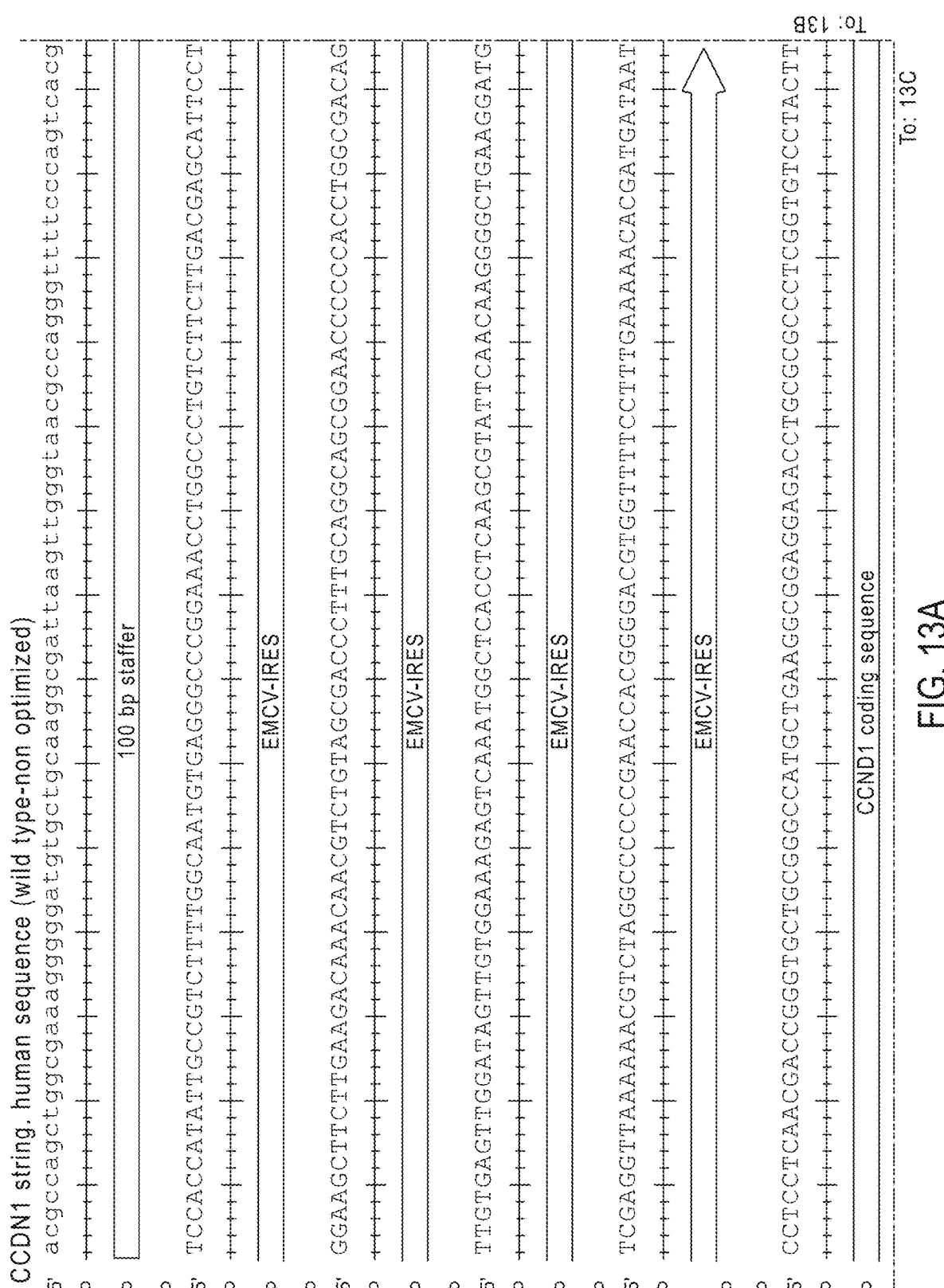
FIG. 13A-13D shows the nucleotide sequences of the 5'- and 3'-UTRs set out in FIG. 12 (SEQ ID NO: 9).
Figure 13B:
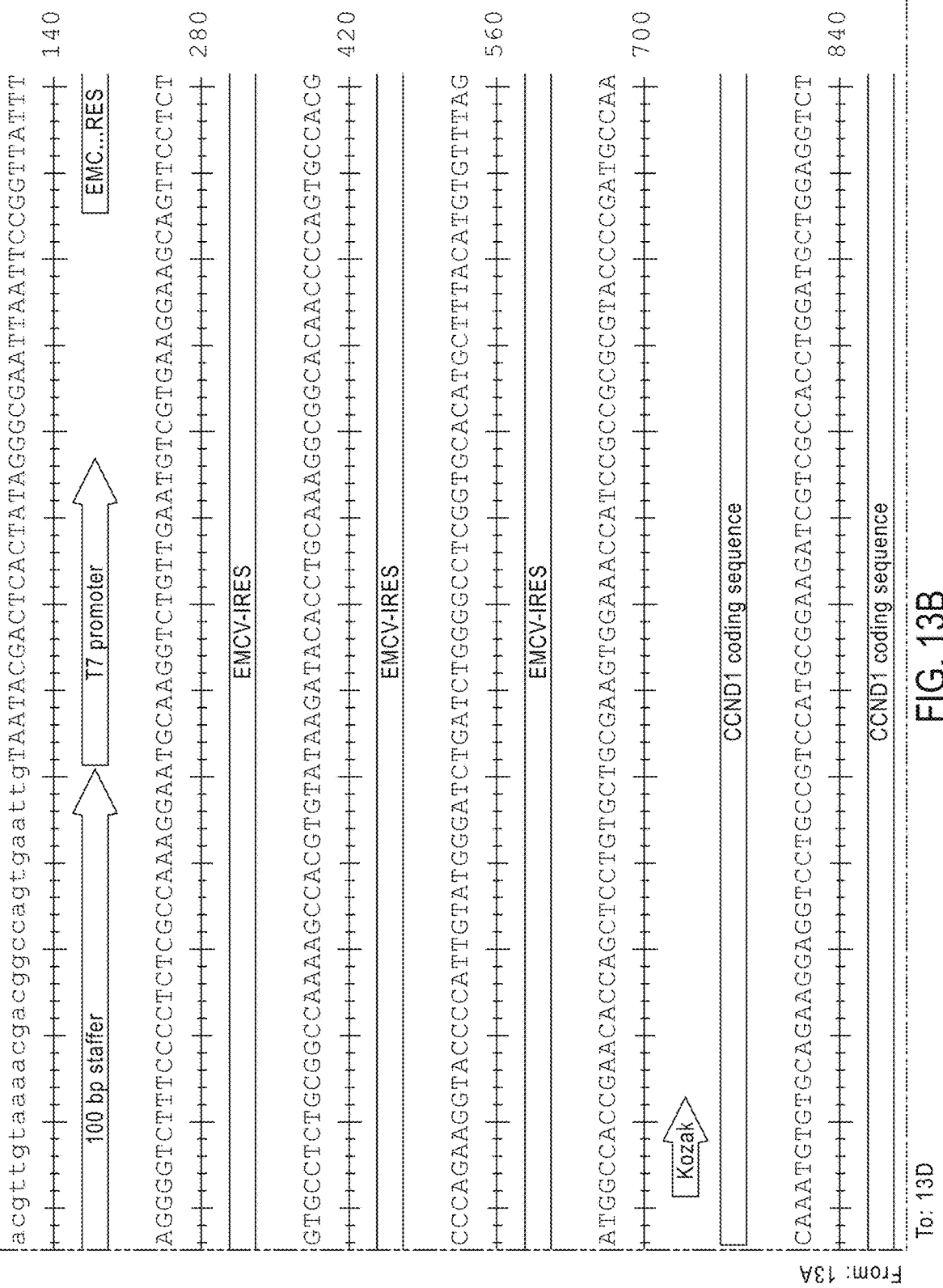
Figure 13C:
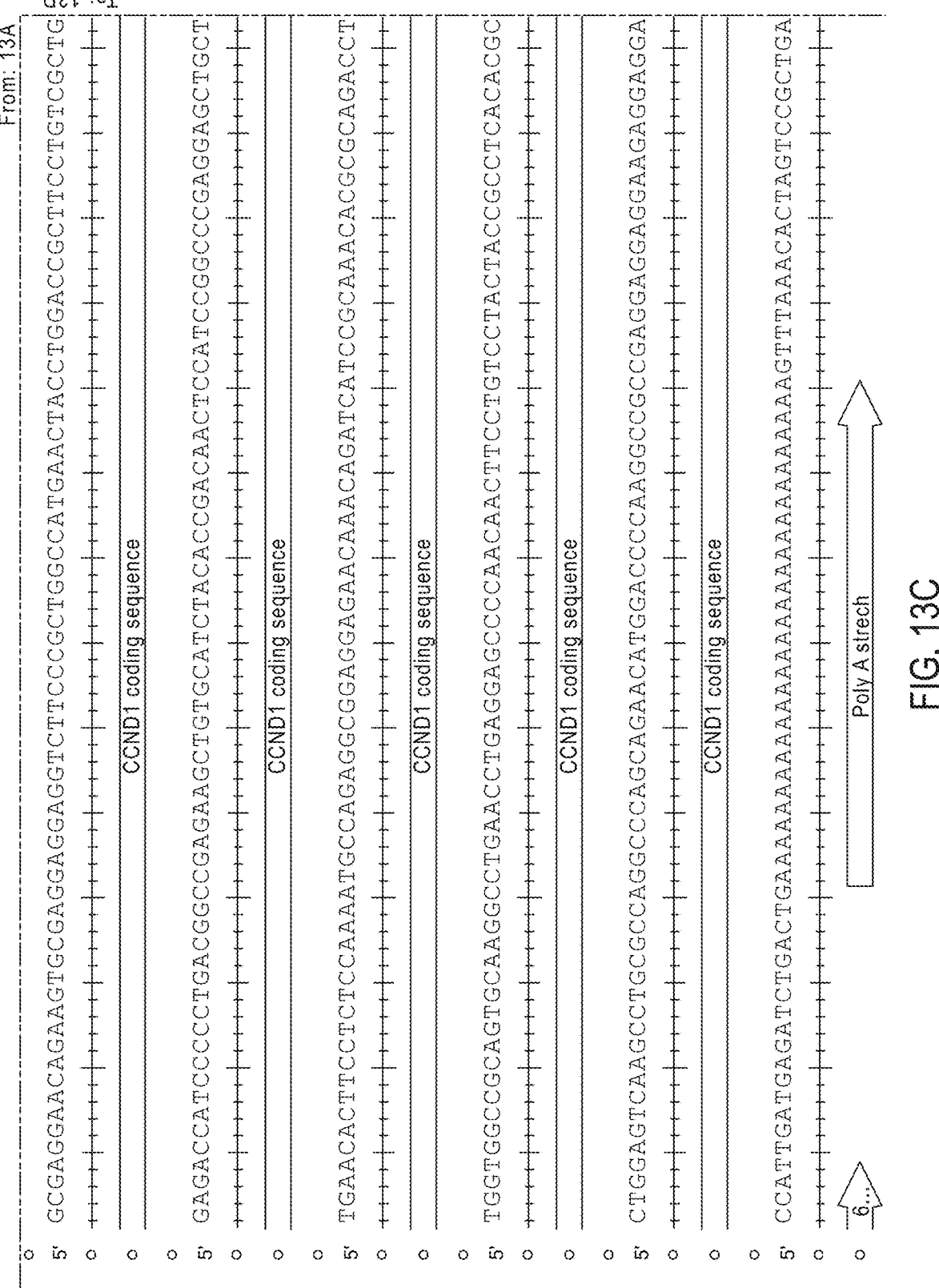
Figure 13D:
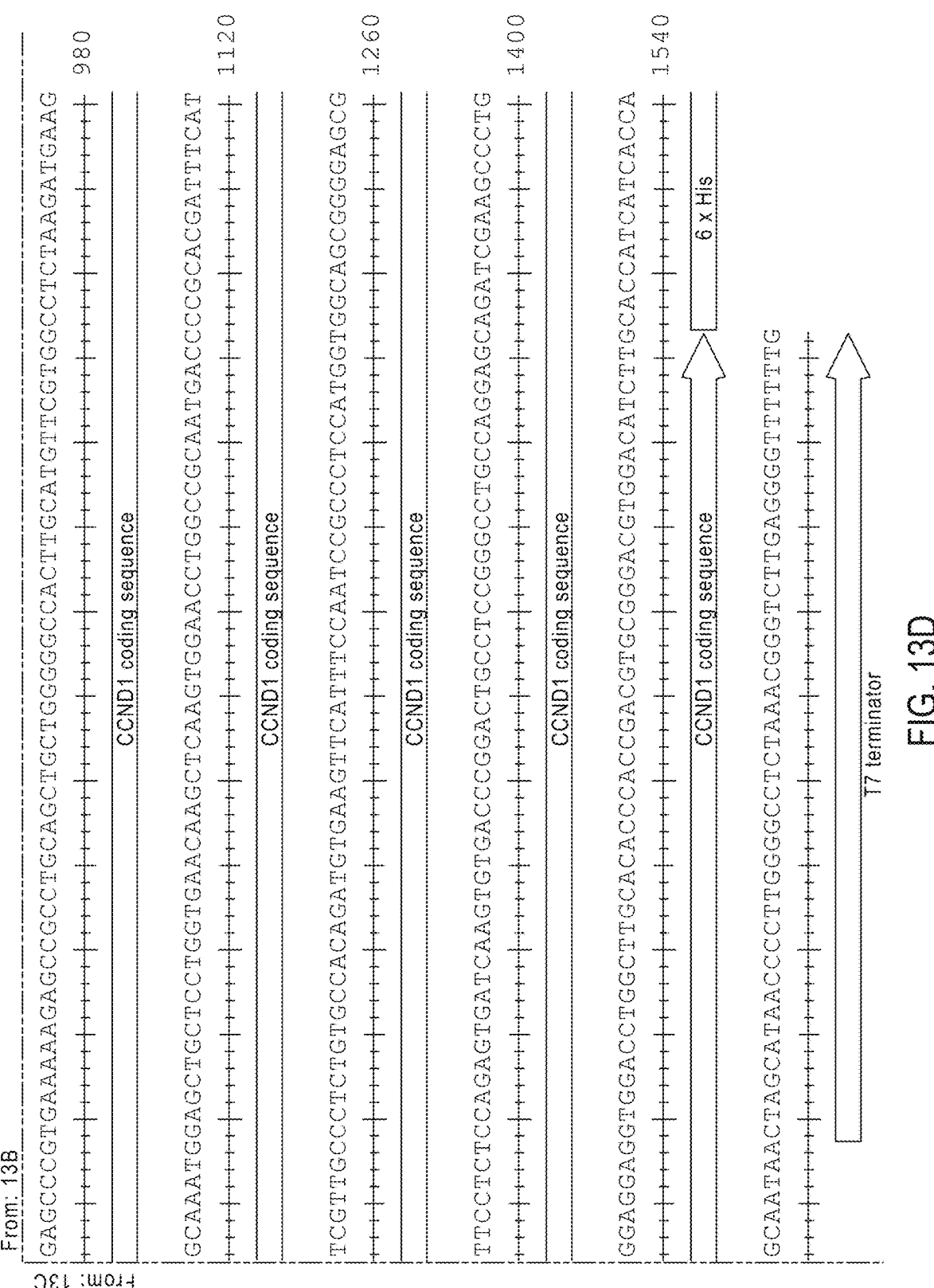

FIG. 13A-13D shows the nucleotide sequence of the 5'- and 3'-UTR regions shown in FIG. 12. It has been shown that the presence of a non-coding region 5' to the T7 promoter enhances expression. This non-coding regions is labeled "stuffer" in FIG. 13A-13D. The non-coding region may vary in length and may be from about 25 nucleotides to about 250 nucleotides.

However, for purposes of illustration, consider the situation where one hundred nucleic acid segments are to be assembled, each nucleic acid segment is one hundred base pairs in length and there is one error per 200 base pairs. The net result is that there will be, on average, 50 sequence errors in each 10,000 base pair assembled nucleic acid molecule. If one intends, for example, to express one or more proteins from the assembled nucleic acid molecule, then the number of amino acid sequence errors would likely be considered to be too high. Further, a number of the protein coding region nucleotide sequence errors will result in "frame shifts" mutations yielding proteins that will generally not be desired. Also, non-frame shift coding regions may result in the formation of proteins with point mutations. All of these will "dilute the purity" of the desired protein expression product and many of the produced "contaminant" proteins will be carried over into the final expression product mixture even if affinity purification is employed.

While sequencing of individual nucleic acid molecules may be performed, this is time consuming and involves additional cost. Thus, in many instances, one or more error removal step may be performed. Typically, such error removal steps will be performed after a first round of assembly. Thus, in one aspect, methods of the invention involve the following (in this order or different orders):

Fragment Amplification and/or Assembly (e.g., PCR/in vitro assembly).

Error Correction.

Final Assembly (e.g., in vivo assembly).

In various embodiments of methods of the invention, error removal steps may also be implemented by executing processor-executable instructions. The invention thus includes software based instructions for performing mechanical functions associated with error removal processes, as well as other aspects of the invention.

Any number of methods may be used for fragment amplification and assembly. One exemplary method is described in Yang et al., *Nucleic Acids Research* 21:1889-1893 (1993) and U.S. Pat. No. 5,580,759, the disclosure of which is incorporated herein by reference.

In the process described in the Yang et al. paper, a linear vector is mixed with double stranded nucleic acid molecules which share sequence homology at the termini. An enzyme with exonuclease activity (i.e., T4 DNA polymerase, T5 exonuclease, T7 exonuclease, etc.) is added which peels back one strand of all termini present in the mixture. The "peeled back" nucleic acid molecules are then annealed incubated with a DNA polymerase and deoxynucleotide triphosphates under condition which allow for the filling in of single-stranded gaps. Nicks in the resulting nucleic acid molecules may be repaired by introduction of the molecule into a cell or by the addition of ligase. Of course, depending on the application and work flow, the vector may be omitted. Further, the resulting nucleic acid molecules, or sub-portions thereof, may be amplified by polymerase chain reaction.

Other methods of nucleic acid assembly include those described in U.S. Patent Publication Nos. 2010/0062495 A1; 2007/0292954 A1; 2003/0152984 AA; and 2006/0115850 AA and in U.S. Pat. Nos. 6,083,726; 6,110,668; 5,624,827; 6,521,427; 5,869,644; and 6,495,318, the disclosures of which are incorporated herein by reference.

A method for the isothermal assembly of nucleic acid molecules is set out in U.S. Patent Publication No. 2012/0053087, the disclosure of which is incorporated herein by reference. In one aspect of this method, nucleic acid molecules for assembly are contacted with a thermolabile protein with exonuclease activity (e.g., T5 polymerase) a thermostable polymerase, and a thermostable ligase under conditions where the exonuclease activity decreases with time (e.g., 50° C.). The exonuclease "chews back" one strand of the nucleic acid molecules and, if there is sequence complementarity, nucleic acid molecule will anneal with each other. The thermostable polymerase fills in gaps and the thermostable ligase seals nicks.

One commercially available kit which may be used to assemble nucleic acid molecules of the invention, as well as for the insertion of such nucleic acid molecules into vectors is the GENEART® Seamless Cloning and Assembly Kit (cat. no. A13288), available from Life Technologies Corp., Carlsbad, CA.

Single-stranded binding proteins, such as T4 gene 32 protein and RecA, as well as other nucleic acid binding or recombination proteins known in the art, may be included, for example, to facilitate nucleic acid molecules annealing.

In some instances, nucleic acid molecules may be amplified on solid supports. Thus, the invention includes methods where nucleic acid molecules are synthesized but are not cleaved from solid supports they are synthesized on. In such instances, the amplified nucleic acid molecules may be used directed (e.g., as probes) or assembled as described elsewhere herein.

Figure 8:
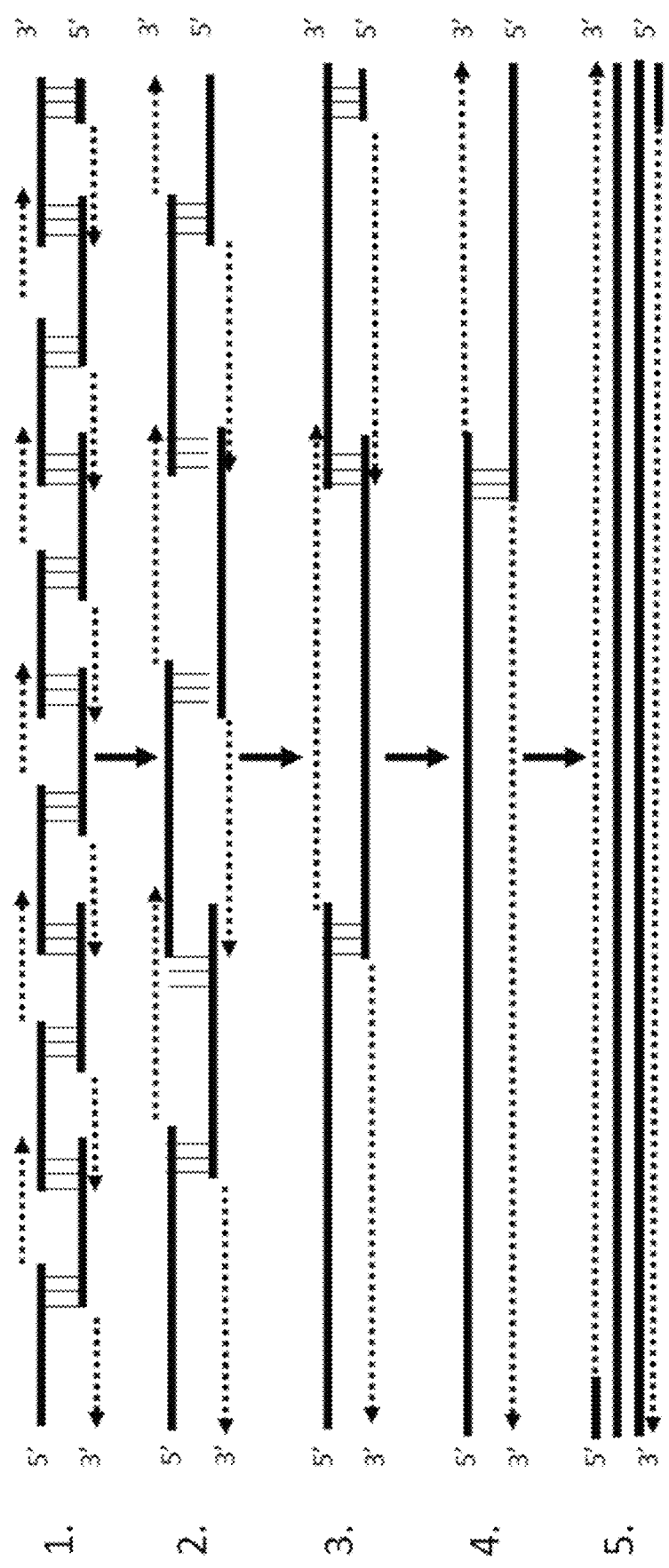
FIG. 8 shows a second nucleic acid assembly scheme. Dotted lines with arrows show PCR based synthesis direction and area.

One method for assembling nucleic acid molecules (FIG. 8) involves starting with overlapping nucleic acid molecules which are "stitched" together using PCR. In many instances, the stitched nucleic acid molecules will be chemically synthesized and will be less than 100 nucleotides in length (e.g., from about 40 to 100, from about 50 to 100, from about 60 to 100, from about 40 to 90, from about 40 to 80, from about 40 to 75, from about 50 to 85, etc. nucleotides). A process similar to that shown in FIG. 8 is set out in U.S. Pat. No. 6,472,184, the disclosure of which is incorporated herein by reference. Primers may also be used which contain restriction sites for instances where insertion into a cloning vector is desired. One suitable cloning system is referred to as Golden Gate which is set out in various forms in U.S. Patent Publication No. 2010/0291633 A1 and PCT Publication WO 2010/040531, the disclosures of which are incorporated herein by reference. Thus, where desirable, assembled nucleic acid molecules may be directly inserted into vectors and host cells. This may be appropriate when the desired construct is fairly small (e.g., less than 5 kilobases). Type IIs restriction site mediated assembly may be used to assemble multiple fragments (e.g., two, three, five, eight, ten, etc.) when larger constructs are desired (e.g., 5 to 100 kilobases).

An alternative method for PCR-based assembly of nucleic acid molecules (e.g., chemically synthesized nucleic acid molecules) is based on the direct ligation of overlapping pairs of 5'-phosphorylated nucleic acid molecules ("ligation-based assembly"). In this process, single stranded nucleic acid molecules are synthesized, phosphorylated and annealed to form double stranded molecules with complementary overhangs (e.g., overhangs of four nucleotides). The individual double stranded molecules are then ligated to each other to form larger constructs. In certain embodiments this method may be desirable over PCR methods in particular where highly repetitive sequences, such as GC stretches are to be assembled. This method may be used to assemble from about two to about forty nucleic acid molecules (e.g., from about two to about forty, from about three to about forty, from about five to about forty, from about eight to about forty, from about two to about thirty, from about two to about twenty, from about two to about ten, etc. nucleic acid molecules). A related method is described in U.S. Pat. No. 4,652,639, the disclosure of which is incorporated herein by reference.

Figure 7:
FIG. 7 shows a nucleic acid assembly scheme. The thick ends on the assembled nucleic acid molecule shown at the bottom of the figure represent regions added by external primers, also referred to as terminal primers.

In many instances when ligation-based assembly is employed using chemically synthesized nucleic acid molecules, the molecules will be less than 100 base pairs in length. Also, the complementary overlaps may be used for joining the nucleic acid molecules will generally be between two and ten (e.g., from about two to about ten, from about four to about ten, from about five to about ten, from about two to about eight, from about three to about seven, etc.) nucleotides in length (FIG. 7).

Further, as shown in FIG. 8 and the right side of FIG. 9, multiple rounds of polymerase chain reactions may be used to generate successively larger nucleic acid molecules.

Fragments to be assembled will generally contain sequences that are overlapping at their termini. In one embodiment, the overlaps are approximately 10 base pairs; in other embodiments, the overlaps may be 15, 25, 50, 60, 70, 80 or 100 base pairs, etc. (e.g., from about 10 to about 120, from about 15 to about 120, from about 20 to about 120, from about 25 to about 120, from about 30 to about 120, from about 40 to about 120, from about 10 to about 40, from about 15 to about 50, from about 40 to about 80, from about 60 to about 90, from about 20 to about 50, etc. base pairs). In order to avoid mis-assembly, individual overlaps will typically not be duplicated or closely matched amongst the fragments. Since hybridization does not require 100% sequence identity between the participating nucleic acid molecules or regions, each terminus should be sufficiently different to prevent mis-assembly. Further, termini intended to undergo homologous recombination with each other should share at least 90%, 93%, 95%, or 98% sequence identity.

As noted above, in most instances, regardless of the method by which a larger nucleic acid molecule is generated from chemically synthesized nucleic acid molecules, errors from the chemical synthesis process will be present. Thus, in many instances, error correction will be desirable. Error correction can be achieved by any number of means. One method is by individually sequencing chemically synthesized nucleic acid molecules. Sequence-verified nucleic acid molecules can then be retrieved by various means. One way of selecting nucleic acid molecules of correct sequence is referred to as "laser catapulting" and relies on the use of high-speed laser pulses to eject selected clonal nucleic acid populations from a sequencing plate. This method is described, for example, in U.S. Patent Publication No. 2014/0155297 the disclosure of which is incorporated herein by reference.

Figure 10:
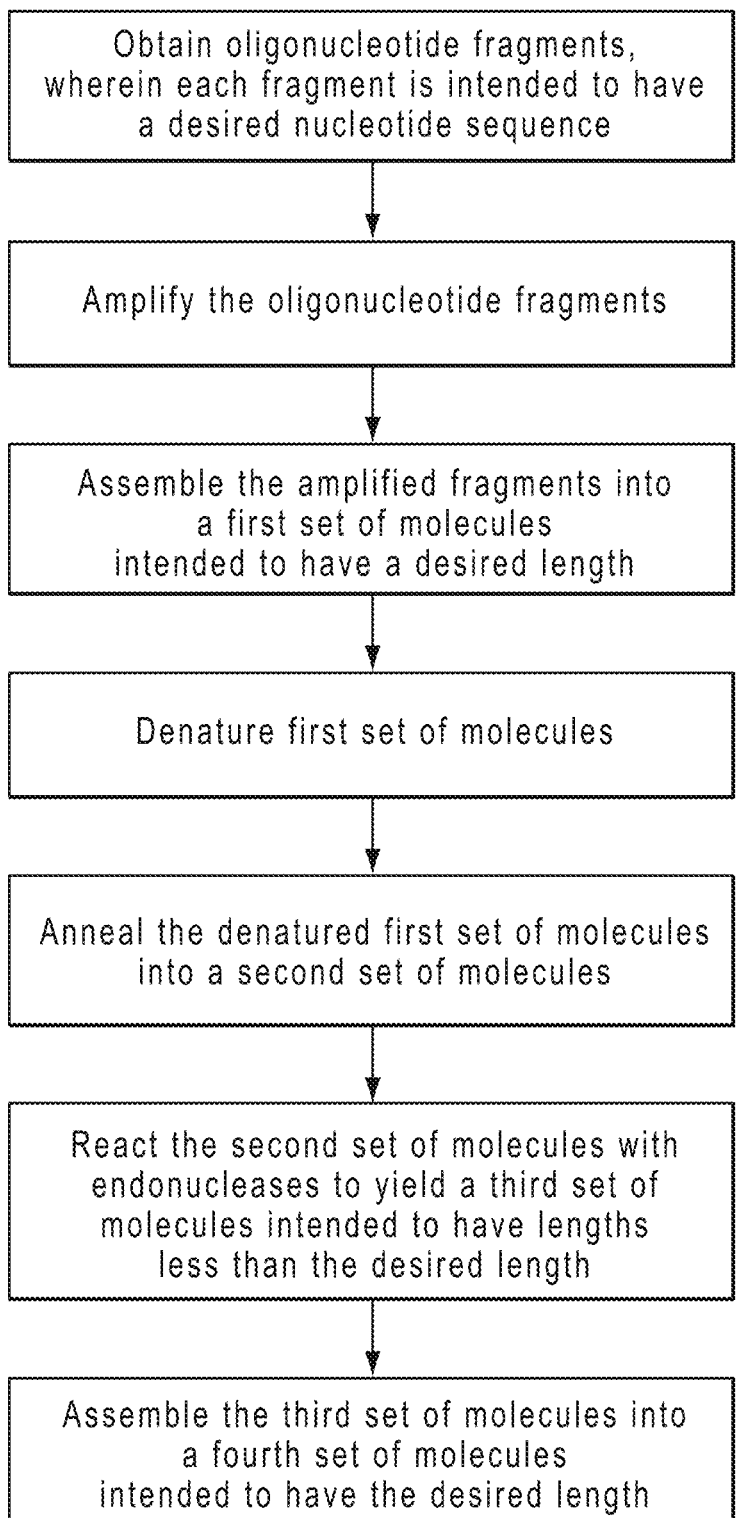
FIG. 10 is a flow chart of an exemplary process for synthesis of error-minimized nucleic acid molecules.

Another method of error correction is set out in FIG. 10. FIG. 10 is a flow chart of an exemplary process for synthesis of error-minimized nucleic acid molecules. In the first step, nucleic acid molecules of a length smaller than that of the full-length desired nucleotide sequence (i.e., "nucleic acid molecule fragments" of the full-length desired nucleotide sequence) are obtained. Each nucleic acid molecule is intended to have a desired nucleotide sequence that comprises a part of the full length desired nucleotide sequence. Each nucleic acid molecule may also be intended to have a desired nucleotide sequence that comprises an adapter primer for PCR amplification of the nucleic acid molecule, a tethering sequence for attachment of the nucleic acid molecule to a DNA microchip, or any other nucleotide sequence determined by any experimental purpose or other intention. The nucleic acid molecules may be obtained in any of one or more ways, for example, through synthesis, purchase, etc.

In the optional second step, the nucleic acid molecules are amplified to obtain more of each nucleic acid molecule. In many instances, however, sufficient numbers of nucleic acid molecules will be produced so that amplification is not necessary. When employed, amplification may be accomplished by any method known in the art, for example, by PCR, Rolling Circle Amplification (RCA), Loop Mediated Isothermal Amplification (LAMP), Nucleic Acid Sequence Based Amplification (NASBA), Strand Displacement Amplification (SDA), Ligase Chain Reaction (LCR), Self Sustained Sequence Replication (3SR) or solid phase PCR reactions (SP-PCR) such as Bridge PCR etc. (see, e.g., Fakruddin et al., *J. Pharm. Bioallied. Sci.* 5(4):245-252 (2013) for an overview of the various amplification techniques). Introduction of additional errors into the nucleotide sequences of any of the nucleic acid molecules may occur during amplification. In certain instances it may be favorable to avoid amplification following synthesis. The optional amplification step may be omitted where nucleic acid molecules have been produced at sufficient yield in the first step. This may be achieved by using improved compositions and methods of the invention such as, e.g., optimized bead formats as described elsewhere herein, designed to allow synthesis of nucleic acid molecules at sufficient yield and quality.

In the third step, the optionally amplified nucleic acid molecules are assembled into a first set of molecules intended to have a desired length, which may be the intended full length of the desired nucleotide sequence or a subfragment thereof. Assembly of amplified nucleic acid molecules into full-length molecules or subfragments may be accomplished in any way, for example, by using a PCR-based method.

In the fourth step, the first set of full-length molecules is denatured. Denaturation renders single-stranded molecules from double-stranded molecules. Denaturation may be accomplished by any means. In some embodiments, denaturation is accomplished by heating the molecules.

In the fifth step, the denatured molecules are annealed. Annealing renders a second set of full-length or subfragment double-stranded molecules from single-stranded molecules. Annealing may be accomplished by any means. In some embodiments, annealing is accomplished by cooling the molecules. Some of the annealed molecules may contain one or more mismatches indicating sites of sequence error.

In the sixth step, the second set of full-length molecules are reacted with one or more mismatch cleaving endonucleases to yield a third set of molecules intended to have lengths less than the length of the complete desired gene sequence. The endonucleases cut one or more of the molecules in the second set into shorter molecules. The cuts may be accomplished by any means. Cuts at the sites of any nucleotide sequence errors are particularly desirable, in that assembly of pieces of one or more molecules that have been cut at error sites offers the possibility of removal of the cut errors in the final step of the process. Variations of this process are as follows. First, two or more (e.g., two, three, four, five, six, etc.) rounds of error correction may be performed. Second, more than one endonuclease may be used in one or more rounds of error correction. For example, T7 endonuclease I and Cel II may be used in each round of error correction. Third, different endonucleases may be used in different error correction rounds. In an exemplary embodiment, the molecules are cut with T7 endonuclease I, *E. coli* endonuclease V, and Mung Bean endonuclease in the presence of manganese. In this embodiment, the endonucleases are intended to introduce cuts in the molecules at the sites of any sequence errors, as well as at random sites where there is no sequence error. In another embodiment, T7 endonuclease I and Cel II may be used in a first round of error correction and Cel II may be used alone in a second round of error correction. In another exemplary embodiment, the molecules are cut only with one endonuclease (which may be a single-strand nuclease, such as Mung Bean endonuclease or a resolvase, such as T7 endonuclease I or another endonuclease of similar functionality). In yet another embodiment the same endonuclease (e.g., T7 endonuclease I) may be used in two subsequent error correction rounds.

In many instances, a ligase may be present in reaction during error correction. It is believed that some endonucleases used in error correction processes have nickase activity. The inclusion of one or more ligase is believed to seal nicks caused by such enzymes and increase the yield of error corrected nucleic acid molecules after amplification. Exemplary ligases that may be used are T4 DNA ligase, Taq ligase, and PBCV-1 DNA ligase. Ligases used in the practice of the invention may be thermolabile or thermostabile (e.g., Taq ligase). If a thermoloabile ligase is employed, it will typically need to be added to a reaction mixture for each error correction cycle. Thermostabile ligases will typically not need to be readded during each cycle, so long as the temperature is kept below their denaturation point.

In instances where the second set of molecules represents a subfragment of the full-length molecules, two or more subfragments (e.g., two or three or more subfragments) together representing the full-length molecules may be combined and reacted with the one or more mismatch cleaving endonucleases in a single reaction mix. For example, where the open reading frame that is to be assembled is longer than 1 kb, it may be broken up into two or more subfragments separately assembled in parallel reactions in step three and the resulting two or more subfragments may be combined and error-corrected in a single reaction as indicated on the rights sides of FIG. 9. The amount of subfragments to be combined in a single error correction cycle may depend on the length of the individual subfragments. For example, up to three subfragments of about 1 kb in length may be efficiently combined in a single reaction mixture. Of course, more than three (e.g., four, five, six, seven, eight, nine, etc.) subfragments may be combined. Assembly efficiency may decrease so long as at least one correctly assembled amplifiable and/or replicable nucleic acid molecule is obtained. Thus, numerous subfragments (e.g., subfragments of about 1 kb in length) may be assembled so long as a correctly assembled product nucleic acid molecule is obtained from the assembly process.

Figure 9A:
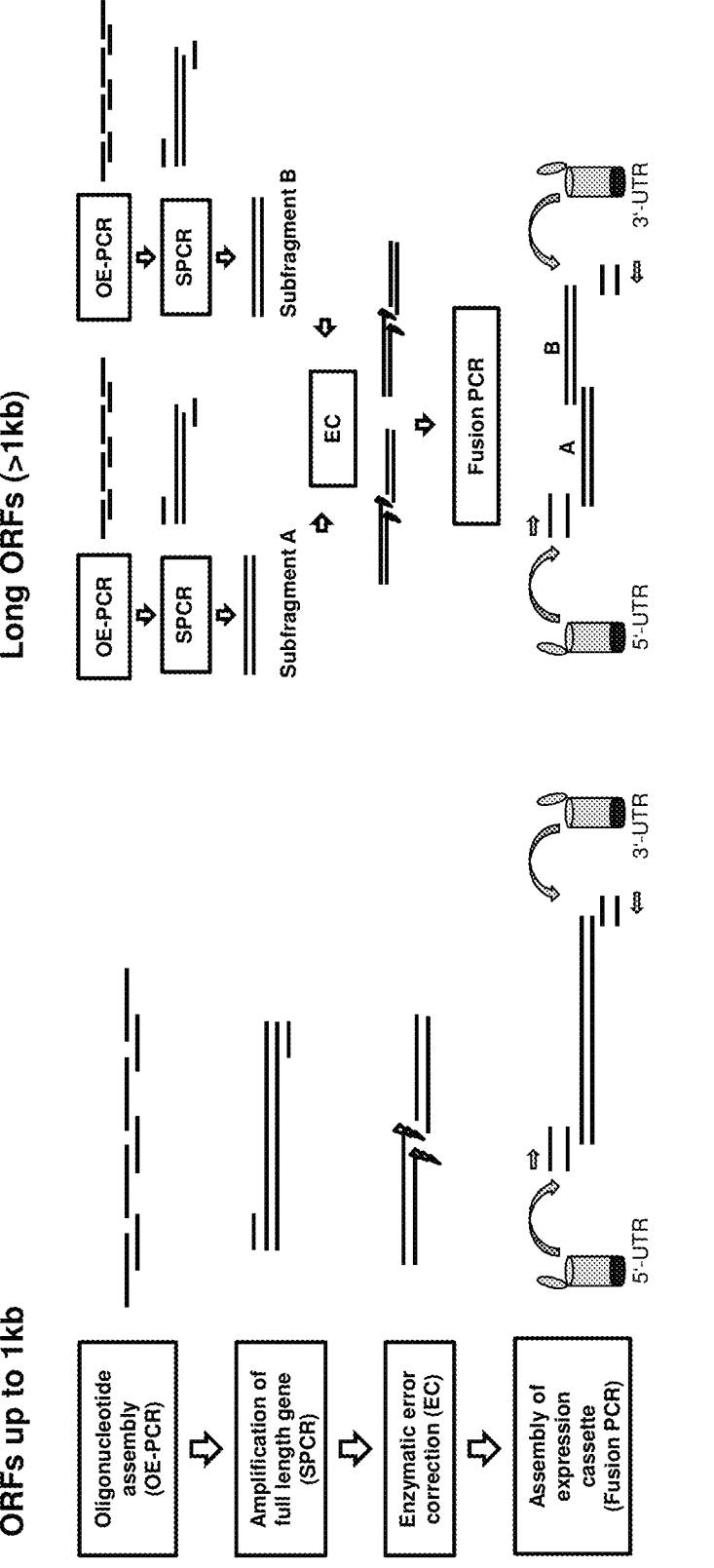

In the seventh step, the third set of molecules is assembled into a fourth set of molecules, whose length is intended to be the full length of the desired nucleotide sequence. In the seventh step, which is typically based on overlap extension PCR, the 3'→5' exonuclease activity of the DNA polymerase removes the 3' overhangs generated by endonuclease cleavage in the sixth step at sites of mismatch thereby removing the error. This principle is outlined, e.g., in Saaem et al. ("Error correction of microchip synthesized genes using Surveyor nuclease", Nucl, Acids Res., 40:e23 (2012)). Such final assembly step may be performed in the presence of terminal primers thereby including functionalities required for downstream processes. For example, the full length nucleotide sequence may be assembled in the presence of oligonucleotides encoding the 5' and 3' UTRs required for mRNA functionality as indicated in FIG. 9A. In such instance, the subfragment encoding the open reading frame is designed to comprise overlapping regions of at least 20, preferably about 30 bp with the 5' and 3' UTR encoding primers. A respective PCR reaction may be set up to first allow the error-corrected fragments to assemble by overlap extension to the full length in about 15 cycles of denaturation, annealing and extension in the absence of the terminal primers, followed by additional 20 cycles in the presence of the terminal primers.

Alternatively, where the error-corrected strings are to be inserted into a plasmid already containing such additional functionalities (such as the 5' and 3' UTRs), the assembly in the seventh step may be performed in the presence of the plasmid instead of terminal primers as indicated in FIG. 9B. The plasmid may be provided in a linearized form with the 5' and 3' terminal regions of the linearized plasmid overlapping the 5' and 3' terminal ends of the string (e.g. by at least 20 bp, preferably at least 30 bp). Such method may be performed, for example, using the circular polymerase extension cloning method as described in Quan and Tian, ("Circular Polymerase Extension Cloning of Complex Gene Libraries and Pathways", PLoS One, 4:e6441, 2009). In other embodiments, the string may have been designed to contain terminal restriction enzyme recognition sites for subsequent cloning into the plasmid via type II or type IIS mediated cloning techniques as described elsewhere herein. In such instances the assembly in the seventh step may be followed by an additional amplification step to obtain sufficient amounts of the string to be inserted into the plasmid. In another exemplary embodiment, the termini of the assembled string may have been designed to share sequence homology with the termini of the linearized plasmid and may be inserted by exonuclease-mediated seamless cloning methods as described elsewhere herein. Because of the late-stage error correction enabled by the provided method, the set of molecules is expected to have many fewer nucleotide sequence errors than can be provided by methods in the prior art. Optionally, steps four to seven may be repeated one or several times to further increase the efficiency of error reduction.

The process set out above and in FIG. 10 is also set out in U.S. Pat. No. 7,704,690, the disclosure of which is incorporated herein by reference. Furthermore, the process described above may be encoded onto a computer-readable medium as processor-executable instructions.

Another process for effectuating error correction in chemically synthesized nucleic acid molecules is by a commercial process referred to as ERRASE™ (Novici Biotech). Error correction methods and reagent suitable for use in error correction processes are set out in U.S. Pat. Nos. 7,838,210 and 7,833,759, U.S. Patent Publication No. 2008/0145913 A1 (mismatch endonucleases), and PCT Publication WO 2011/102802 A1, the disclosures of which are incorporated herein by reference.

Exemplary mismatch binding and/or cleaving enzymes include endonuclease VII (encoded by the T4 gene 49), RES I endonuclease, CEL I endonuclease, and SP endonuclease or an endonuclease containing enzyme complex. For example, the MutHLS complex constitutes a bacterial mismatch repair system, wherein MutS has mismatch detection and mismatch binding activity, MutH has nuclease activity and MutL directs MutH to MutS-bound mismatch sites. The skilled person will recognize that other methods of error correction may be practiced in certain embodiments of the invention such as those described, for example, in U.S. Patent Publication Nos. 2006/0127920 AA, 2007/0231805 AA, 2010/0216648 A1, 2011/0124049 A1 or U.S. Pat. No. 7,820,412, the disclosures of which are incorporated herein by reference.

One error correction method involves the following steps. The first step is to denature DNA contained in a reaction buffer (e.g., 200 mM Tris-HCl (pH 8.3), 250 mM KCl, 100 mM MgCl$_2$, 5 mM NAD, and 0.1% TRITON® X-100) at 98° C. for 2 minutes, followed by cooling to 4° C. for 5 minutes, then warming the solution to 37° C. for 5 minutes, followed by storage at 4° C. At a later time, T7 endonuclease I and DNA ligase are added to the solution at 37° C. for 1 hour. The reaction is stopped by the addition EDTA. A similar process is set out in Huang et al., *Electrophoresis* 33:788-796 (2012).

Some error correction processes suitable for use in methods of the invention are as follows. Two μl of nucleic acid (~150 ng) is mixed with 1 μl of 10× Assay Buffer (Tris 200 mM, KCl 250 mM, MgCl2 200 mM, NAD 5 mM, X-100 0.1% pH 8.3+/−0.05 at room temperature) and 5 μl of water. The nucleic acid is then denatured and re-annealed as follows: 98° C. for 2 minutes, 4° C. for 5 minutes, 37° C. for 5 minutes, then maintained at 4° C. One μl T7N1/Tth ligase mix (1782 μl Storage Buffer (Tris 10 mM, EDTA 0.1 mM, KCl 50 mM, X-100 0.15%, BSA 0.2 μg/ml, Glycerol 50% pH 7.4+/−0.05 at 4° C.), 12 μl T7N1 (1:150) (stock 0.92 mg total protein/ml) (6.1 ng total protein/μl after dilution), and 6 μl Tth Ligase (1:300) (Stock 1 mg total protein/ml) (3.3 ng total protein/μl after dilution). The amount and proportion of enzymes to be included in the mix are determined by titrating them using a mismatched substrate in the context of the Surveyor Assay (Transgenomic Inc.). The right amount and proportion is that one that digests 50% of the template. 1 μl of Cel II (Transgenomic Inc., Surveyor kit component "SURVEYOR Nuclease S") is then added to the nucleic acid and mixed. In some embodiments, the reaction mixture may comprise 2 μl of nucleic acid, 1 μl Taq Ligase NEB 40 units, 1 μl T7E1 NEB 10 units, 1 μl of 10× Taq ligase buffer in 10 μl total volume.

The mixture is then incubated at 45° C. for 20 minutes without heating the lid cover. Two μl of error-corrected sample is then transferred to a PCR mix and PCR is performed. The PCR product is purified and an aliquot is cloned into a zero-blunt TOPO vector for sequencing. After a second round of error correction, the resulting PCR product is purified using a PureLink PCR column purification kit and then subjected to error correction as described above. For the third round of error correction, the resulting PCR product is purified and subjected to error correction again. The resulting PCR product is purified for subsequent cloning and sequencing.

Synthetically generated nucleic acid molecules typically have error rate of about 1 base in 300-500 bases. As noted above in many instances, conditions can be adjusted so that synthesis errors are substantially lower than 1 base in 300-500 bases. Further, in many instances, greater than 80% of errors are single base frame shift deletions and insertions. Also, less than 2% of errors result from the action of polymerases when high fidelity PCR amplification is employed. Therefore, error-correction processes using PCR-based assembly steps as described above may be combined with one or more error-correction methods not involving polymerase activity. In many instances, mismatch endonuclease (MME) correction will be performed using fixed protein:DNA ratio. Non-PCR-based error correction may, e.g., be achieved by separating nucleic acid molecules with mismatches from those without mismatches by binding with a mismatch binding agent in a number of ways. For example, mixtures of nucleic acid molecules, some having mismatches, may be (1) passed through a column containing a bound mismatch binding protein or (2) contacted with a surface (e.g., a bead (such as a magnetic bead), plate surface, etc.) to which a mismatch binding protein is bound.

Exemplary formats and associated methods involve those using beads to which a mismatch binding protein is bound.

For example, a solution of nucleic acid molecules may be contacted with beads to which is bound a mismatch binding protein. Nucleic acid molecules that are bound to the mismatch binding protein are then linked to the surface and not easily removed or transferred from the solution.

Figure 11:
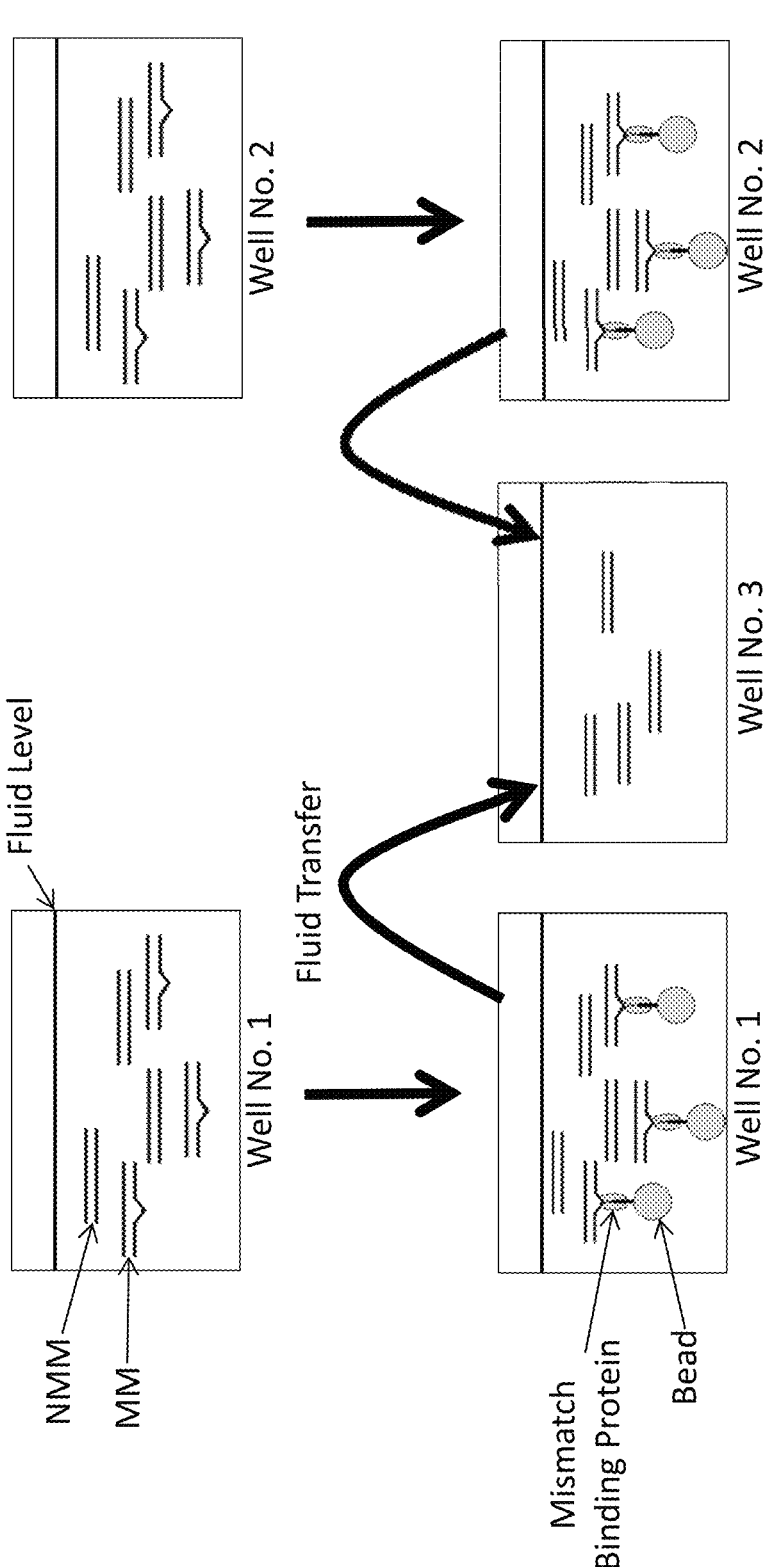
FIG. 11 shows a schematic representation of a workflow employing bead bound mismatch repair binding proteins for the separation of nucleic acid molecules that contain mismatches from those that do not contain mismatches. NMM refers to a non-mismatched nucleic acid molecule and MM refers to a mismatched nucleic acid molecule.

In a specific format set out in FIG. 11, beads with a bound mismatch binding protein may be placed in a vessel (e.g., a well of a multi-well plate) with nucleic acid molecules present in solution, under conditions that allow for the binding of nucleic acid molecules with mismatches to the mismatch binding protein (e.g., 5 mM MgCl₂, 100 mM KCl, 20 mM Tris-HCl (pH 7.6), 1 mM DTT, 25° C. for 10 minutes). Fluid may then be transferred to another vessel (e.g., a well of a multi-well plate) without transferring of the beads and/or mismatched nucleic acid molecules. In one exemplary embodiment, the endonuclease/PCR-based error correction method described in FIG. 9 may be combined with the error correction method described in FIG. 11 to remove nucleic acid molecules (fragments, strings or plasmids) still containing errors introduced by the activity of a polymerase.

Figure 14:
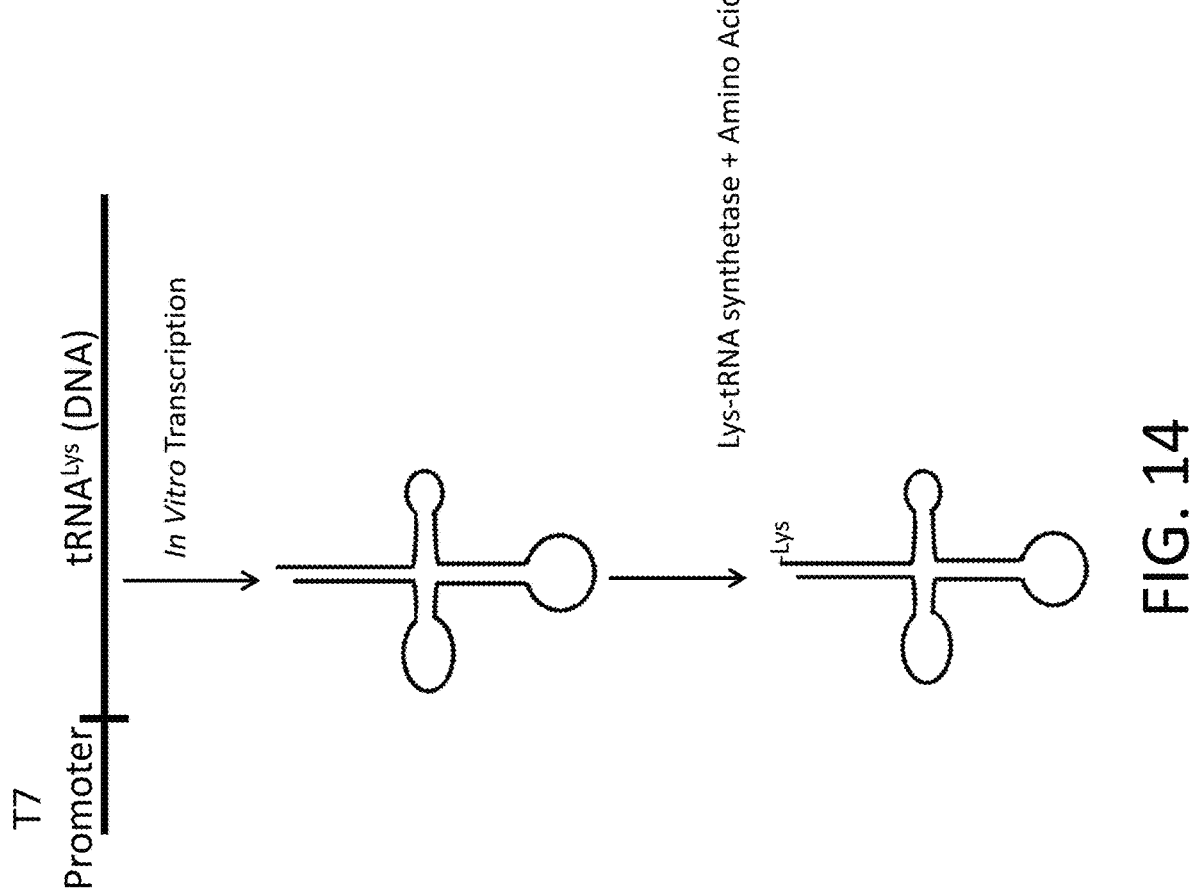
FIG. 14 shows a schematic of the generation of a lysine (Lys) charged tRNA by in vitro transcription, followed by tRNA synthetase mediated connection of lysine (needs correction).
Figure 15A:
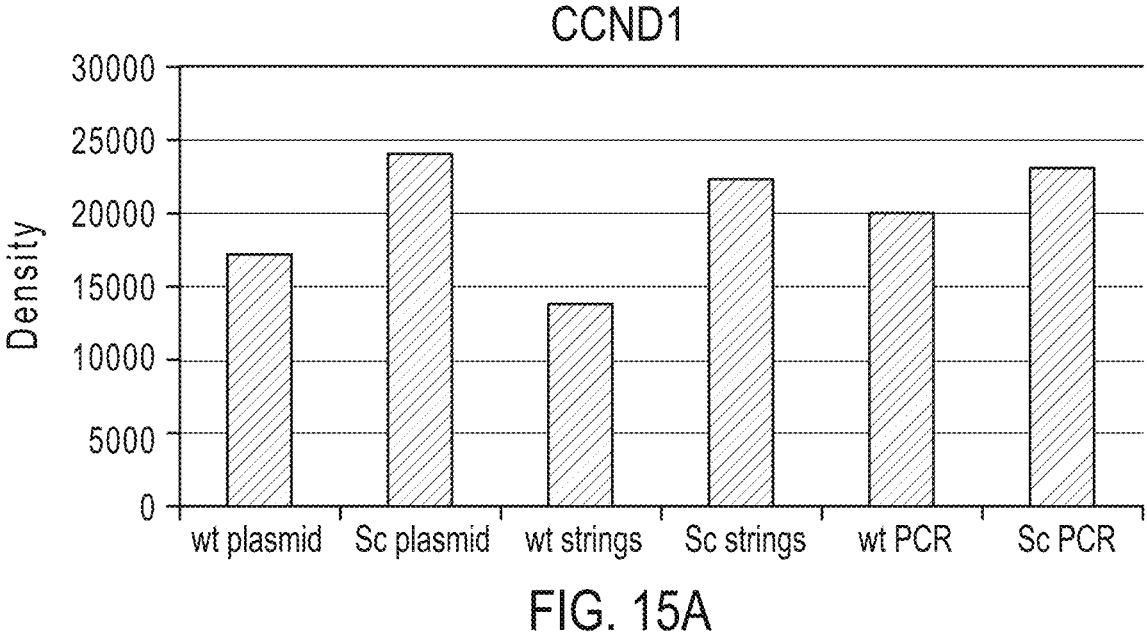
FIGS. 15A-15D show expression data derived from Western blots of four protein expression products. The lanes are labeled as follows: wt plasmid, Sc plasmid, wt strings, Sc strings, wt PCR, and Sc PCR. "wt" refers to the wild-type coding sequences. "Sc" refers to *Saccharomyces cerevisiae* codon optimized coding sequences. "plasmid" refers to plasmid DNA. "strings" refer to chemically synthesized DNA. "PCR" refers to DNA prepared by polymerase chain reaction. CCND1 refers to the 295 amino acid human Cyclin D1 protein, green fluorescent protein (GFP) refers to green fluorescent protein, and Streptokinase refers to the 424 amino acid *Streptococcus* streptokinase protein. The nucleotide sequences for each of the four proteins set out in these figures are set out in FIGS. 16-19 below.
Figure 15B:
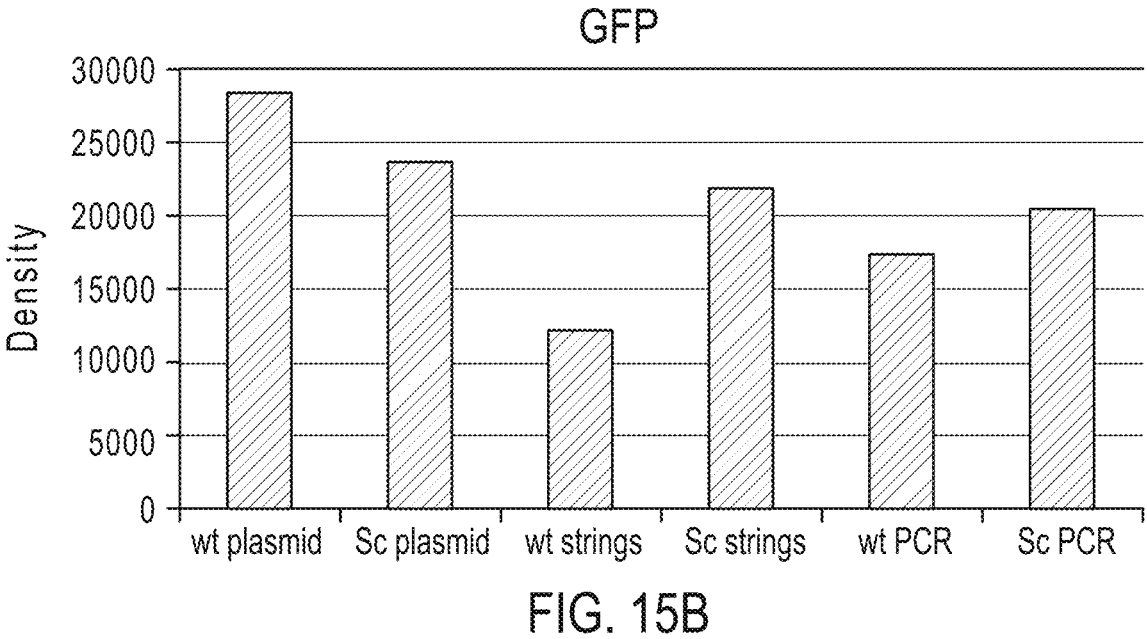
Figure 15C:
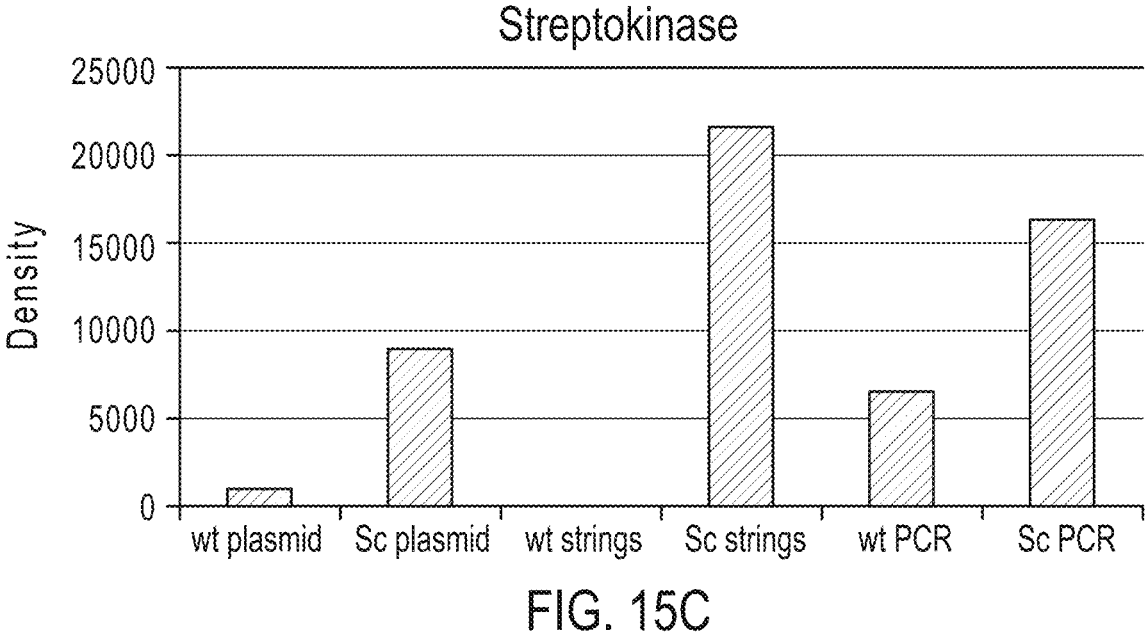
Figure 15D:
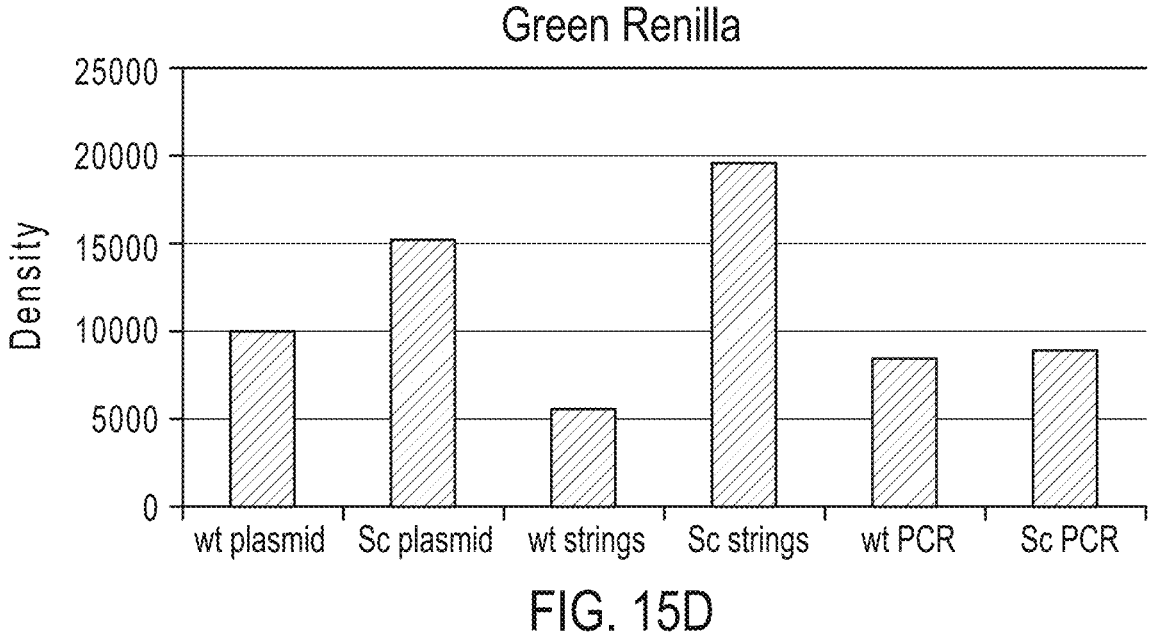

Any number of methods may be used for transferring fluids containing nucleic acid molecules. For example, a micropipette may be used. Further, a magnetic field may be used to hold magnetic beads to which mismatched nucleic acid molecules are bound in place, for example, during pipetting or while the fluid to be transferred is otherwise removed. As another example, a solid object (e.g., a glass or metal rod) may be introduced into a first vessel containing nucleic acid to be transferred, followed by dipping the solid object into fluid present in a second vessel. Fluid adhering to the solid object, and nucleic acid molecules associated with the solid object, would be transferred from the first vessel into the second vessel. Acoustic fluid transfer (described elsewhere herein) may also be employed. Acoustic liquid transfer may be used to transfer fluid from the surface of one vessel (e.g., Well No. 1 and/or Well No. 2 in FIG. 13A-13D), where beads are located at the bottom of the first vessel, to a second vessel (e.g., Well No. 3 in FIG. 14). Thus, bead bound nucleic acid molecules containing mismatches will not be in close proximity to fluid being transferred.

Further beads may be separated from a solution containing nucleic acid molecules that have not bound to the beads. This results in the separation of nucleic acid molecules containing mismatches from those that do not contain mismatches.

As noted above, another method for removal of error from chemically synthesized nucleic acid molecules is by selection of nucleic acid molecules having correct nucleotide sequences. This may be done by the selection of a single nucleic acid molecule for amplification, then sequencing of the amplification products to determine if any errors are present. Thus, the invention also includes selection methods for the reduction of sequence errors. Methods for amplifying and sequence verifying nucleic acid molecules are set out in U.S. Pat. No. 8,173,368, the disclosure of which is incorporated herein by reference. Similar methods are set out in Matzas et al., *Nature Biotechnology,* 28:1291-1294 (2010). Selection of sequence-verified nucleic acid molecules can be accomplished by various means including methods using laser pulses as described elsewhere herein.

Methods according to this aspect of the invention may include the following steps: (a) providing a mixture of nucleic acid molecules synthesized to have the same nucleotide sequence, (b) separating nucleic acid molecules in the mixture such that amplification results in progeny nucleic acid molecules being derived from a single starting nucleic acid molecule, (c) sequencing more than one amplified nucleic acid molecule generated in step (b), and (d) identifying at least one individual nucleic acid with the desired sequence from the nucleic acid molecules sequenced in step (c). The nucleic acid molecule identified in step (d) may then be used as one nucleic acid molecule in an assembly process, as described elsewhere herein.

According to various embodiments described herein, a computer-readable medium may be encoded with processor-executable instructions for: (a) providing a mixture of nucleic acid molecules synthesized to have the same nucleotide sequence, (b) separating nucleic acid molecules in the mixture such that amplification results in progeny nucleic acid molecules being derived from a single starting nucleic acid molecule, (c) sequencing more than one amplified nucleic acid molecule generated in step (b), and (d) identifying at least one individual nucleic acid with the desired sequence from the nucleic acid molecules sequenced in step (c). The nucleic acid molecule identified in step (d) may then be used as one nucleic acid molecule in an assembly process, as described elsewhere herein. In various embodiments, the computer-readable medium may be included in a system configured to reduce error from chemically synthesized nucleic acid molecules by selection of nucleic acid molecules having correct nucleotide sequences.

Sequence errors in nucleic acid molecules may be referenced in a number of ways. As examples, there is the error rate associated with the synthesis nucleic acid molecules, the error rate associated with nucleic acid molecules after error correct and/or the selection, and the error rate associated with end product nucleic acid molecules (e.g., error rates of (1) a synthetic nucleic acid molecules that have either been selected for the correct sequence or (2) assembled chemically synthesized nucleic acid molecules). These errors may come from the chemical synthesis process, assembly processes, and/or amplifications processes. Errors may be removed or prevent by methods, such as, the selection of nucleic acid molecules having correct sequences, error correct, and/or improved chemical synthesis methods.

In some instances, methods of the invention will combine error removal and prevention methods to produce nucleic acid molecules with relative low numbers of errors. Thus, assembled nucleic acid molecules produced by methods of the invention may have error rates from about 1 base in 2,000 to about 1 base in 30,000, from about 1 base in 4,000 to about 1 base in 30,000, from about 1 base in 8,000 to about 1 base in 30,000, from about 1 base in 10,000 to about 1 base in 30,000, from about 1 base in 15,000 to about 1 base in 30,000, from about 1 base in 10,000 to about 1 base in 20,000, etc.

In some instances, assembly and maintenance of nucleic acid molecules involves either the generation of nucleic acid molecules that contain elements such as one or more origin of replication (e.g., two origins of replication which are functional in different cell types) and one or selection marker (e.g., one or more positive selection marker and/or one of more negative selection marker). Nucleic acid molecules assembled and/or maintained intracellularly may be removed from a cell prior to use in IVTT (and/or IVTr or IVTl) reactions. Further, in some instances, cellular components may be included in IVTT (and/or IVTr or IVTl) reaction mixtures and may provide some or all of the IVTT (and/or IVTr or IVTl) machinery.

Nucleic acid molecules introduced into cells for assembly will normally have certain features which allow them to be assembled in a particular order. One feature is terminal sequence homology between nucleic acid molecules being assembled.

In some instances, standard ligase based joining of partially and fully assembled nucleic acid molecules may be employed. For example, fully assembled nucleic acid molecule may be generated with restriction enzyme sites near their termini. These nucleic acid molecules may then be treated with one of more suitably restrictions enzymes to generate, for example, either one or two "sticky ends". These sticky end molecules may then be introduced into a vector by standard restriction enzyme-ligase methods. In instances where the inert nucleic acid molecules have only one sticky end, ligases may be used for blunt end ligation of the "non-sticky" terminus.

Assembled nucleic acid molecules may also include functional elements which confer desirable properties (e.g., origins of replication, selectable markers, etc.). In many instances, the assembled nucleic acid molecules will be assembled from multiple individual nucleic acid segments with one of the segments being a vector (e.g., a linear vector).

In in vivo assembly methods, a mixture of all of the fragments to be assembled is often used to transfect the host recombination and assembly cell using standard transfection techniques. The ratio of the number of molecules of fragments in the mixture to the number of cells in the culture to be transfected should be high enough to permit at least some of the cells to take up more molecules of fragments than there are different fragments in the mixture. Thus, in most instances, the higher the efficiency of transfection, the larger number of cells will be present which contain all of the nucleic acid segments required to form the final desired assembled nucleic acid molecule. Technical parameters along these lines are set out in U.S. Patent Publication No. 2009/0275086 A1, the disclosure of which is incorporated herein by reference.

Nucleic acid molecules assembled by methods of the invention will typically encode polypeptides of between ninety amino acids and two thousand amino acids. Coding regions of nucleic acid molecules generated by methods of the invention will thus often be between 270 and 6,000 base pairs.

Elements that may be associated with nucleic acid molecules of the invention include promoters, enhancers, poly adenylation signals, poly adenylation coding sequences, 5' and 3' UTRs and other components suitable for the particular use(s) of the nucleic acid molecules (e.g., enhancing mRNA or protein production efficiency).

It may be desirable at a number of points during workflows of the invention to separate nucleic acid molecules from reaction mixture components (e.g., dNTPs, primers, tRNA molecules, buffers, salts, proteins, etc.). This may be done a number of ways. For example, the nucleic acid molecules may be precipitated or bound to a solid support (e.g., magnetic beads as set out in Example 2). Once separated from reaction components for facilitating a process (e.g., nucleic acid synthesis, error correction, etc.), nucleic acid molecules may then be used in additional reactions (e.g., assembly reactions).

Nucleic Acid Molecules

Nucleic acid molecules produced by method of the invention and/or using compositions for the invention may vary substantially in size and form. For example, nucleic acid molecules assembled by methods of the invention will typically encode polypeptides of between ninety amino acids and two thousand amino acids (e.g., from about 100 to about 2,000, from about 200 to about 2,000, from about 400 to about 2,000, from about 600 to about 2,000, from about 800 to about 2,000, from about 1,000 to about 2,000, from about 100 to about 1,500, from about 100 to about 1,200, from about 100 to about 1,000, from about 500 to about 1,200, etc. amino acids) and may have 5' and/or 3' terminal elements for expression, replication, and/or other functions (e.g., chromosomal integration).

One exemplary format of nucleic acid molecules of the invention is shown in FIG. 12. In various methods of the invention, nucleic acid molecules such as this may be directly used for IVTT (and/or IVTr or IVTl) or introduced into a vector first, then used for IVTT (and/or IVTr or IVTl). Further, nucleic acid molecules such as the one represented in FIG. 12 may be introduced into vectors for (for example) replication, then excised from the vector and used for IVTT (and/or IVTr or IVTl). Also, nucleic acid molecules of the coding region may be introduced into vectors that contain transcriptional control sequences (as well as other components) and the vector may be directly used for IVTT (and/or IVTr or IVTl) or a portion of the vector may be excised and the linear nucleic acid molecule segment may be used for IVTT (and/or IVTr or IVTl).

Coding regions of nucleic acid molecules generated by methods of the invention will thus often be between 270 and 6,000 base pairs in length (e.g., from about 300 to about 5,000, from about 1,000 to about 5,000, from about 1,500 to about 5,000, from about 2,000 to about 5,000, from about 800 to about 4,000, from about 800 to about 3,000, from about 1,000 to about 4,000, from about 1,000 to about 2,500, from about 1,000 to about 2,000, from about 1,500 to about 5,000, from about 1,500 to about 4,000, from about 1,500 to about 3,000, etc.).

As discussed elsewhere herein, when nucleic acid molecule are used in IVTT (and/or IVTr or IVTl) reactions, it is generally seen that more protein is generated from coding regions that contain codons preferred for *Saccharomyces cerevisiae* or more generally, having a lower GC-content than codons preferred for mammalian systems. This is so even when the IVTT (and/or IVTr or IVTl) "machinery" is derived from mammalian cells (e.g., HeLa cells).

Nucleic acid molecules of the invention may contain multiple cloning sites and/or GATEWAY® recombination sites, as well as other sites for the connection of nucleic acid molecules to each other.

An exemplary list of vectors that can be used in methods of the invention, includes the following: BACULODIRECT™ Linear DIMA; BACULODIRECT™ Linear; DNA Cloning Fragment DNA; BACULODIRECT™ N-term Linear DNA_verA; BACULODIRECT™ C-Term Baculovirus Linear DNA; BaculoDirect™ N-Term Baculovirus Linear DNA; CHAMPION™ pET100/D-TOPO®; CHAMPION™ pET 101/D-TOPO®; CHAMPION™ pET 102/D-TOPO®; CHAMPION™ pET 104/D-TOPO®; CHAMPION™ pET104-DEST; CHAMPION™ pET151/D-TOPO®; CHAMPION™ pET 160/D-TOPO®; CHAMPION™ pET 160-DEST; CHAMPION™ pET 161-DEST; CHAMPION™ pET200/D-TOPO®; pAc5.1/V5-His A, B, and C; pAd/CMVA/5 DEST; pAd/PL-DEST; pAO815; pBAD/glll A, B, and C; pBAD/His A, B, and C; pBAD/myc-His A, B, and C; pBAD/Thio-TOPO®; pBAD 102/D-TOPO®; pBAD20/D-TOPO®; pBAD202/D-TOPO®; pBAD DEST49; PBAD-TOPO; PBAD-TOPO®; pBlueBac4.5; pBlueBac4.5A/5-His TOPO®; pBlueBacHis2 A, B, and C; pBR322; pBudCE4.1; pcDN3.1A/5-His-TOPO; pcDNA3.1(−); pcDNA3.1(+); pcDNA3.1(+)/myc-HisA; pcDNA3.1(+)/myc-His A, B, C; pcDNA3.1(+)/myc-His B; pcDNA3.1(+)/myc-HisC; pcDNA3.1/His A; pcDNA3.1/His B; pcDNA3.1/His C;

pcDNA3.1/Hygro(−); pcDNA3.1/Hygro(+); pcDNA3.1/NT-GFP-TOPO; pcDNA3.1/nV5-DEST; pcDNA3.1A/5-His A; pcDNA3.1A/5-His B; pcDNA3.1A/5-His C; pcDNA3.1/Zeo(−); pcDNA3.1/Zeo(+); pcDNA3.1/Zeo(+); pcDNA3.1DA/5-His-TOPO; pcDNA3.2/V5-DEST; pcDNA3.2A/5-GW/D-TOPO; pcDNA3.2-DEST; pcDNA4/His A; pcDNA4/His B; pcDNA4/His C; pcDNA4/HisMax-TOPO; pcDNA4/HisMax-TOPO; pcDNA4/myc-His A, B, and C; pcDNA4/TO; pcDNA4/TO; pcDNA4/TO/myc-His A; pcDNA4/TO/myc-His B; pcDNA4/TO/myc-His C; pcDNA4/V5-His A, B, and C; pcDNA5/FRT; pcDNA5/FRT; pcDNA5/FRT/TO/CAT; pcDNA5/FRT/TO-TOPO; pcDNA5/FRT/V5-His-TOPO; pcDNA5/TO; pcDNA6.2/cGeneBLAzer-DEST_verA_sz; pcDNA6 2/cGeneBLAzer-GW/D-TOPO pcDNA6; 2/cGeneBlazer-GW/D-TOP-O_verA_sz pcDNA6.2/cLumio-DEST; pcDNA6 2/cLumio-DE STverAsz; pcDNA6.2/GFP-DEST_verA_sz; pcDNA-DEST40; pcDNA-DEST47; pcDNA-DEST53; pCEP4; pCEP4/CAT; pCMV/myc/cyto; pCMV/myc/ER; pCMV/myc/mito; pCMV/myc/nuc; pCMVSPORT6 Notl-Sall Cut; pCoBlasi; pCR Blunt; pCR XL TOPO; pCR®T7/CT TOPO®; pCR®T7/NT TOPO®; pCR2.1-TOPO; pCR3.1; pCR3.1-Uni; pCR4BLUNT-TOPO; pCR4-TOPO; pCR8/GW/TOPO TA; pCR8/GW-TOPO_verA_sz; pCR-Blunt II-TOPO; -pCRII-TOPO; pDEST™ R4-R3; PDEST™ 10; PDEST™ 14; PDEST™ 15; pDEST™ 17; pDEST™ 20; pDEST™ 22; PDEST™ 24; pDEST™ 26; pDES™ 27; pDEST™ 32; pDEST™ 8; pDEST™ TM 38; pDEST™ TM 39; pDisplay; pDONR™ P2R P3; PDONR™ P2R-P3; pDONR™ P4-P1R; pDONR™ P4-P1R; pDONR™/Zeo; pDONR™/Zeo; pDONR™ 201; pDONR™ 201; pDONR™ 207; pDONR™ 207; pDONR™ 221; pDONR™ 221; pDONR™ 222; pDONR™ 222; pEF/myc/cyto; pEF/myc/mito; pEF/myc/nuc; pEFi/His A, B, and C; pEF1/myc-His A, B, and C; pEF1/V5-HisA, B, and C; pEF4/myc-His A, B, and C; pEF4/V5-His A, B, and C; pEF5/FRT V5 D-TOPO; pEF5/FRT/V5-DEST™; pEF6/His A, B, and C; pEF6/myc-His A, B, and C; pEF6/V5-His A, B, and C; pEF6A/5-His-TOPO; pEF-DEST51; pENTR U6_verA_sz; pENTR/Hir-TO_verA_sz; pENTR-TEV/D-TOPO; pENTR™/D-TOPO; pENTR™/D-TOPO; pHybLex/Zeo; pHyBLex/Zeo-M52; pIB/His A, B, and C; pIBA/5-His Topo; pIBA/5-His-DEST; pIBA/5-His-TOPO; pIZA/5-His; p!ZT/V5-His; pl_en!i4 BLOCK-iT-DEST; pLenti4/BLOCK-iT-DEST; pLenti4/TOA/5-DEST; pThioHis A, B, and C; pTracer-CMV/Bsd; pTracer-CMV2; pTracer-EF A, B, and C; pTracer-EF/Bsd A, B, and C; pTracer-SV40; pTrcHis A, B. and C; pTrcHis2 A, B, and C; pTrcHis2-TOPO®; pTrcHis2-TOPO®; pTrcHis-TOPO®; pT-Rex-DEST30; pT-Rex-DEST30; pT-Rex-DEST™ 31; pT-REx™-DEST31; pUB/BSD TOPO; pUB6A/5-His A, B, and C; pUC18; pUC19; pUni/V5 His TOPO; pVAX1; pVP22/myc-His TOPO®; pVP22/myc-His2 TOPO®; pYC2.1-E; pYC2/CT; pYC2/Nt A, B. C; pYC2-E; pYC6/CT; pYD1; pYES2; pYES2.1A/5-His-TOPO; pYES2/CT; pYES2/NT; pYES2/NT A, B, & C; pYES3/CT; pYES6/CT; pYES-DEST™ 52; pYESTrp; pYESTrp2; pYESTrp3; pZeoSV2(−); pZeoSV2(+); pZErO-1; and pZErO-2.

tRNA Molecules

In many instances and for purposes of illustration, methods and compositions of the invention will contain transcriptional and translational "machinery" and tRNA molecules (e.g., amino acid charged and uncharged tRNA molecules). In many instances, tRNA molecules will be used as "pools". These pools may be composed of a complete collection of tRNA molecules found within a cell (e.g., present in a cell extract) or individual tRNA molecules that are combined with each other. One example of a pool would be a mixture of twenty tRNA molecules anticodons corresponding to the twenty preferred *S. cerevisiae* codons set out in Table 15.

The invention also includes tRNA pool that may be generated by any number of methods. As implied above, tRNA pools may be generated by isolation of tRNAs from cells or expression in vitro.

When tRNAs are obtained from cells, these tRNA molecules may be naturally resident in a cell, expressed from exogenously added nucleic acid, or a combination of the two.

Methods are also available for the in vitro synthesis of charged tRNA molecules in vitro. Exemplary methods are set out in Korencic et al., "*A one-step method for in vitro production of tRNA transcripts,*" *Nature* 30:e105 (2002). These methods, in part, include transcription and amino acid charging methods that are set out similar to as follows. DNA templates were transcribed in 40 mM Tris-HCl, pH 8.0, 30 nM T7 RNA polymerase, 22 mM MgCl2, 1 mM spermidine, 0.5% Triton-X100, 5 mM DTT, 4 mM each NTP, and 5 mM GMP and for 3 hours at 37° C. tRNA molecules were prepared from the transcription reaction mixture by phenol/chloroform extraction, ethanol precipitation, followed by resuspension in sterile water. tRNA molecules were then purified by electrophoresis on a 12% polyacrylamide gel, followed by extracted from the gel. Aminoacylation reaction mixtures contained 100 mM HEPES-NaOH pH 7.2, 50 mM KCl, 10 mM $MgCl_2$, 5 mM DTT, 10 mM ATP, 30 μM [$^{14}$C]lysine (300 c.p.m./pmol), 5 μM tRNALys transcript and 500 nM Lys-tRNA synthetase for 30 minutes at 37° C.

The T7 promoter is an RNA polymerase II promoter. These promoters normally are used by cells to generate mRNA molecules. tRNA molecules are typically transcribed from DNA using RNA polymerase III promoters. Thus, in part, compositions and methods of the invention involve the intracellular and extracellular transcription of tRNA molecules using RNA polymerase III promoters (e.g., the U6 promoter, the H1 promoter, etc.).

The invention thus includes compositions and methods for the preparation of individual, charged tRNA molecules, as well as methods for using such tRNA molecules and mixtures containing such molecules. For example, invention compositions and methods for the in vitro preparation of individual, charged tRNA molecules. For example, one may prepare twenty different charged tRNA molecules and pool them for use in IVTT (and/or IVTl) reactions. One exemplary IVTT (and/or IVTr or IVTl) reaction mixture is one that contains DNA encoding a human protein, where the coding region contains only the preferred yeast codons (see Table 15) for each amino acid, a HeLa cell extract with all of the necessary components for IVTT (and/or IVTr or IVTl) reactions, and exogenously added, tRNA molecules (charged and/or uncharged), produced by in vitro synthesis, corresponding to all twenty of the preferred yeast codons.

The amounts of the exogenously added, charged tRNA molecules may be adjusted to match the codon usage of the RNA for translation. For example, if the encoded protein contains roughly equal amount of all amino acid except proline and alanine, the amount of added tRNA molecules may be adjusted accordingly. Also as an example, if the encoded protein has twice as many proline residues and half as many alanine residues as compared to the other eighteen amino acids, then the exogenously added tRNA molecules may contain equal molar amounts of all tRNA molecules except for the tRNA molecules charged with lysine and proline. The lysine charged tRNA molecules may be included at twice the molar amount of the other eighteen tRNA molecules and the proline charged tRNA molecules may be present at half the molar amount. Of course, some HeLa cell tRNA molecules will be present also and the amounts of these charged with particular amino acids and corresponding to various codons will vary.

The invention also includes IVTT (and/or IVTr or IVTl) production cells. These are cells that are engineered in a manner that allows them suitable for providing one or more components of IVTT (and/or IVTr or IVTl) reactions. One example of such a cell would be one that over-produces twenty or more charged tRNA molecules. Such a cell may be engineered to just over-produce the tRNA molecules themselves but may also be engineered to expressed increased levels of corresponding amino acid tRNA synthetases. A number of *E. coli* cells, for example have been engineered along these lines (see, e.g., Fayat et al., *Biochimie.,* 65(3): 221-5 (1983)).

In some instances, increased production of tRNA molecules has been seen to adversely affect cell growth. In other instances, no cell growth effect is seen (Ulrich and Parker, *Mol. Gen. Genet.,* 205(3):540-5 (1986)). In instances where synthesis of components of IVTT (and/or IVTr or IVTl) systems alter characteristics of cells expressing them in an unfavorable manner, IVTT (and/or IVTr or IVTl) component coding regions may be placed under the control of a regulatable promoter. Such promoters may be activated by induction or the removal of repression at a time when production of one or more (e.g., from about 1 to about 60, from about 2 to about 60, from about 4 to about 60, from about 6 to about 60, from about 1 to about 10, from about 2 to about 10, from about 4 to about 10, from about 10 to about 40, from about 10 to about 20, from about 6 to about 20, from about 8 to about 16, from about 20 to about 40, etc.) IVTT (and/or IVTr or IVTl) component is desired. For example, cultures may be maintained in "phases". For example, in Phase I cells may be cultured without expression of one or more IVTT (and/or IVTr or IVTl) component. Once a desirable cell density or number has been achieved, Phase II may be induced by the activation of cellular production of the one or more IVTT (and/or IVTr or IVTl) component.

In some instances, cells may be used that are not engineered but over-produce, for example, one or more amino acid tRNA synthetase. A number of mutant *E. coli* strains, for example, are known to have this characteristic (see Fröhler et al., *J. Bacteriol.,* 143(3):1135-41 (1980) and Theall et al., *Mol. Gen. Genet.,* 169(2):205-11 (1979)). Further, tRNA molecules and cognate tRNA synthetases may be heterologous to the cells in which they are produced. For example, Eckes et al., *Mol. Gen. Genet.* 217(2-3):263-8 (1989) demonstrated the expression of alfalfa glutamine synthetase in transgenic tobacco plants.

The invention thus includes compositions and methods that employ such mutants, as well as methods for determining the over-production mechanisms of such cells and the use of that information for the design of suitable cells for use in the practice of the invention.

Factors that may be adjusted to enhance translation in reaction mixtures are the total amount of charged tRNA molecules, the total amount of charged tRNA molecules with anti-codons corresponding to all of the codons in the RNA molecule being translated, and the amount of charged tRNA molecules with anti-codons corresponding to individual codons in the RNA molecule being translated. As an example, assume that a HeLa cell extract is used for IVTT (and/or IVTr or IVTl) of a DNA molecule encoding a human protein, where all of the codons are the most preferred yeast codons. The HeLa cell extract contains charged, human tRNA molecules based upon human cell expression and amino acid charging. An IVTT (and/or IVTr or IVTl) reaction mixture may be supplemented with twenty differ- ent, charged tRNA molecules having cognate anti-codons that match the twenty codons present in the transcribed RNA.

IVTT (and/or IVTr or IVTl) components may be derived from more than one cell. For example, transcriptional and translational "machinery" may be obtained as a cell from one cell type and supplemental IVTT (and/or IVTr or IVTl) consumables may be obtained from multiple cells. For purposes of illustration, a HeLa cell extract may be used for naturally present transcriptional and translational machinery and charged tRNA molecules In some instances, it will be desirable to use more than one codon for a particular amino acid. For example, regions of a nucleic acid molecule encoding repeats of the same amino acid in a protein may be difficult to synthesize. In such instances, it may be desirable to use more than one codon for the particular amino acid.

The invention includes IVTT (and/or IVTr or IVTl) reaction mixtures adjusted for enhanced protein production. These methods include, in part, the use of codons and tRNA molecules that match those codons in IVTT (and/or IVTr or IVTl) reaction mixtures.

38

In Vitro Transcription and Translation

In vitro transcription and/or translation (IVTT) (and/or IVTr or IVTl) may be performed by any number of means. Further, if the desired end product is an RNA molecule, then translation may not be performed. Thus, in some workflows of the invention either non-translatable RNA will be generated or translatable RNA that is not translated as part of the workflow will be generated.

Components of IVTT (and/or IVTr or IVTl) reaction mixtures typically include one or more cellular extract, one or more energy substrate, amino acids, one or more nucleic acid molecule encoding an RNA transcription template, one or more cofactor (e.g., $Mg^{2+}$), one or more buffer, one or more salt, one or more energy regenerating component (e.g., creatine phosphate and creatine kinase), nucleoside triphosphates, and nucleic acid stabilization compounds (e.g., polyamines, such as spermine and spermidine).

IVTT (and/or IVTr or IVTl) systems may be generated using the "machinery" of essentially any cell type (e.g., Neurospora crassa, human, dog, Saccharomyces cerevisiae, Eschericia coli, plant, frogs etc.). Further, a number of IVTT (and/or IVTr or IVTl) systems suitable for use in the practice of the invention are commercially available. Some such products are set out in Table 1.

TABLE 1

| THERMO FISHER SCIENTIFIC ®/Life Technologies Corp. | | | |
|---|---|---|---|
| In vitro Transcription/Translation Kits | | | |
| | Kit Name | | |
| | Retic Lysate IVT ™ Kit | 1-Step Human Coupled IVT Kit | 1-Step Human High Yield IVT Kit | 1-Step CHO High Yield IVT Kit |
| Source | Rabbit reticulocyte | HeLa lysate | HeLa lysate | CHO (Chinese hamster ovary) lysate |
| Yield | Low | Medium | High | High |
| Protein modifications | Limited glycosylation | Glycosylation and phosphorylation | Glycosylation and phosphorylation | Glycosylation and phosphorylation |
| Reaction time | 90 min | 90 min to 6 hr | 6-24 hr | 6-24 hr |
| Catalog No. | AM1200, AM1200M | 88881, 88882, 88883, 88884 | 88890, 88891, 88892 | 88893, 88894 |

Cell extracts contain many of the compounds that are either required for or enhance the activity of IVTT (and/or IVTr or IVTl) reactions. Cell extracts contain, for example, polymerases, ribosomes, tRNAs, aminoacyl-tRNA synthetases, initiation, elongation and termination factors, amino acids, compounds that effectively act as buffers (e.g., proteins), nucleoside triphosphates, and energy molecules such as ATP, GTP and NADH.

While cell extracts contain most of the components necessary for in vitro transcription and coupled in vitro translation/transcription reactions, supplementation is often desirable to enhance production of template RNA and/or protein.

Further, a number of isolates of cellular tRNAs are commercially available. These include yeast tRNA molecules (Life Technologies Corp., Cat. No. AM7119), wheat germ tRNA molecules (bioWORLD, a division of GeneLinx International, Inc., Cat. No. 11020002-1), and E. coli tRNA molecules (Roche Life Science, Cat. No. 10109541001).

IVTT (and/or IVTr or IVTl) reaction mixtures may be prepared from essentially any cell type. These reaction mixtures will typically be composed of an extract of one or more cell type and additional reagents for enhancing transcription and/or translation reactions. In some embodiments, an IVTT (and/or IVTr or IVTl) reaction mixture may be prepared as follows. Cells are obtained (e.g., after culturing or from an organism), the cells are then lysed (e.g., in a lysis buffer), cellular debris is removed, cellular DNA is removed, and one or more reagents are then optionally added.

One formulation for use in IVTT (and/or IVTr or IVTl) using E. coli lysates is as follows: E. coli S30 cell lysate, HEPES-KOH (pH 8.2), 80 mM ammonium acetate, 200 mM potassium glutamate, 2.7 mM sodium oxalate, 1.76 mM DTT, 0.67 mM cyclic-AMP, 34 μg/ml folinic acid, 340 μg/ml tRNAs, 0.33 mM NADH, 0.27 mM Coenzyme A, 1.2 mM ATP, 0.86 mM CTP, GTP, and UTP, 2% (w/v) PEG-8000, 2 mM methionine, 0.5 mM each of the other 19 amino acids, 33 mM phosphoenol pyruvate, 15 mM magnesium acetate, 10 μg/ml rifampicin, and 30 μg/ml T7 RNA polymerase. (Iskakova et al., *Nucl. Acids, Res.,* 34:e135 (2006).)

Reagents present in IVTT (and/or IVTr or IVTl) reaction mixtures may differ based upon the particular system being employed. For example, rifampicin has been shown to induce of RNA polymerase beta and beta' subunit synthesis in in vitro coupled system of transcription and translation as well as an in vitro transcription system with purified RNA polymerase holoenzyme. (Fukuda et al., *J Biol. Chem.,* 258:2720-2728 (1983).) While rifampicin may be included in IVTT (and/or IVTr or IVTl) systems employing eukaryotic cell lysates, it will often be excluded in systems employing appropriate prokaryotic cell lysates (e.g., E. coli lysates).

E. coli has over 80 tRNA genes, yeast have about 295 and humans have over 500 tRNA genes. It has been shown that these numerous tRNA genes have functions in the regulation of gene expression. Through monitoring of the cellular aminoacylation status for all tRNAs and determination of global changes in post-transcriptional RNA modification patterns it has been shown that stress and other stimuli lead to changes in the expression levels, aminoacylation status, and modification patterns of specific tRNAs, which in turn leads to changes in gene expression at the translation level. (Commented on in Ibba, *"Transfer RNA comes of age,"* RNA 21: 648-649 (2015).) Thus, not only does preferred codon usage correlate with increased protein expression, cellular content of tRNAs appear to change within cells presumably changing what is considered to be a "preferred codon" from a tRNA perspective.

In many aspects of the invention, these cellular aspects of codon content and usage are either avoided or employed in the practice of the invention. In other words, two foci of the invention are ease of nucleic acid production and efficient protein expression. Further, physiological changes within cells and cells that are exposed to may be controlled to alter protein expression levels in methods of the invention.

It has been shown that cellular stress responses result in intracellular changes to tRNA modifications and tRNA levels. For example, it has been shown that stress-induced changes in tRNA levels occur in *Saccharomyces cerevisiae* when placed under oxidation ($H_2O_2$) and alkylation (methylmethane sulfonate, MMS). In particular, 18 tRNAs showed opposing changes for the stresses. (Pang et al., *"Diverse cell stresses induce unique patterns of tRNA up- and down-regulation: tRNA-seq for quantifying changes in tRNA copy number",* Nucl. Acids Res., 10.1093/nar/gku945 (2014).) It has been shown that cells can respond to different stresses by the reprogramming of tRNA wobble modifications resulting in the selective translation of mRNAs of gene family members for different stress responses. Thus, the invention includes methods where cells are exposed to one or more stress to alter intracellular tRNA levels, extracts of those cells (stress extracts) are then generated and used in IVTT (and/or IVTr or IVTl) reactions. The invention further includes methods for producing proteins using mRNA that contains codons optimized to correspond to tRNA molecules present in stress extracts.

One issue with many IVTT (and/or IVTr or IVTl) systems is that reactions proceed quickly for the first 20 minutes or so, then rapidly slow down. Some commercial kits have been designed to allow for efficient reaction rates for a substantially longer period of time. One such commercial product is the "1-Step Human High Yield IVT Kit" available from Thermo Fisher Scientific® (Cat. No. 88890). This kit allows for IVTT (and/or IVTr or IVTl) reactions to proceed for an extended period of time with substantial production of mRNA and encoded protein.

The invention thus includes methods that include IVTT (and/or IVTr or IVTl) reactions that occur over a specified period of time. Incubation periods may extend from about 20 minutes to about 48 hours (e.g., from about 30 minutes to about 48 hours, from about 1 hour to about 48 hours, from about 2 hours to about 48 hours, from about 3 hours to about 48 hours, from about 4 hours to about 48 hours, from about 6 hours to about 48 hours, from about 8 hours to about 48 hours, from about 6 hours to about 36 hours, from about 8 hours to about 36 hours, from about 12 hours to about 36 hours, from about 12 hours to about 30 hours, from about 18 hours to about 30 hours, from about 12 hours to about 24 hours, etc.).

Once protein has been produced, it may be quantified using any number of means. One quantification method is Western blot. In this method, proteins are typically run separated by gel electrophoresis, then transferred to a membrane, and specific proteins are identified by antibody binding. Methods for quantifying protein in Western blots include methods that employ fluorescent, chemiluminescent, and colorimetric labels. Some quantification methods involve the use of secondary antibodies coupled to fluorophores. One advantage of the use of a fluorophores is that no substrate is required. The amount of a specific protein produced in an experimental run can be determined using a number of commercially available kits (e.g., SuperSignal™ West Dura Extended Duration Substrate, Cat. No. 34075 and Pierce™ ECL Western Blotting Substrate, Cat. No. 32109. Similar detection methods are set out in Alegria-Schaffer A., Lodge A., Vattem K., *Methods Enzymol.* 463:573-599 (2009).

Other assays that may be used to quantify the amounts of particular proteins generated in IVTT (and/or IVTl) systems include direct and indirect ELISAs. One technique popularly known as competitive ELISA is routinely used to quantitate the concentrations of unknown Histidine tagged proteins. In this assay, a His-tagged protein is pre-coated on to a solid support, such as a microwell plate. Series dilutions of poly-Histidine tagged protein standards and unknown samples are then added to each test well, then, an anti-His tag antibody is added to the solid support. His-tagged target protein in solution and pre-coated His-tagged protein compete to bind the antibody. After washing steps, a labeled secondary antibody (e.g., HRP-conjugated secondary antibody) is added to each well to react with anti-His tag antibody. Where appropriate, the next step involves the addition of a substrate (e.g., a TMB substrate), followed by the addition of stop solution for signal development and detection. When a colorimentric substrate is used, for example, the optical density reading will indicate expression level of His-tagged proteins. His-tagged protein in the sample may be semi-quantified by comparing to the standard curve generated from known His-tagged protein (see, e.g., His Tag ELISA Detection Kit, GenScript, Inc., Cat. No. L00436).

Methods that may be used for the quantification of protein include those based upon the measurement of absorbance of ultraviolet light (UV). Quantitation of the amount of protein present in a solution is possible in through the use of spectrophotometry. Absorption of radiation in the near UV by proteins depends mainly on tyrosine and tryptophan content and to a smaller extent on the amount of phenylalanine and the presence of disulfide bonds. The $A_{280}$ thus can varies greatly between different proteins with, for a 1 mg/mL solution, the $A_{280}$ being from 0 up to 4. However, most protein values fall in the range of 0.5-1.5.

While susceptible to chromophore interference, this method is simple and also non-destructive to the sample. Two additional disadvantages are that accurate quantitation requires that the specific absorption value at 280 nm be known and nucleic acids also absorb fairly strongly at this wavelength.

Peptide bonds absorb strongly in the far ultraviolet with maximum absorption at about 190 nm. Because of the difficulties caused by absorption by oxygen at this wavelength, measurements are more conveniently made at 205 nm. However, the absorbance of peptide bonds is about half that of 205 nm than at 190 nm. While some groups of specific amino acid (e.g., tyrosine, tryptophan, etc.) absorb light at 205 nm, most proteins have extinction coefficients at 205 nm for a 1 mg/mL solution of between 30-35 and between 20 and 24 at 210 nm.

The invention thus includes methods for the semi-quantification and quantification of proteins using absorption of ultraviolet light, in particular at wavelengths from about 180 nm to about 300 nm (e.g., from about 190 nm to about 280 nm, from about 190 nm to about 275 nm, from about 190 nm to about 260 nm, from about 190 nm to about 250 nm, from about 190 nm to about 250 nm, from about 190 nm to about 240 nm, from about 190 nm to about 230 nm, from about 180 nm to about 220 nm, from about 190 nm to about 220 nm, from about 190 nm to about 210 nm, from about 200 nm to about 210 nm, from about 200 nm to about 280 nm, from about 210 nm to about 280 nm, from about 220 nm to about 280 nm, from about 230 nm to about 280 nm, from about 240 nm to about 280 nm, from about 250 nm to about 280 nm, from about 260 nm to about 280 nm, from about 210 nm to about 255 nm, from about 220 nm to about 250 nm, etc.).

Devices

The invention provides devices for performing methods of the invention. Devices of the invention may perform any number of methods related to work flows of the invention. As an example, a device of the invention may be designed to accept amino acid sequence data by any number of means. For example, amino acid sequence data (as well as nucleotide sequence data) may be entered by an operator keying in the sequence via a keyboard, touch screen display or other manual entry method. Further, an operator may enter sequence data by way of an external drive (e.g., a hard drive) or through a connection (e.g., a network or internet connection).

Software used in devices of the invention may be designed to use sequence data (nucleotide and amino acid sequence data) in any number of format, including FASTA, AB1, VCF, MBL, FASTQ, BAM, SAM, and GenBank formats.

Devices of the invention will thus include both hardware and machine instruction components (e.g., software).

When nucleotide sequence data is entered, open reading frames may be identified and selected by the operator. Additional parameters may also be selected such as the addition of 5' and/or 3' untranslated and coding region flanking sequences and amine and/or carboxy terminal amino acid sequences. One example of a linear construct showing 5' and/or 3' flanking sequences is set out in FIG. 12.

Examples of flanking nucleic acid regions are promoters, activator binding sites, repressor binding sites, operators, internal ribosome entry sites, polyA sequences, polyA signals, restriction sites, topoisomerase sites, primer binding sites, splice sites, recombination sites (e.g., GATEWAY™ recombination sites, lox sites, etc.) and nucleic acid encoding protein components (e.g., affinity tags, inteins, proteolytic cleavage sites, selectable markers, etc.).

Once various parameters of the nucleic acid molecule has been selected, including any polypeptide expression product and characteristics thereof, the device (e.g., mechanical device) designs and begins to synthesize and, if appropriate, assemble the nucleic acid molecule using, for example, methods set out elsewhere herein. During the design process, the device may choose and/or weigh parameters such as codon usage, hairpin structure formation, oligonucleotide junction sited (e.g., for "uniqueness" and hybridization efficiency), and assembly efficiency (e.g., GC content), as well as other parameters.

Once oligonucleotides are synthesized, the device may be directed to assemble these oligonucleotides into larger nucleic acid molecules (see, e.g., FIG. 9). One method for assembly of oligonucleotides is based upon filing in gaps using polymerases. Other assembly methods employ PCR. The device will thus contain at least one reaction site for at least one type of assembly process and, in many instances, will have the ability to perform thermocycling.

Once an assembled nucleic acid molecule of desired size and content is generated, the assembled nucleic acid molecule may be used directly in an IVTT (and/or IVTr or IVTl) reaction (as a linear nucleic acid molecule) or may be first introduced into a vector. Further, the vector may be synthesized in its entirety. When the vector is not fully synthesized by the device, then the vector backbone will often be introduced into the device.

After a nucleic acid molecule has been generated, the device may direct that this molecule be used in an IVTT (and/or IVTr or IVTl) reaction. This may occur at the location where the nucleic acid molecule was assembled or at a different location.

Once a protein is produced, this protein may be removed from the device along with the IVTT (and/or IVTr or IVTl) reaction mixture or may be separated from the reaction mixture first. Any number of means may be used to separate the protein from the IVTT (and/or IVTr or IVTl) mixture (e.g., affinity purification) but one means is by the use of a purification tag (e.g., an affinity). Purification tags may be produced in the IVTT (and/or IVTr or IVTl) reaction mixture and may be coded for by the assembled nucleic acid molecules. Exemplary purification tags include fluorescent protein (e.g., GFP), V5, Myc, human influenza hemagglutinin (HA), FLAG, thioredoxin (TRX), poly(NANP), chitin binding protein (CBP), maltose binding protein (MBP), glutathione-S-transferase (GST), and poly(His) tags.

Proteins may be purified by any number of means using such tags. One method for protein purification is via affinity association (e.g., affinity chromatography, binding to beads, such as magnetic beads, etc.).

Polyhistidine tags, for example, are typically a sequence of five to nine histidine amino acids (SEQ ID NO: 4) normally attached to a terminus of a target protein (see FIG. 12). The polyhistidine tag is purified using immobilized metal affinity chromatography (IMAC). For histidine tag purification, either nickel or cobalt is immobilized onto a solid support (e.g., a bead). While the two metals can be used interchangeably, typically nickel has a higher binding capacity whereas cobalt binds less non-specific protein to deliver a purer final protein.

Once immobilized, a compound such as imidazole is used to disrupt the charge attractions between the immobilized metal affinity chromatography resin and the histidine-tagged protein. In most instances, the released histidine-tagged protein can be easily cleaned-up using a desalting column or dialysis cassette to remove imidazole.

Magnetic beads suitable for the purification of His tagged proteins are commercially available (e.g., THERMO FISHER SCIENTIFIC®, Cat. No. 88831).

Glutathione S-transferase (GST) is a 26 kDa endogenous enzyme found in both prokaryotes and eukaryotes. GSH is an endogenous tripeptide (Glu-Cys-Gly) containing a cysteine residue, whose sulfhydryl side chain functions as a reducing agent. Often GST is a good affinity tag because of its strong binding to reduced glutathione. GST possess numerous tyrosine residues in the in the GSH binding pocket, and one of these tyrosines hydrogen bonds to the substrate glutathione forming a stable complex.

Typically proteins that are purified by these methods are expressed as fusion proteins containing an amino acid sequence that binds to glutathione. Also, glutathione magnetic beads are commercially available for the purification of GST tagged proteins (e.g., THERMO FISHER SCIENTIFIC®, Cat. No. 88821).

Figure 2:
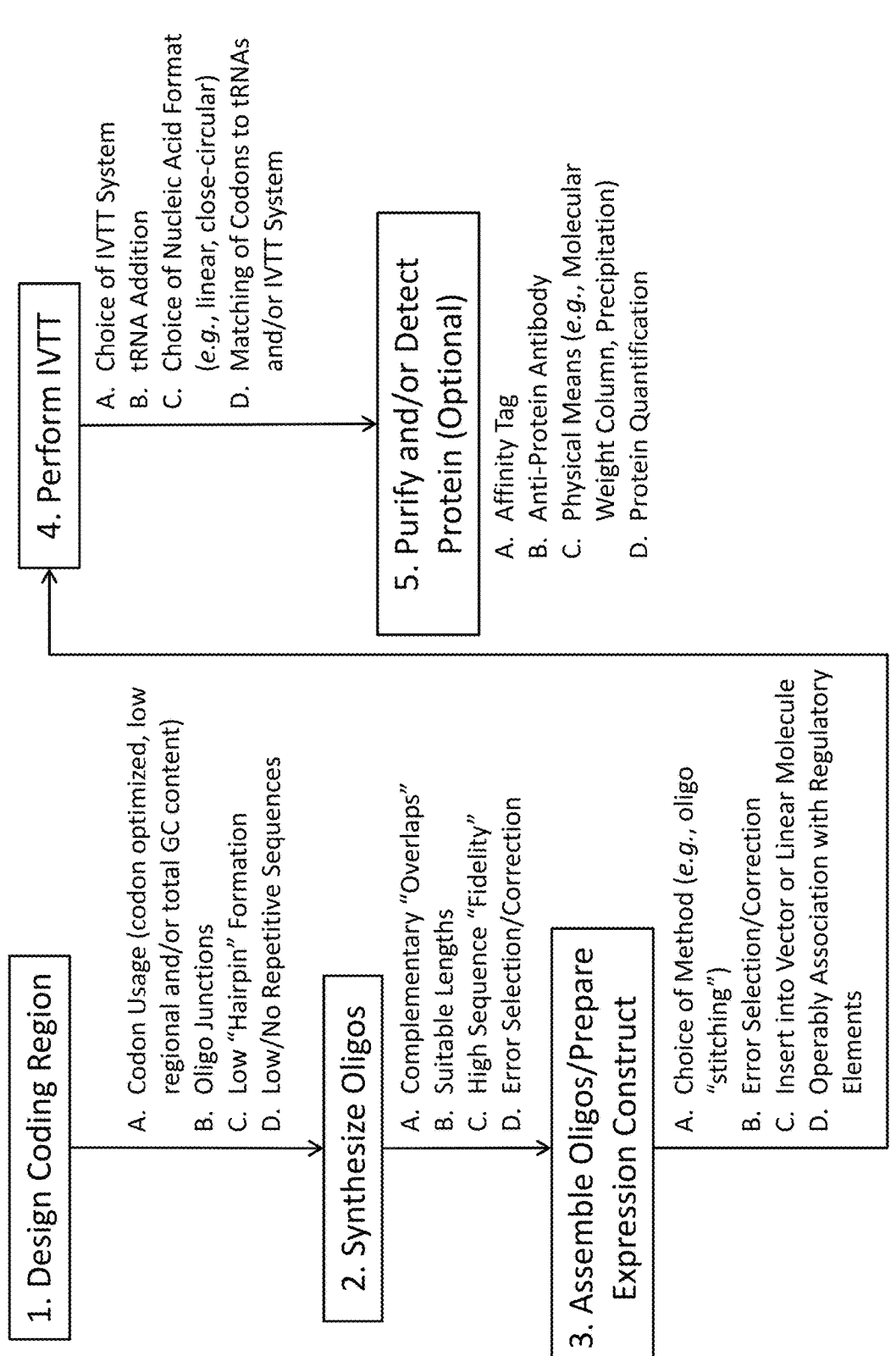
FIG. 2 shows a more specific overview of some aspects of workflows of the invention.

The device may additional perform processes set out in FIGS. 1 and 2, as well as have software and hardware components suitable for performance of these methods.

The device may be operated as a "sealed unit" or may be designed to allow for the removal of various molecules generated by the device (e.g., oligonucleotides, partially assembled nucleic acid molecules, fully assembled nucleic acid molecules, plasmids containing assembled nucleic acid molecules, proteins, etc.). Thus, aliquots may be removed during the device "work flow". In this sense, devices of the invention may be used as DNA synthesizers and may also be used to generate replicable nucleic acid molecules (e.g., vectors).

In many instances, the device will be designed to store reagents and collect waste products. For example, reservoirs (internal or external) may be present containing reagents for the various steps in nucleic acid synthesis. Additionally, reservoirs may also be present that contain nucleic acid molecules. As an example, topoisomerase adapted vectors may be contained in a reservoir and assembled nucleic acid molecules may be designed to be introduced into such vectors.

Reagents storage locations (e.g., reservoirs) and reaction sites may be maintained at controlled temperatures. For example, cellular extracts may be introduced into the device in frozen form. These cellular extracts may then be brought to liquid form and maintained at a temperature below ambient temperature (e.g., 4° C.) until used in IVTT (and/or IVTr or IVTl) reactions. During the IVTT (and/or IVTr or IVTl) reactions, reactants may be transferred to a reaction site, where the temperature is maintained at a new desired temperature (e.g., 25-32° C.).

Devices of the invention will typically contain one or more of the following: reaction sites, mixing devices, solid support (e.g., controlled pore glass), fluid channels, reagent reservoirs, temperature controllers, waste collection sites, valves (e.g., computer controlled valves), and pumps (e.g., computer controlled pumps). In many instances, the device will employ software that will direct reagent flows to desired locations (e.g., reaction sites), incubation times, temperatures at various locations (e.g., fluid channels, reaction sites, waste collection sites, reagent reservoirs, etc.).

The invention also includes devices designed to perform part of the workflows of the invention (e.g., the workflow set out in FIGS. 1 and 2). For example, the workflow set out in FIG. 2 may be entered at Step 2. In such an instance, the coding region would have been designed externally from the claimed device and then entered into the device for oligonucleotide synthesis. Similarly, the workflow set out in FIG. 2 may be entered at Step 3. In such an instance, the oligonucleotides would be synthesized externally from the claimed device and then introduced into the device for assembly. In many such instances, error correction would be performed prior to introduction of the oligonucleotides into the device.

One method for the purification of GST tagged protein from the IVTT reactions that has been used in the practice of the invention involves PureCube Glutathione MagBeads (Cube Biotech, cat. no. 32205), similar to as set out below. PureCube Glutathione MagBeads may be prepared either in 2 ml Eppendorf tube or HDW 96 plates, with U-Profile for high-throughput protein purification. PureCube Glutathione MagBeads are briefly vortexed in their original bottle to obtain a homogeneous suspension. 100 μl of PureCube Glutathione MagBeads are then mixed with 100 μl of binding buffer. A magnetic separation rack is used to separate the beads from the liquid phase, which is then discarded. The beads are then resuspended in 200 μl of binding buffer, separated from the supernatant on a magnetic rack and the supernatant is again discarded. This washing step is repeated twice. The washed beads are then immediately mixed with the solution containing the protein to be purified, to avoid beads drying.

For purification of GST tagged proteins with PureCube Glutathione MagBeads, 110 μl of IVTT reaction are mixed with 330 μl of binding buffer and after a brief incubation the mix is added to the previously washed magnetic beads. For manual beads preparation, single 2 ml Eppendorf tubes with U-shape can be used. For automated beads preparation in a TECAN liquid handling system, in 1.2 ml 196-well U-Profile HDW 96 plates can be used. After carefully closing the tubes, or after heat-sealing of the HDW 96 plate, the samples are incubated over night at 4° C. in an overhead shaker. The reaction vessels (tubes or 96-well plate) are then put on a magnetic separator to collect the beads and the supernatant is discarded. Alternatively, a suitable volume of the supernatant may be analyzed in a SDS PAGE to determine binding efficiency. The magnetic beads are then washed with 400 µl of wash buffer and, after a 5 minute incubation at room temperature, the supernatant is discarded. This step is repeated two more times.

50 µl of elution buffer is then added to the beads and, after a 15 minute incubation at room temperature, the reaction vessels are placed on a magnetic separator. The supernatant containing the purified protein is then collected and the beads are discarded. Alternatively, the magnetic beads can be re-dissolved in water. This elution step is repeated and the eluted fractions are finally pooled. After the beads are spun down, a suitable volume of the boiled supernatant may be analyzed on a SDS PAGE to determine elution efficiency.

TABLE 2

| GST Tagged Protein Purification Buffers | | | |
| --- | --- | --- | --- |
| | Stock | Concentration | Amount |
| Binding Buffer | | | |
| Tris | 1000 mM | 125 mM | 1,250 ml |
| NaCl | 2000 mM | 150 mM | 0,750 ml |
| DTT | 100 mM | 1 mM | 0,100 ml |
| EDTA | 100 mM | 1 mM | 0,100 ml |
| ddH$_2$O | | | 7,800 ml |
| | | | 10,000 ml |
| Wash Buffer | | | |
| Tris | 1000 mM | 125 mM | 1,250 ml |
| NaCl | 2000 mM | 1000 mM | 5,000 ml |
| DTT | 100 mM | 1 mM | 0,100 ml |
| EDTA | 100 mM | 1 mM | 0,100 ml |
| ddH$_2$O | | | 3,550 ml |
| | | | 10,000 ml |
| Elution Buffer | | | |
| Tris | 1000 mM | 125 mM | 0,250 ml |
| NaCl | 2000 mM | 150 mM | 0,150 ml |
| DTT | 100 mM | 1 mM | 0,020 ml |
| Glutathione | | 50 mM | 30 mg |
| ddH$_2$O | | | 1,580 ml |
| | | | 2,000 ml |

In order to eliminate the reduced Glutathione present in the elution buffer, the eluted protein is dialyzed against 20 mM Tris-HCl, 150 mMNaCl pH 7.5 using Xpress Equilibrium Dialyzer ED300 6-8 kDa (Scienova, cat. no. 40893). The purified protein is loaded in the left opening and the outer dialysis buffer is filled in the right opening. Dialysis is performed at 4° C. for 1 hour with gentle shaking (e.g., in a thermomixer at 300 rpm). The outer buffer is then discarded and replaced through new dialysis buffer and dialysis is performed at 4° C. with gentle shaking for one additional hour. The purified dialyzed protein is then removed from the left opening and is ready for use.

Screening Methods and Nucleic Acid Isolation

The invention also includes compositions and methods for the identification of nucleic acid molecules that encode proteins of interest. A series of exemplary workflows that may be used in the practice of the invention are set out in FIG. 23. These workflows are broken out in a series of parts. Part 1 relates to the selection, design, generation, and/or isolation of the nucleic acid molecules. Part 2 relates to the formation of an array of the individual nucleic acid molecules. This may be optional because, for example, an array may be formed as part of methods performed in Part 1. Part 3 relates to IVTT reactions designed to generate proteins encoded by isolated nucleic acid molecules generated in Part 1. Part 4 relates to the detection of one or more proteins of interest. Part 5 relates to the identification nucleic acid molecules that encode the one or more proteins of interest, as well as isolation of that nucleic acid and downstream processing (e.g., sequencing, cloning).

Part 1

Figure 23:
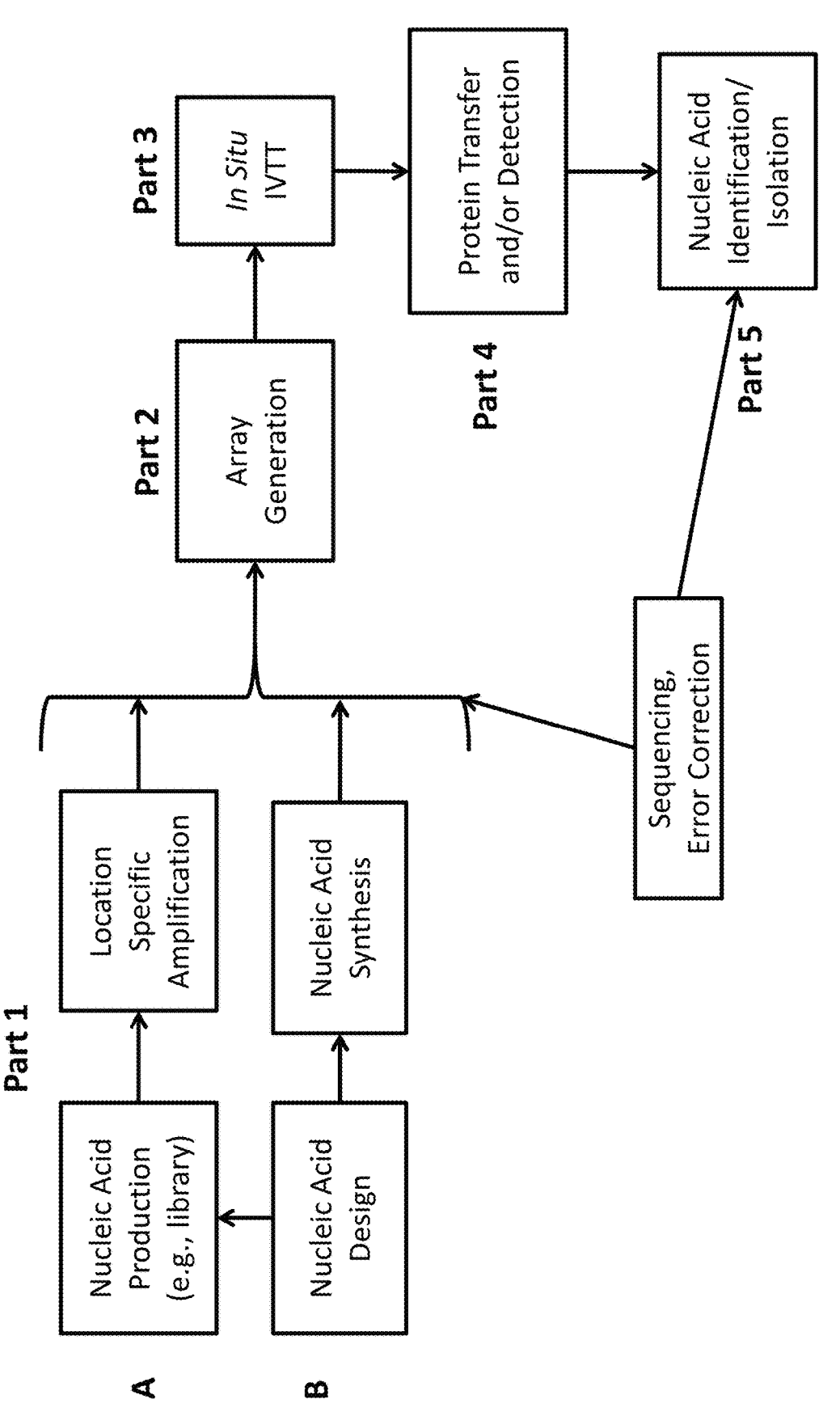
FIG. 23 shows a series of exemplary workflows of the invention. These workflows are broken up, for the purpose of illustration, into five parts, with some of the parts being optional.

With respect to Part 1 of the workflow shown in FIG. 23, typically the starting point will be a desire to obtain nucleic acid molecules encoding one or more proteins of interest. Nucleic acid molecules may encode, as examples, one or more specific proteins of an organism or one or more modified forms of a specific protein (e.g., an enzyme).

In the upper portion of Part 1 (A), a collection of nucleic acid molecules, such as a library (e.g., a cDNA library, a genomic library or a synthetic library), is prepared. Libraries may be made by standard means known in the art. For example, mRNA may be isolated from a human cell and reverse transcribed to form cDNA. The collection of nucleic acid molecules may represent all of the nucleic acid in a cell or tissue or may represent a subset thereof (e.g., a cDNA library representing expression products, typically present in the library corresponding roughly to the prevalence of mRNA present within the cell or tissue).

In certain embodiments, random or directed molecular evolution technologies, recombination-based or combinatorial strategies may be used to generate synthetic libraries encoding engineered proteins with improved or new structural or functional features (such as modified substrate or binding specificity or affinity, enantioselectivity, solubility, heat stability etc.) that can be identified by subsequent screening methods. Random sequence diversity (including point mutations, insertions or deletions) along a nucleic acid molecule may be introduced by physical or chemical mutagens or error-prone PCR as described, e.g., in McCullum et al. ("Random mutagenesis by error-prone PCR", Methods Mol Biol. 2010; 634:103-9). Error rates can be increased in a number of ways such as by introducing a small amount of Mn$^{2+}$ to replace the natural Mg$^{2+}$ cofactor and by including biased concentrations of dNTPs or by adding dNTP analogues as reviewed in Neylon C. ("*Chemical and biochemical strategies for the randomization of protein encoding DNA sequences: library construction methods for directed evolution*", *Nucl. Acids Res.*, 2004, Vol. 32, No. 4, p. 1448-1459).

Where randomization of selected regions or positions within a nucleic acid sequence is desired, pre-randomized cassettes or synthetic oligonucleotides carrying the desired mutations may be combined with or incorporated into unmodified sequence parts using standard PCR-based methods or restriction-enzyme cleavage-based cloning techniques.

One way of constructing a synthetic library with a defined level of randomization at one or more nucleotide positions is by using degenerated oligonucleotides. A nucleotide position within a nucleic acid sequence is considered degenerate if it contains a pre-defined ratio of nucleotides A and/or C and/or T and/or G, or only 2 or 3 nucleotides. Degeneracy may be limited to individual nucleotide positions or one or more codons and can be introduced within limited sequence regions or along the length of a gene. Such controlled randomization allows for exact fine tuning of the average number of mutations per construct. One way of achieving this is to introduce degenerated nucleotides or codons into a target sequence (e.g., representing a wild type or consensus sequence) via degenerated oligonucleotides using overlap extension PCR (as described, e.g., in WO 2009/146892 or WO 2010/144103). If independent regions within the same target sequence are to be mutated or randomized, separate PCR reactions with multiple degenerated mutagenesis primers may be performed and the resulting fragments may be combined in a subsequent fusion PCR reaction to assemble the full-length sequence. Such libraries may contain up to $1 \times 10^{11}$ different molecules. To improve the quality of synthetic libraries, an error correction step as described in Currin A. et al. ("SpeedyGenes: an improved gene synthesis method for the efficient production of error-corrected, synthetic protein libraries for directed evolution", Protein Eng. Des. Sel. 2014 September; 27(9):273-80) may be used.

To randomize a codon to encode all 20 amino acids (an approach know as saturation mutagenesis), a mixture of all four bases is required at the first two positions and at least three bases in the third position which can be achieved by using NNN or NNB codons (where N=A/C/G/T and B=C/G/T). To decrease the chances of introducing a premature stop codon, reduced codon sets like NNS and NNK codons are often used (wherein S=C/G, and K=G/T). Methods and compositions for site saturation mutagenesis are described, e.g., in U.S. Pat. Nos. 6,171,820, 6,764,835, and 6,562,594). Separately synthesized oligonucleotides with degenerated positions or codons may also be mixed at certain ratios to achieve a desired degree of randomization. Mixtures of degenerated oligonucleotides are also used in a method referred to as "walk-through mutagenesis", where each amino acid in one or more predefined regions is substituted by one or more predetermined amino acids without saturation.

To overcome the bias often introduced by degenerate codons such as NNN (leading to an overrepresentation of those amino acids encoded by multiple codons such as, e.g., serine), improved randomization schemes such as MAX technology (described in WO 00/15777 and WO 03/106679) may be used. This method uses single stranded templates containing NNN triplets at those positions to be randomized. Specific phosphorylated oligonucleotides encoding the desired codons are annealed to the template strand and ligated to generate double stranded constructs with defined randomized positions. This method results in equal probabilities for all 20 amino acids (or for some predetermined subsets thereof) without encoding stop codons.

Codon bias can also be avoided by using pre-defined trinucleotide phosphoramidite ("trim") building blocks during oligonucleotide synthesis to couple one codon at a time. The trim technology is described, e.g., in U.S. Pat. No. 5,869,644 and may be useful if an unequal distribution of certain amino acids (represented at a pre-defined percentage) is desired.

Another strategy to avoid codon bias is the classical "split-mix" approach developed by Merrifield, R. B. (1963 J. Am. Chem. Soc. 85, 2149), where a sample of bead-bound oligonucleotides is divided into equal portions during solid phase synthesis and each of these are individually reacted with one or more single different phosphoramidite encoding a pre-defined amino acid. After the coupling reaction the individual portions are recombined, mixed and divided again into portions and the steps are repeated as necessary.

Other known methods for introducing diversity include DNA shuffling which is based on recombination of sequences with high homology as described, e.g., in U.S. Pat. Nos. 5,605,793, 5,830,721 and 6,506,603; StEP (staggered extension process) technology described in U.S. Pat. Nos. 6,153,410 and 6,177,263, or methods known as RACHITT or ITCHY, all of which are based on generating new sequences by combining existing fragments from different sources (for an overview see Neylon C., "Chemical and biochemical strategies for the randomization of protein encoding DNA sequences: library construction methods for directed evolution" (Nucl. Acids Res., 2004, Vol. 32, No. 4, p. 1448-1459).

All of the aforementioned techniques may be used to design, construct and synthesize libraries that may be used in embodiments of the invention. Library members encoding the desired protein variants may further be combined with 5'- and 3'-UTR functional regions as described elsewhere herein, and may be provided with primer binding sites for amplification and one or more tag sequences comprising adaptor sequences and/or barcodes or unique identifiers for subsequent sequencing reactions to identify the sequence encoding a selected protein variant.

Location specific amplification may be used to produce additional copies of nucleic acid molecules or library members intended to encode identical polypeptides. The goal here will generally be to obtain multiple copies of a nucleic acid molecule that encode a protein. Of course, in some instances, the amplification process may introduce errors during the amplification process. Thus, some variations in coding sequence may be present.

In some embodiments, amplification may be conducted in solution and once the nucleic acid molecules are generated, they may be attached to a support (e.g., the surface of a well of a multiwell plate, a bead, etc.). Methods for attaching nucleic acid molecules to supports are known in the art. Such methods include the following. Amine modified nucleic acid molecules may be covalently linked to surface bound activated carboxylate or succinimidyl groups, Thiol-modified nucleic acid molecules may be covalently linked to surface bound by the use of an alkylating reagent, such as an iodoacetamide. Further, biotin-modified nucleic acid molecules can be captured by surface immobilized streptavidin which is resistant to organic solvents, denaturants, detergents, proteolytic enzymes and extremes of temperature and pH.

In other embodiments, a double stranded nucleic acid molecule may be denatured (e.g., by heating) and the denatured single stranded nucleic acid molecule (the "template") may be attached to a support by hybridization to one or more capture primers immobilized on the support (e.g., the surface of a well or a bead). Capture primers may be immobilized directly or indirectly by methods described above (e.g., by using streptavidin-coated beads to capture biotin-labeled capture primers). The hybridized templates may then be clonally amplified to generate multiple identical copies of individual library members ("amplicons"). Clonal amplification of nucleic acid templates can be achieved by any means known to those of skill in the art. In some instances, clonal amplification can comprise spatial separating individual templates and performing amplification of the separated templates. One method that may be used to obtain multiple copies of spatially separated individual nucleic acid molecule where each nucleic acid molecule encodes a single protein is by emulsion PCR. Emulsion polymerase chain reaction (PCR) is a single-molecule PCR that occurs in "cell-like" compartments. In simple terms, Emulsion PCR is used to amplify individual DNA molecules in aqueous droplets within an oil phase. Further, these amplified nucleic acid molecules may be localized on beads. Emulsion PCR methods are set out in U.S. Pat. Nos. 7,947,477 and 9,121, 047.

A variation of emulsion PCR that may be useful in methods of the invention uses magnetic capture beads and is referred to as "BEAMing" (beads, emulsions, amplification, and magnetics). BEAMing keeps amplification products formed within each compartment together once the emulsions are broken up. This can be accomplished through inclusion of magnetic capture beads within the compartments and ensuring that only one template nucleic acid molecule is contained in each compartment such that after amplification each bead is coated with multiple copies of a single type of nucleic acid molecules and can be isolated by magnetic force. The concentration of library molecules in the emulsion is critical and is adjusted so that only about 20% of the capture beads are loaded with nucleic acid. If higher concentrations are used, individual beads may receive more than one nucleic acid molecule resulting in nonclonal amplicons. To separate amplicon-carrying beads from empty beads, the capture beads may be enriched, e.g., by using larger enrichment beads (e.g. polystyrene beads) comprising a tag complementary to a universal sequence contained in the 3'-end of the capture-bead immobilized amplicons. The capture beads are then recovered by density centrifugation. Examples of compositions and methods for BEAMing are described in Dressman et al., PNAS, 100, 8817 (2003), in Diehl et al., Nat. Methods 2006, 3, 551-559, and in U.S. Pat. No. 8,715,934. Alternatively, where nonmagnetic capture beads are used for amplicon generation, enrichment beads may be magnetic and coated (e.g., with streptavidin) to specifically bind labeled (e.g., biotinylated) amplicons on the capture beads. The bead aggregates can then be extracted using magnetic force.

Another method allowing for monoclonal amplification of nucleic acid templates on solid support(s) is referred to as "bridge amplification". This method comprises attachment of single stranded template molecules equipped with 5' and 3' primer binding sequences ("first and second adaptors") by hybridization to complementary first and second (forward and reverse) capture primers immobilized on a solid support to generate a population of support-bound amplicons. In the hybridization step, the first adaptor of the template hybridizes with a first (forward) capture primer, and a primer extension reaction extends the first capture primer along the hybridized template to generate a first capture primer extension product having a complementary sequence of the second adaptor at one end. Upon removal of the template (e.g., by denaturation) the first capture primer extension product bends so that the second adaptor sequence can hybridize to a nearby second (reverse) capture primer followed by a primer extension reaction that extends the second capture primer to generate a second capture primer extension product having a complementary sequence of the first adaptor at one end, and forming a double-stranded bridge molecule. The double-stranded bridge structure is denatured to yield two single-stranded, immobilized template molecules, each of which has a free end that allows for hybridization of the contained adaptor sequence to another support-bound capture primer for subsequent rounds of amplification. Repeat cycles of bridge amplification produce a plurality of amplified nucleic acid molecules that are attached to the support. The cycles of bridge amplification can be conducted under isothermal conditions. Examples of compositions and methods for bridge amplification are found in U.S. Pat. Nos. 7,790,418, 7,985,565, 8,143,008 and 8,895,249.

Yet another amplification method for generating monoclonal nucleic acid populations is known as "template walking". As in bridge amplification, individual template molecules may be equipped with 5' and 3' primer binding sequences ("first and second adaptors") capable of hybridizing to complementary sequences of first and second primers. However, in contrast to bridge amplification where both (forward and reverse) capture primers are immobilized on a solid support, template walking amplification is typically performed with only the forward primer immobilized on the support ("capture primer"), whereas a reverse primer may be provided in solution ("soluble primer") e.g. as component of the reaction mixture comprising amplification reagents such as polymerase, dNTPs and buffer, etc. Template walking requires hybridization of a single-stranded nucleic acid template to one of a plurality of capture primers immobilized on the support (e.g., a bead), wherein at least the 3' ends of all capture primers include a sequence that is compatible with the first adaptor sequence in the nucleic acid template. In some embodiments, the capture primers or at least the 3' ends thereof include a sequence having a low $T_m$ (melting temperature) also referred to as "breathable" region. The breathable region is for example a sequence that is rich in A, T and/or U, such as an AT (or U)-rich sequence, such as polyT, polyA, polyU and any combinations of A, T and U bases, or bases complementary to such bases. In the hybridization step, the first adaptor sequence hybridizes with a first immobilized capture primer, and a primer extension reaction extends the first capture primer along the hybridized template to generate a first capture primer extension product having a complementary sequence of the second adaptor at one end. The template molecule (which is hybridized along its length to the extension product) undergoes partial denaturation at the first adaptor region that contains the low $T_m$ region, and the first adaptor region re-hybridizes to another nearby second capture primer, while the remainder of the template remains hybridized to the extension product. Primer extension of the second capture primer serves to denature the portion of the template molecule that is still hybridized with the first extension product, and generates a second capture primer extension product. Repeat cycles of template walking include hybridizing the first adaptor region to a nearby capture primer, primer extension, partial denaturation, re-hybridization with a different nearby capture primer, and primer extension, producing a plurality of amplified target nucleic acids that are attached to the support. Likewise, the capture primer extension products (reverse strands) can be amplified using soluble reverse primers, wherein at least the 3' ends of all soluble primers include a sequence that is complementary to the second adaptor in the reverse strands. In some embodiments, the soluble primers or at least the 3' ends thereof include a breathable sequence region having a low $T_m$ (melting temperature). The cycles of template walking can be conducted under isothermal conditions, where temperature variation is constrained within a limited range during at least some portion of the amplification (e.g., the temperature variation is within 20° C., optionally within 10° C., for example within 5° C., or 2° C.). Examples of compositions and methods for nucleic acid template walking are found in U.S. Patent Public. Nos. 2012/0156728, 2013/0203607 and in WO 2013/158313. Partial strand separation in template walking may be achieved by using low melt primers and/or adaptor sequences or alternatively, by using recombinase-polymerase amplification (RPA) under isothermal conditions. Examples of compositions and methods for RPA reactions are found in U.S. Patent Publication Nos. 2013/0225421 and 2014/0080717, and in U.S. Pat. Nos. 7,399,590, 7,666,598, 8,637,253, 8,809,021, and 9,057,097. In some embodiments, the reaction mixture for isothermal amplification may include a polymerase (e.g., Bst DNA polymerase) and/or a recombinase (e.g., T4 uvsX), and optionally accessory pro-adjusted. For example 10 million capture primer-bound beads may be combined with 100 μl template at 0.01 pg/μl.

In the lower portion of Part 1 (B), nucleic acid molecules are designed and synthesized to encode either different proteins or variants of one or more proteins. As an example, the nucleic acid molecules may encode native and altered forms of interleukin 2 (IL-2). For purposes of illustration, an amino acid sequence of human IL-2 is set out in Table 3.

TABLE 3

| |
|---|
| 1 MAPTSSSTKK TQLQLEHLLL DLQMILNGIN NYKNPKLTRM LTFKFYMPKK |
| 51 ATELKHLQCL EEELKPLEEV LNLAQSKNFH LRPRDLISNI NVIVLELKGS |
| 101 ETTFMCEYAD ETATIVEFLN RWITFCQSII STLT (SEQ ID NO: 5) | teins, including recombinase loading factor (e.g., T4 uvsY) and/or single-stranded binding protein (T4 gp32).

As a substantial proportion of templates and extended reverse strands remain hybridized at all times during or between amplification cycles, the templates or amplification products will not denature completely and diffuse away to hybridize to capture primers on a different reaction site or bead thereby limiting cross-contamination. It is therefore important that both strands are only partially separated to an extent sufficient to allow the breathable template portion to walk over to another adjacent capture primer.

Template walking allows for simultaneous amplification of a plurality of different nucleic acid molecules within the same continuous liquid phase without prior compartmentalization. Where amplification is conducted on beads, each bead may receive a different member of a library separately amplified to generate multiple clonal populations of amplicons that remain immobilized on the beads for further downstream processing (such as IVTT, sequencing, cloning etc.). To further slowdown the rate of diffusion of individual nucleic acid molecules within the continuous liquid phase, the reaction mixture may contain one or more diffusion limiting agents, crowding or sieving agents or nucleic acids may be attached to a "drag compound" to reduce the mobility of such nucleic acids in the reaction mixture. Such strategies may be useful in further reducing cross-contamination of templates or amplification products between different amplification sites (e.g. different beads) within the same liquid phase and are further described, e.g., in PCT Publication WO 2013/158313.

Alternatively, a nucleic acid library can be amplified using a method that exploits kinetic exclusion, wherein the average amplification rate of a nucleic acid molecule at a given amplification site exceeds the average rate at which the nucleic acid molecule is transported to said amplification site. The transport rate may be controlled, e.g., by decreasing the concentration of templates or increasing the viscosity of the reaction mixture as described in U.S. Patent Publication No. 2013/0338042.

To facilitate mono-clone formation around a centered initiation site (as in bridge amplification or template walking), the nucleic acid library or mixture of template molecules may need to be diluted to ensure that each amplification site or each bead will only receive a single nucleic acid molecule (similar to the BEAMing method discussed above). For this purpose, the ratio of the number of nucleic acid molecules to the surface area of a support comprising multiple amplification sites or the ratio of the number of nucleic acid molecules to the number of beads may be A number of mutated forms of IL-2 are known and have been shown to have various properties (e.g., increased solubility, decreased toxicity, etc.). The following amino acid alterations are known in the art: L18M, L19S, R38W, N88R, V91R, C125A, and Q126T. All but one of these mutations is located in regions of IL-2 predicted to form α-helices (depending on the modeling algorithm employed). Thus, one may seek to focus amino acid sequence alterations at other locations in IL-2 but in α-helical regions (underlined in Table 3).

Further, there may be a desired to generate and test combinatorial combinations of known and new amino acid sequence alterations. A number of nucleic acid molecules (e.g., from about 50 to about 250) encoding different forms of IL-2 altered at one or more amino acid location, and/or with different amino acids at the various locations, may be generated and tested for one or more biological activity. Of course, testing of a protein or altered form of a protein for biological activity typically requires that the protein be produced and present isolated from proteins or protein forms that would interfere with biological activity measurements.

Part 2

In some instances, Part 2 of the workflow set out in FIG. 23 may be a component of Part 1. One example would be if a multiwell plate was used to synthesize DNA on a bead and the same plate was used for in situ IVTT.

Typically, it will be desirable to spatially separate nucleic acid molecules encoding different encoded proteins prior to performing IVTT. For example, as shown in FIG. 26, library members may be amplified on beads in solution within the same liquid phase (e.g., in a single reaction vessel) and (optionally enriched) beads containing multiple copies of individual library members may subsequently be distributed into wells of a multiwell plate or a microfluidic chip such that each well will optimally obtain a single bead as illustrated by FIG. 26.

Figure 24:
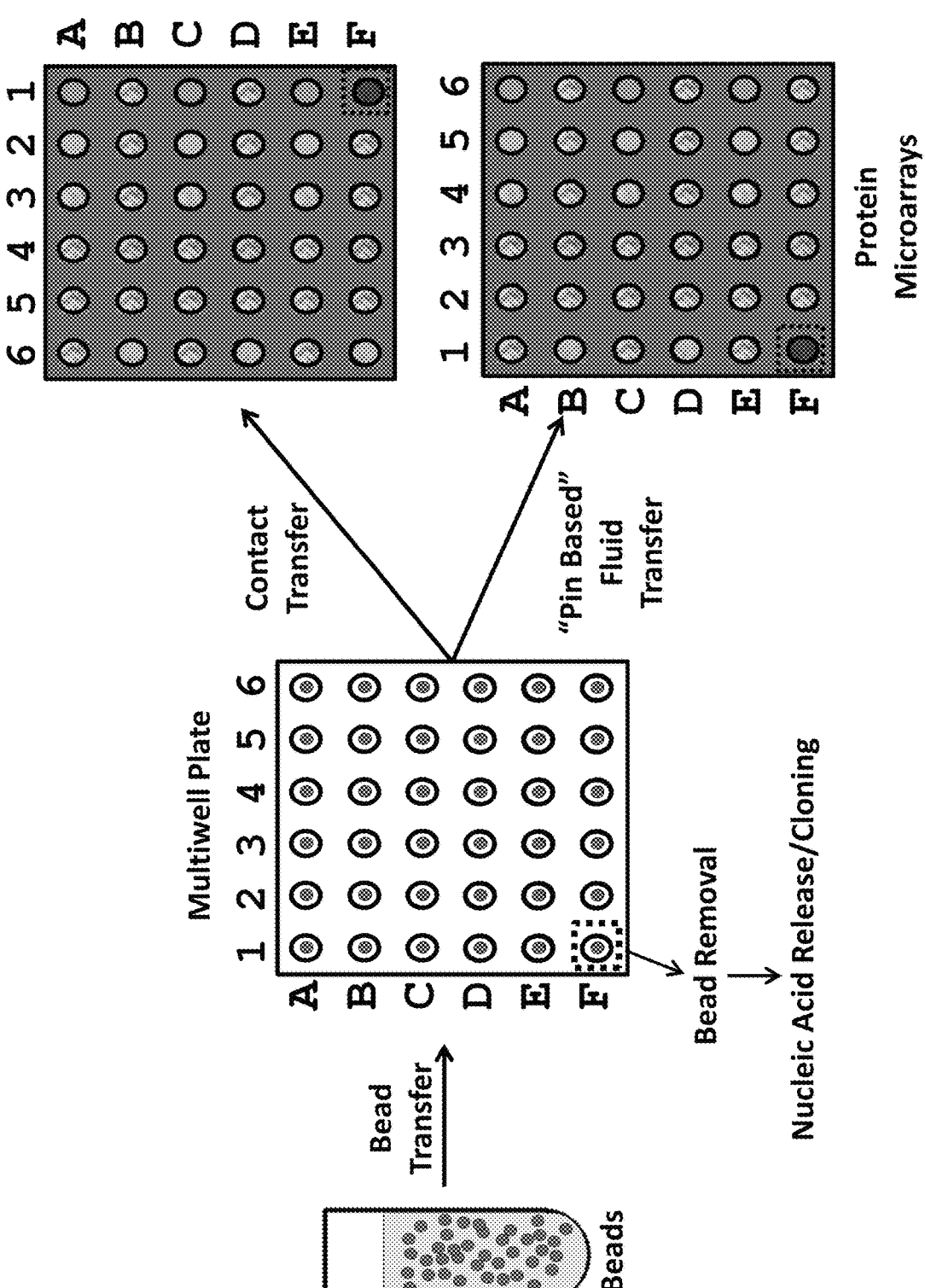
FIG. 24 shows an exemplary embodiment of the invention. In this embodiment, beads, each designed to have attached thereto nucleic acid molecules encoding the same protein or protein variant, are loaded into wells of a microwell plate. IVTT reactions then are performed in each well, after which fluid containing the protein produced is transferred to a matrix to form a microarray, or the protein that is expressed is bound to a capturing surface, which can be the bead itself, the surface of the well, or the lid of the well. The protein microarray may be printed by direct contact of the fluid to the lid, which has been modified to capture proteins, e.g., Ni-NTA (upper right, e.g., by overlaying the matrix onto the microwell plate) or by (lower right, e.g., micropi-petting the fluid onto the matrix).
Figure 26:
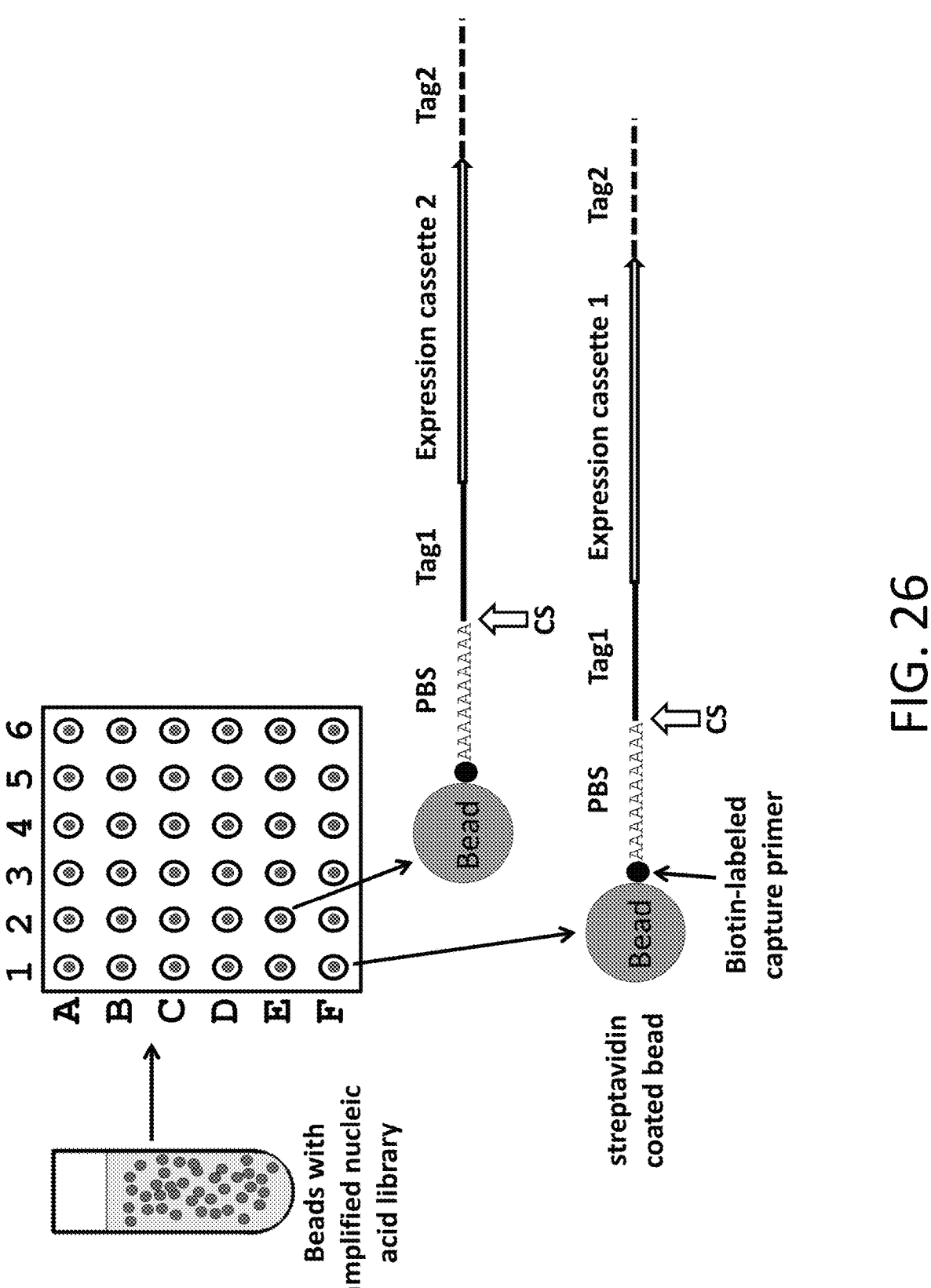
FIG. 26 shows an embodiment of the invention where a mixture of nucleic acid molecules encoding different pro-teins is amplified on beads in solution prior to distribution of the amplicon coated beads into wells of a microwell plate. Following clonal amplification each bead carries multiple copies of an individual library member (for simplification, only one nucleic acid molecule per bead is indicated). Amplicons may optionally be rendered single-stranded (e.g., by heat denaturation) prior to distribution into the wells. Each library member attached to a bead may comprise at least one terminal primer binding site (PBS) (SEQ ID NO: 20) for amplification, one or more tags for sequencing (comprising a sequencing adaptor and, optionally, a univer-sal and/or unique barcode), optionally a restriction enzyme cleavage site (CS) for downstream processing of selected nucleic acids, and an expression cassette comprising a 5'-UTR sequence containing a promoter, a protein encoding sequence variant, and a 3'-UTR sequence (see FIG. 12 for an exemplary expression cassette).

While FIGS. 24 and 26 show bead based methods, nucleic acid molecules may also be generated or spotted on other types of surfaces, for example, the bottom of wells of a microwell plate. Thus, the nucleic acid molecules may be attached to any type of surface so long as the surface allows for the performance of various methods set out herein.

When beads are placed into well, the nucleic acid attached these beads may be a random assortment of nucleic acid molecules to be screened for desired expression products. Using FIG. 24 for purposes of illustration, beads with nucleic acid molecules bound thereto are used to fill wells of a multiwell plate. In many instances, the beads will be placed randomly into wells, resulting in essentially a random assortment of nucleic acid molecules within the plurality wells.

Part 3

The next step in the workflow set out in FIG. 23 is in vitro transcription and translation (IVTT). This is performed so that encoded proteins are generated. This allows for screening of the proteins for desired activities.

IVTT methods are set out in detail elsewhere herein. The invention will generally include the use of IVTT methods that involve efficient generation of proteins.

In aspects of the invention set out in embodiments of the invention represented in FIGS. 23, 24, and 26, as well as related embodiments, proteins encoded by spatially separated nucleic acid molecules are generated in discrete locations. One example of a discrete location is a well of a microwell plate.

Using the schematic of FIG. 24 for purposes of illustration, a microwell plate is shown having 36 wells, designated by columns (numbered) and rows (lettered). Beads are placed in each of the 36 wells. Also, present in wells is an IVTT reaction mixture, which may be supplied to the wells after the beads were placed in the wells. The microwell plate is incubated under conditions that all for IVTT reactions to occur, resulting in the generation of proteins encoded by the nucleic acid molecules present within each well.

Part 4

Once proteins have been produced, one or more proteins of interest may be identified. In many instances, proteins will be transferred out of wells for analysis and/or testing. This is advantageous because it allows for the separation of screening processes from the nucleic acid molecules. In some instances, screening processes may adversely affect nucleic acid molecules. Protein transfer and testing may be done in number of ways.

Transfer may be done, for example, by contact of fluid in wells with a surface upon which testing will be performed or by removal of fluid which is then delivered to another location. FIG. 24 shows examples of both methods of fluid transfer. The lower left of FIG. 24 shows what is referred to as "pin based" fluid transfer. This transfer may be mediated, for example, by pins that dip into the fluid in the wells, followed by spotting of the fluid onto a planar material or surface.

Figure 25:
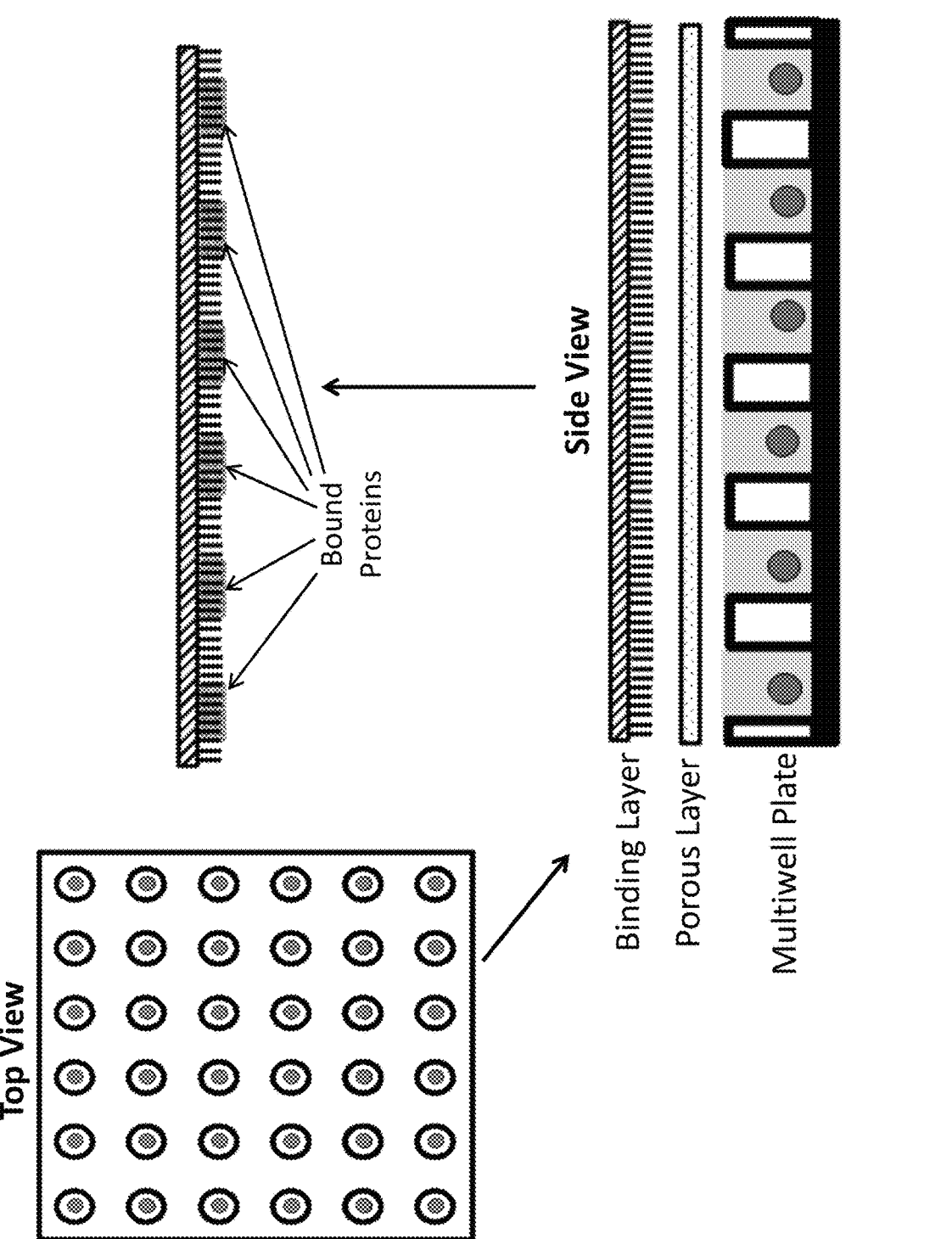
FIG. 25 shows a top view and a side view of a multiwell plate containing beads in wells, as well as a side view of a material that will bind to tags associated with expressed proteins ("Binding Layer"). The beads in the wells have attached thereto nucleic acid molecules which encode pro-teins. The wells also contain IVTT reaction mixtures. The individual beads are designed to have attached thereto nucleic acid molecules that encode the same proteins. Thus, one protein is produced per well. The multiwell plate is shown as being overlayed with the Porous Layer and the Binding Layer. Fluid, with proteins contained therein, passes through the Porous Layer and enters into contact with the Binding Layer, where the proteins become bound to the Binding Layer. The lines protruding from the bottom surface of the Binding Layer represent functional groups that will connect the proteins to the surface.

In FIG. 25 a multiwell plate is overlayed with a planar material, such as a sheet of glass. Proteins are transferred to multiple locations of the planar material via indirect contact. After transfer, the planar material contains a mirror image representation of proteins located within wells of the multiwell plate.

More specifically, FIG. 25 shows the overlaying of a multiwell plate with an optional Porous Layer that absorbs fluid from the wells. The Porous Layer assists with even contact of the planar material across the top of the wells. As shown in FIG. 25, proteins in the fluid pass through the porous layer and then contact the Binding Layer. The Binding Layer can be composed of any number of materials and may be flexible (e.g., a membrane) or rigid (e.g., plastic or glass). Proteins that bind to the Binding Layer will often have a tag that that interacts with the surface of the Binding Layer. One exemplary tag that can be used is a histidine tag. When this tag is used, the Binding Layer will often be derivatized with nickel-nitrilotriacetic acid (Ni-NTA). Further, the multiwell plate may be composed on any number of materials such as polydimethylsiloxane.

A number of publications set out materials and procedures that may be used in various aspects of the invention.

Examples of such publications include Tanaka et al., "HIGH-THROUGHPUT PROTEIN MICROARRAYS: FEATURE SIZE EFFECTS ON PRINTING ARRAYS WITH IN SITU PROTEIN SYNTHESIS", 16*th International Conference on Miniaturized Systems for Chemistry and Life Sciences, Oct.* 28-Nov. 1, 2012, Okinawa, Japan, pages 1297 to 1299; Kilb et al., "*Protein microarray generation by in situ protein expression from template DNA*", (DOI: 10.1002/elsc.201300052) (2014).

In some instances, magnetic beads may be used and a regulatable magnetic field may be used to hold beads in position. In such instances, the multiwell plates may contain a material that can generate magnetic fields addressable on a per well basis. When beads in certain wells are to be released, for example, into a flow stream, the magnetic field can be interrupted in those wells, resulting in decreased affinity for the beads to the well surfaces. One example of such a multiwell plate is set out in Sato et al., "ARTIFICIAL DARWINIAN SELECTION TECHNOLOGY ON MICROARRAY CHIPS TOWARDS DIRECTED EVOLUTION USING SINGLE MOLECULE PROCESSING", 16th International Conference on Miniaturized Systems for Chemistry and Life Sciences, Oct. 28-Nov. 1, 2012, Okinawa, Japan, pages 124 to 126.

One method for making slides derivatized with Ni-NTA is as follows. 0.6 g of NTA, and 1 g of NaHCO$_3$, is dissolved in 5 ml of water. 50 to 100 µL of this solution is placed on the surface of an epoxy-functionalized slide (Arrayit Corp., Sunnyvale, CA) and left overnight. The slides are then washed with water and allowed to dry. The dried slides are then placed in a glass jar with about 600 ml of 1% NiSO$_4$, react for three hours. Afterwards the slides are placed in a solution containing 0.2 M acetic acid, 0.2 M NaCl and 0.1% Tween-20 for 10 minutes, washed with water, dried with nitrogen, and left in fume hood for completion of the drying process.

Additional ways to attach proteins to the binding layer are by the use of the following protein tags: Tus (with Ter on the binding layer) and FLAG (with an anti-FLAG antibody on the binding layer). Numerous other tag/binding partner combinations are known in the art (see, e.g., Kilb et al., "*Protein microarray generation by in situ protein expression from template DNA*", (DOI: 10.1002/elsc.201300052) (2014)). Exemplary tags are set out in Table 4.

TABLE 4

| Exemplary tags and cognate surface localized binding group | |
|---|---|
| Protein Tag | Cognate Surface Group |
| DoubleHis, HexaHis (SEQ ID NO: 3), DecaHis (SEQ ID NO: 6), etc. | Ni-NTA |
| Flag | Flag Antibody |
| c-myc | c-myc Antibody, |
| Hemagglutanin | HA Antibody |
| GFP | GFP Antibody |
| GST | GST Antibody |
| Maltose-binding protein | Maltose |
| lacZ | Lac DNA sequence |
| Calmodulin-binding protein | Calmodulin |
| Protein A | Protein A Antibody |
| Protein G | Protein G Antibody |
| Strepavidin | Biotin |

Once proteins are positioned in a place where they can be tested (e.g., attached to a matrix, such as a binding layer, or localized in, for example, a well), any number of methods may be used to identify one or more proteins of interest. Once such identification method is based upon the ability of an antibody to bind to the proteins of interest. Such methods are especially useful when the proteins are produced from members of a diverse library (e.g., a cDNA library).

Using the schematic shown in FIG. 24 for purposes of illustration, protein microarrays may then be contacted, for example, with a primary mouse antibody that binds the proteins of interest. The protein microarrays may then be contacted, for example, with a labeled secondary goat, anti-mouse antibody. Protein of interest detection is seen in spot corresponding to well 1F (surrounded by a dashed square).

Other detections methods may also be used. For example, one or more biological property other than or in addition to antibody binding may be used. Such biological properties include enzymatic properties (e.g., protease, polymerase, luciferase, etc.) solubility, toxicity, and receptor stimulation.

Using altered forms of IL-2 as another example for illustration, fluid may be transferred to wells of a multiwell plate, where one or more cellular responses are measured.

IL-2 is known to be a potent T cell growth factor and has been used clinically to enhance T cell immunity in patients with AIDS or cancer. Further, IL-2 is typically necessary for the expansion of CD4+ CD25+ regulatory T cells (Treg cells). Thus, one assay of biological activity is the ability to induce expansion of Treg cells.

Altered forms of IL-2 may be produced in wells of a first multiwell plate, this protein may be transferred to wells of a second multiwell plate that contains Treg cells, a culture medium, and all other components required for expansion except IL-2. IL-2 may then be added to Treg cell expansion may then be measured and compared against a control well of an equivalent amount (e.g., 100 ng/ml) of wild-type IL-2. Finally, rate of expansion (e.g., fold expansion after 48 hours) and total expansion (e.g., fold expansion after 10 days) may be measured. Increase rate of expansion and/or total expansion indicates an increase in Treg cell expansion induction activity, while decreases in either one or both of these parameters indicate a decrease in Treg cell expansion induction activity.

Altered forms of IL-2 that demonstrate little or no Treg cell expansion activity may then be tested for their ability to bind interleukin-2 receptors (IL-2R). Altered forms of IL-2 that bind to IL-2Rs but do not stimulate receptor activity may be used to block IL-2 responses.

Part 5

Once a protein of interest has been identified, one will often desire to obtain the nucleic acid molecule which encodes it. This is the case for several reasons. First, the nucleic acid molecule may be sequenced in order to determine the amino acid sequence of the protein of interest. Second, the nucleic acid molecule may be used to produce more of the encoded protein.

FIG. 24 shows a system where the protein of interest may be traced back to the well from which it came. This leads to identification of the nucleic acid molecule that encode the protein. Once a well containing a nucleic acid molecule encoding a protein of interest has been identified, the nucleic acid molecule may be removed from the well. When the nucleic acid molecule is attached to a bead (as shown in FIG. 24), the bead may be removed from the well and transferred to a location where the nucleic acid is released. Alternatively, the nucleic acid molecule may be released from the bead in the well, followed by transfer of the released nucleic acid molecule from the well. Similarly, if the nucleic acid molecule is attached to a surface of the well, the nucleic acid molecule may be released from the surface, followed by transfer of the nucleic acid molecule from the well.

When the nucleic acid molecule is attached to a bead, the bead may be removed by a number of different methods. For example, for large plates (e.g., standard 96 well plates) with easy access to the well, the bead may be removed by use of a mechanical device, such as a pair of tweezers or suction tip.

One method for selectively removing beads, especially small beads, is through the generation of a gas bubble below the beads to lift them out of the wells in which they are located. The beads may then, for example, be transported to one or more locations in "flow streams" passing over the surface of the wells. As an example, assume that a plate 1000 beads, where each bead in wells contains nucleic acid molecules encoding a library of altered cytokine (e.g., IL-2) and ten of the beads have been identified as containing nucleic acid molecules encoding protein variants of interest. Further assume that all ten beads are removed from the plate and collected as a mixture. Nucleic acid molecules may be released from the beads as a group, then introduced into expression vectors using standard techniques, cloned, and expression products of the individual clones may then be screened for biological activity. One advantage of such a process is that it allows for "high-throughput" narrowing of candidate proteins of interests. Further, more than one protein of interest may have one or more desirable properties. For example, assume that that three of the ten variant proteins of interest have the highest (or lowest) biological screened activity. These three proteins of interest may then be tested for additional desirable properties (e.g., serum half-life, stability at various pHs, etc.).

Figure 27:
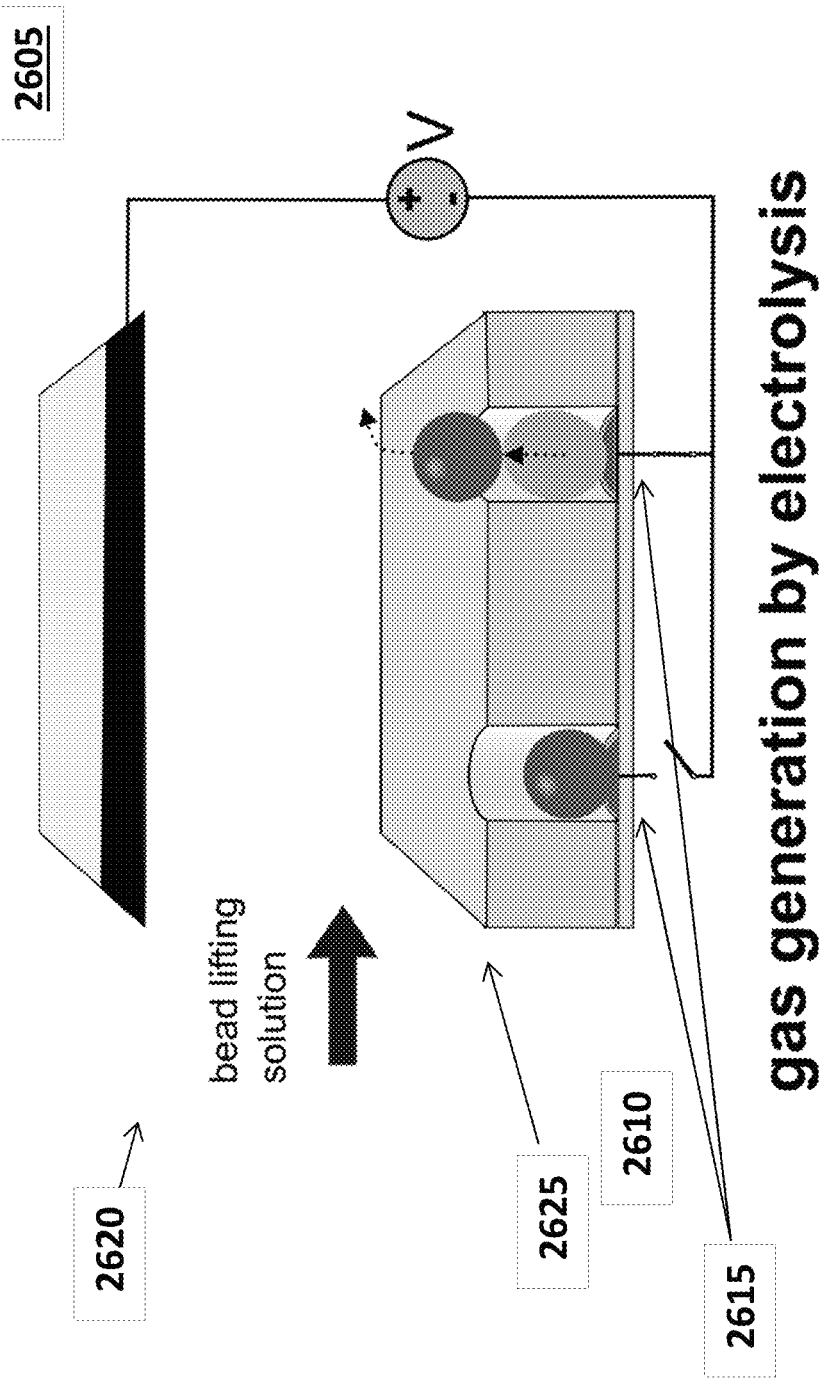
FIG. 27 shows an example of a selective bead removal process from a multiwell plate using electrolysis according to methods of the invention.

FIG. 27 shows a simplified example of a selective bead removal process from a multiwell plate 2605 using electrical current to generate one or more gas bubbles below the bead. In this embodiment, wells of the multiwell plate contain a first electrode 2615 (working electrode) formed at a bottom surface of the microwell and a second electrode 2620 (counter electrode). If the fluid in the well is water, then about a 0.01V to about 10,000V, a 5V to about a 30V, or about 10V to about a 20V, or about a 15V to about a 30V, voltage can be applied to produce the electrochemical reaction. As the one or more gas bubbles expand and move toward the surface of the microwell 2610, the bead 2625 will also tend to rise. As a result, the volume of the fluid in the microwell 2610 is displaced and the bead 2625 is released from the microwell 2610 into a fluidic channel (not shown), for example in the direction indicated by the arrow in FIG. 27. The generation of the air bubbles generally occurs quickly, usually taking less than a second (although longer times may be used) for the bead to be displaced due to the rising of one or more gas bubbles, and is not dependent on the surface charge or other properties of the bead.

As noted herein, the generation of gas bubbles in microwell plates can be used as a method to remove beads from the respective well. Gas bubbles can be produced electrochemically in aqueous or non-aqueous buffers (e.g., water, NaCl dissolved in water and more complex non-aqueous solutions such as 0.7 M tetraethylammonium p-toluenesulfonate, 50% water, 30% methanol, 20% acetonitrile. The inherent properties of the buffer used can have significant implications on the efficiency or performance of the system. For example, the composition of the buffer can influence the surface tension of the bubbles produced. The surface tension is critical for the bubble movement in the well (retention potential). For an efficient removal of beads from a well it is desirable that both, beads and bubbles escape from the well (compared to the bubbles remaining in the well and disturbing the fluidic flow of the system). If the surface tension is too low, the generated bubbles will escape through the gap between well and bead without lifting the bead. If, however, the surface tension is too high, gas bubbles will stick tightly to the walls of the well, which may require additional treatment to remove the gas bubbles such as longer rinsing or rinsing with low surface tension solvents (such as e.g. methanol). Further, high surface tension may also result in beads sticking to gas bubble and not being released into the fluid stream. A favorable surface tension can be achieved by mixing organic solvents (e.g., acetonitrile, isopropanol) and aqueous solutions, preferable 50-90% organic solvents, more preferably, 60-70% organic solvent. The buffer can also be selected to avoid negative effects on the synthesis process. For example, acidic environment has the potential to damage the nascent oligonucleotide chain, and basic condition can promote premature cleavage of the oligonucleotide from the bead. Therefore, a buffered system can be used to avoid the generation of such an undesired condition. Although different buffer systems are available (e.g., HEPES, TRIS, carbonate or ammonium based buffers) a volatile buffer (e.g., ammonium sulfate) is preferred for the application in order to avoid undesired residues which might negatively influence other reaction steps.

In certain instances a lifting buffer may comprise water, tetraethylammonium-p-toluolsulfonate (NEt4pTsO), acetonitrile and methanol. In an exemplary embodiment a lifting buffer comprising 0.7 M (NEt4pTsO), 50% water, 30% methanol, and 20% acetonitrile can be used. This buffer has a high conductivity required for electrochemical generation of gas bubbles while its surface tension allows for efficient bead lifting and removal of bubbles from wells. Using this buffer, bead lifting can be achieved at a potential of >4.5 V. In certain embodiments a higher potential may be used for optimal bead lifting. For example, 8.5 V may be used without limiting the current. In a typical experiment a current of 20-60 mA may be observed for approximately 3,500 wells.

In certain embodiments, the displacement of one or more beads from the multiwell plate is controlled and programmed by computer directed automation. For example, when the multiwell plate 2605 may be formed as a CMOS chip, each working electrode formed at the bottom of the microwells can be individually addressable, which allows the controller to selectively energize one or more working electrodes at a given time. Thus, one or more beads can be displaced from their respective microwells at the same time or about the same time to be subsequently collected for further processing and analysis.

Compositions and methods for gas bubble generation of removal of solid supports from wells of multiwell plate are set out in U.S. patent application Ser. No. 14/964,060, filed Dec. 9, 2015, entitled "HIGH EFFICIENCY, SMALL VOLUME NUCLEIC ACID SYNTHESIS".

EXAMPLES

Example 1: Exemplary Methods for Nucleic Acid Synthesis and Assembly

The desired protein sequences were uploaded in the GENEART® internet portal, which employs a computer program configured to analyze and process the sequence based on an algorithm as described in U.S. Patent Publication No. 2007-0141557 A1. Using the software, the protein sequence is "retro transcribed" in a DNA coding sequence or open reading frame (ORF), which is then optimized for expression in yeast (*Saccharomyces cerevisiae*). Nucleic acid molecules such as those used in these examples may be obtained from Thermo Fisher Scientific, Inc. the parent company of GeneArt. Nucleotide sequences that were generated by this program are set out in FIGS. 16-19.

Depending on the length the optimized ORF can be broke up into subfragments (fragments larger than 1 kb) or directly into oligonucleotides (fragments up to 1 kb) using the GeneOptimizer software. Sense and antisense strand of each fragment/subfragment are broke up into partially overlapping oligonucleotides ranging between 50 and 60 bases in length.

Oligonucleotides covering the 5'-3' strand are referred to as L-oligos; reverse oligos covering the complementary strand are referred to as m-oligos. The overlapping regions between forward (L-) and reverse (m-) oligonucleotides have similar melting temperatures. Length of the overlapping regions and gaps between adjacent oligos vary based on the melting temperatures (see, e.g., FIG. 8).

L- and m-oligonucleotides are synthesized by solid-phase synthesis using phosphoramidite building blocks and are mixed in stoichiometric amount. Each oligonucleotide is 0.15 μM in the final oligonucleotide mix.

Gene assembly is done using a PCR based method. During the PCR complementary DNA sequences are hybridized. (Only DNA hybrids containing a 5' protruding end can be elongated starting from free 3'hydroxyl group (OH—).)

Strings up to 1 kb are assembled from a single oligonucleotide set. Strings larger than 1 kb are divided into subfragments (up to three subfragments) and are assembled together in a fusion PCR reaction.

"Strings" are linear expression cassettes consisting of a variable open reading frame (ORF), ordered by the customer, and two constant 5'- and 3'-UTR regions featuring all elements needed for the IVTT reaction and the C-terminal his tag for protein purification. UTRs and ORF are assembled by fusion PCR based on about 30 base pair overlapping regions.

ORFs up to about 1 kb are synthesized from one single oligonucleotide set. ORFs longer than 1 kb are divided into subfragments (up to three subfragments). For each subfragment one single oligonucleotide set is designed. Each subfragment features an about 30 base pair overlapping region to the adjacent one and the first and last subfragments feature an about 30 base pair overlapping region to the 5'- and 3'-UTR, respectively. All subfragments and the two UTRs are assembled by fusion PCR (FIG. 1).

String Construction
Oligonucleotides Assembly: OE-PCR

OE-PCR and SPCR master mix (MM) is prepared by mixing the following: 5 μl 10× True Script buffer (PAN biotech), 1 μl dNTPs (10 mM each), 10 TRUESCRIPT™ DNA Polymerase (PAN biotech), and H2O (20 μl)

OE-PCR reaction: 27 μl master mix (MM), 10 μl oligonucleotide mix (0.15 μM L/m oligonucleotide mix), 27 μl OE-PCR/SPCR-MM and 13 μl H2O are mixed to form a 50 μl reaction mixture. The final concentration of components are as follows: 0.03 μM each oligonucleotide, 0.2 mM dNTPs, 1× True Script buffer, 2.5 U TRUESCRIPT™ DNA Polymerase.

PCR conditions are indicated below.

A touch down PCR is performed: annealing temperature is reduced by 0.8° C. each cycle.

OE-PCR Thermal Cycling Program:

TABLE 5

| OE-PCR thermal cycling program | | |
|---|---|---|
| 95° C. | 4 min | |
| 95° C. | 30 sec | |
| 60° C.* | 30 sec | 30× |
| 72° C. | 1 min | |
| 72° C. | 4 min | |
| 4° C. | ∞ | |

*touch down −0.8° C./Cycle

SPCR reaction: 7 µl OE-PCR product, 10 µl forward and reverse primer-mix (each 5 µM) (pf and pb), 11 µl H2O, 27 µl OE-PCR/SPCR-MM) are mixed to form a 55 µl reaction mixture. The final concentration of components are as follows: 0.9 µM each primer, 0.2 mM dNTPs, 1× True Script buffer.

PCR conditions are indicated below.

SPCR Thermal Cycling Program

TABLE 6

| SPCR thermal cycling program | | |
|---|---|---|
| 95° C. | 30 sec | |
| 95° C. | 30 sec | |
| 58° C. | 30 sec | 30× |
| 72° C. | 1 min | |
| 72° C. | 4 min | |
| 4° C. | ∞ | |

Error Correction:

For strings up to 1 kb, 2 µl SPCR are mixed with 3.33 µl 10× Ampligase buffer and 14.67 µl $H_2O$. For strings larger than 1 kb, 30 SPCR of each subfragment are mixed with 3 µl SPCR 3.33 µl Ampligase buffer 10× and $H_2O$ is added to 20 µl final volume.

6 µl of this mix undergoes denaturation-rehybridization to allow formation of mismatches.

TABLE 7

| Denaturation-rehybridization program | |
|---|---|
| 98° C. | 2 min |
| 4° C. | 5 min |
| 37° C. | 5 min |
| 4° C. | ∞ |

6 µl of the denaturated-rehybridized DNA is mixed with 1 µl Taq Ligase (NEB), 1 µl T7 Endonuclease (NEB), Ampligase buffer 1× and $H_2O$ is added to 10 µl final volume. The error correction takes place at 45° C. for 20 minutes.

Fusion PCR

Error corrected ORFs or ORF subfragments are combined with the 5'- and 3'-UTR to build a functional expression cassette (strings) by fusion PCR.

2 µl error correction mix, containing up to 3 ORFs subfragments, are combined with 0.1 pmoles of each UTR, 1× Phusion HF Buffer (THERmo FISHER SCIENTIFIC®) and 0.8 U Phusion DNA Polymerase (THERMO FISHER SCIENTIFIC®) 0.2 mM dNTPs and 32.1 µl $H_2O$. PCR conditions are summarized below. After 15 cycles 2.5 µl of 10 µM forward primer (pf) and 2.5 µl of 10 µM reverse primer (pb) and PCR proceeds as indicated in Table 8.

TABLE 8

| 2 µl | Error correction reaction |
|---|---|
| 1 µl | 5'UTR (0.1 pmoles) |
| 1 µl | 3' UTR (0.1 pmoles) |
| 10 µl | 5 × Phusion HF Buffer (THERMO FISHER SCIENTIFIC ®) |
| 1 µl | dNTPs (10 mM each) |
| 0.40 µl | Phusion DNA Polymerase 2 U/µl (THERMO FISHER SCIENTIFIC ®) |
| 32.10 | $H_2O$ |
| 50 µl | |

TABLE 9

| Fusion PCR program | | | |
|---|---|---|---|
| 98° C. | 2 | min | |
| 98° C. | 20 | sec | |
| 65° C.* | 30 | sec | 15× |
| 72° C. | 90 | sec | |
| 25° C. | Pause** | | |
| 98° C. | 20 | sec | |
| 65° C. | 30 | sec | 20× |
| 72° C. | 90 | sec | |
| 4° C. | ∞ | | |

*touch down −0.5° C./Cycle
**added 2.5 µl of 10 µM pb primer and 2.5 µl of 10 µM pf primer

Example 2: Magnetic Beads Based String Purification

Strings are purified using the THERMO FISHER SCIENTIFIC® MAGJET™ NGS Cleanup and Size Selection Kit (THERMO FISHER SCIENTIFIC®) before they are used as template in the IVTT reaction.

5 µl MAGJET™ magnetic beads are mixed with 700 µl Binding Mix in a microcentrifuge tube. Fusion PCR is added and the DNA-beads mix is vortexed until a homogenous suspension is obtained. After 5 minutes incubation at room temperature the tube is briefly centrifuged to collect droplets. The tube is then placed tube in the magnetic rack for 2-3 minutes or until the beads have formed a tight pellet. Keeping the reaction vessel on the magnet, the supernatant is carefully discarded by using a pipette. 400 µl of Wash Solution (supplemented with ethanol) are added and the tube is placed it back in the magnetic rack for 1 to 2 minutes. The supernatant is carefully removed by using a pipette. The washing step is repeated. The sample is centrifuged and placed back in the magnetic rack for 1 minute before elimination the residual wash solution. Keeping the tube on the magnet, the magnetic particles are air dried at room temperature for 5 minutes.

Strings are finally eluted by adding 15-30 µl Elution Buffer. After vortexing and brief centrifugation, the sample is incubated for 1 minute at room temperature, placed back in the magnetic rack for 3 minutes. The supernatant containing the purified DNA is collected and used as template in the IVTT reaction.

Example 3

String DNAs were synthesized as set out above in Examples 1 and 2 encoding a C-terminal His tag in addition to the protein to be translated. As set out below, IVTT reactions were set up to express the human and yeast optimized strings in HeLa based coupled/High-Yield IVTT reactions.

A number of components used in the process below are included in THERMO FISHER SCIENTIFIC®'s product "1-Step Human High-Yield Mini IVT Kit" (Cat. Nos. 88890 and 88891).

5× Dialysis Buffer and Nuclease-Free Water were combined in a 2.0 ml microcentrifuge tube as set out in Table 10. A tubular dialysis device (from THERMO FISHER SCIENTIFIC®, Cat. No. 88890Y) was placed inside the 2.0 ml tube microcentrifuge tube containing 1× Dialysis Buffer and incubated while the rest of the IVT reaction components are assembled together as shown below.

TABLE 10

| Dialysis Buffer Preparation | |
| --- | --- |
| Component | Vol (µl) |
| 5× Dialysis Buffer | 280 |
| Nuclease-Free Water | 1120 |
| Total | 1400 |

After dialysis, IVTT reaction mixtures were prepared as set out in Table 11, with reagents added in the order listed into a 1.5 ml RNase/DNase-free tube. HeLa Lysates were with mixed with Accessory Proteins and incubate for 5-10 minutes at room temperature prior to the remaining components being added. The reaction was gently mixed after each reagent addition. After all for the components in Table 11 were mixed, the mixture was centrifuged at 10,000×g for 2 minutes.

TABLE 11

| | IVTT reaction Components | |
| --- | --- | --- |
| Component | GFP Control (µl) | Target Protein (µl) |
| HeLa Lysate | 50 | 50 |
| Accessory Proteins | 10 | 10 |
| Reaction Mix | 20 | 20 |
| pCFE-GFP DNA (0.5 µg/µL) | 8 | — |
| Sample DNA (0.5 µg/µL) | — | 8 |
| Nuclease-Free Water | 12 | 12 |
| Total | 100 | 100 |

The supernatant was then transferred into the empty dialysis device prepared in as set out above. After closing the lid of the microcentrifuge tube over the dialysis device, incubations were carried out at 30° C. for 6 hours. As an alternative, other dialysis devices that have pore size varying from 3 kDa to 20 kDa have also been successfully used including PIERCE™ 96-well Microdialysis Plate, (THERMO FISHER SCIENTIFIC®, Cat. No. 88260), Thermo Fisher Rapid Equilibrium Dialysis devices (THERMO FISHER SCIENTIFIC®, Cat. No. 91012) as well as Thermo Fisher Slide-A-Lyzer™ MINI devices or Thermo Fisher Slide-A-Lyzer™ G2 Dialysis Cassettes.

The dialysis device containing reaction mixtures were shaken at approximately 800 rpm during the course of incubation using a small table-top shaker incubator such as EPPENDORF™ THERMOMIXER™. Although protein expression is complete within six hours for most proteins tested, incubating up to 16 hours may increase expression of some proteins as is typically seen with expression of green flourescent protein. Optimal time to express each protein must be determined empirically.

The products from the IVTT reactions were used as sample for western blots to analyze protein expression. Three µl of the IVTT product was mixed with 12 µl of nuclease free water and 5 µl of 4×LDS (lithium dodecyl sulfate) sample buffer (THERMO FISHER SCIENTIFIC®, Cat. No. 84788), which was premixed with 5% β-mercaptoethanol. The samples were then heated for 10 minutes at 100° C. using a heat block and were then loaded on to the NuPAGE 4-12% Bis-Tris gels (THERMO FISHER SCIENTIFIC®, Cat. No. NP0335BOX). PAGE Ruler Plus prestained protein ladder (THERMO FISHER SCIENTIFIC®, Cat No. 26619) was also loaded in the first lane of the gel along with the samples. The gels were run in the NuPAGE® MES SDS Running Buffer (THERMO FISHER SCIENTIFIC®, Cat. No. NP0002) at 120V for 5 minutes and then 170V for 1 hour. After which the gels were transferred on to a nitrocellulose membrane (THERMO FISHER SCIENTIFIC®, Cat. No. 88014) with 1-step transfer buffer (THERMO FISHER SCIENTIFIC®, Cat. No. 84731) using Pierce G2 Fast Blotter for 10 minutes (High Molecular weight program default setup). Following which the membrane was washed twice with 1×TBST (THERMO FISHER SCIENTIFIC®, Cat. No. 28360) 5 minutes each and then blocked it using Starting Block (THERMO FISHER SCIENTIFIC®, Cat. No. 37543) for 1 hour at room temperature. After blocking, the membrane was washed three times with 1×TBST for 5 minutes each at room temperature and then membrane was incubated overnight at 4° C. with 6× His epitope tag (SEQ ID NO: 3) primary antibody (THERMO FISHER SCIENTIFIC ®, Cat. No. MA1-21315) diluted in starting block at 1:2000.

The next day, membrane was again washed with 1×TBST 6 times 5 minutes each and then incubated with goat anti-mouse IgG HRP conjugated secondary antibody THERMO FISHER SCIENTIFIC®, Cat. No. 31430) diluted in starting block at 1:50,000 for 1 hour at room temperature. Finally, the membrane was washed 6 time with 1× TB ST for 5 minutes each and developed using SuperSignal West Dura Extended Duration Substrate (THERMO FISHER SCIENTIFIC®, Cat. No. 34076) for 2-3 minutes at room temperature and then observed using myECL imager. The images were captured using the imager and then band intensities were quantified using myImage analysis software.

Figure 21:
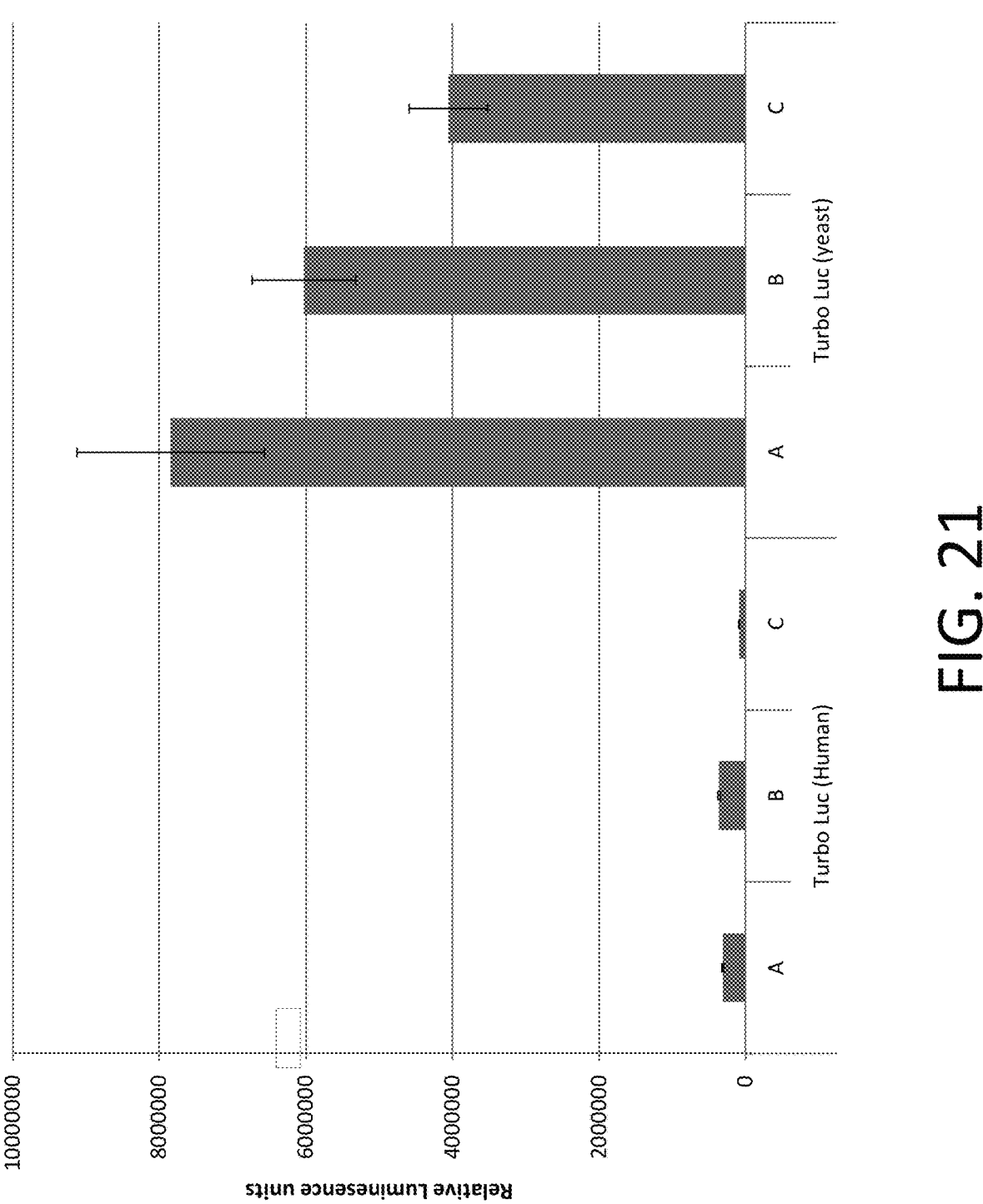
FIG. 21 shows replicated experiments for the expression of the human and yeast optimized linear DNA encoding luciferase obtained from three different lots.
Figure 22:
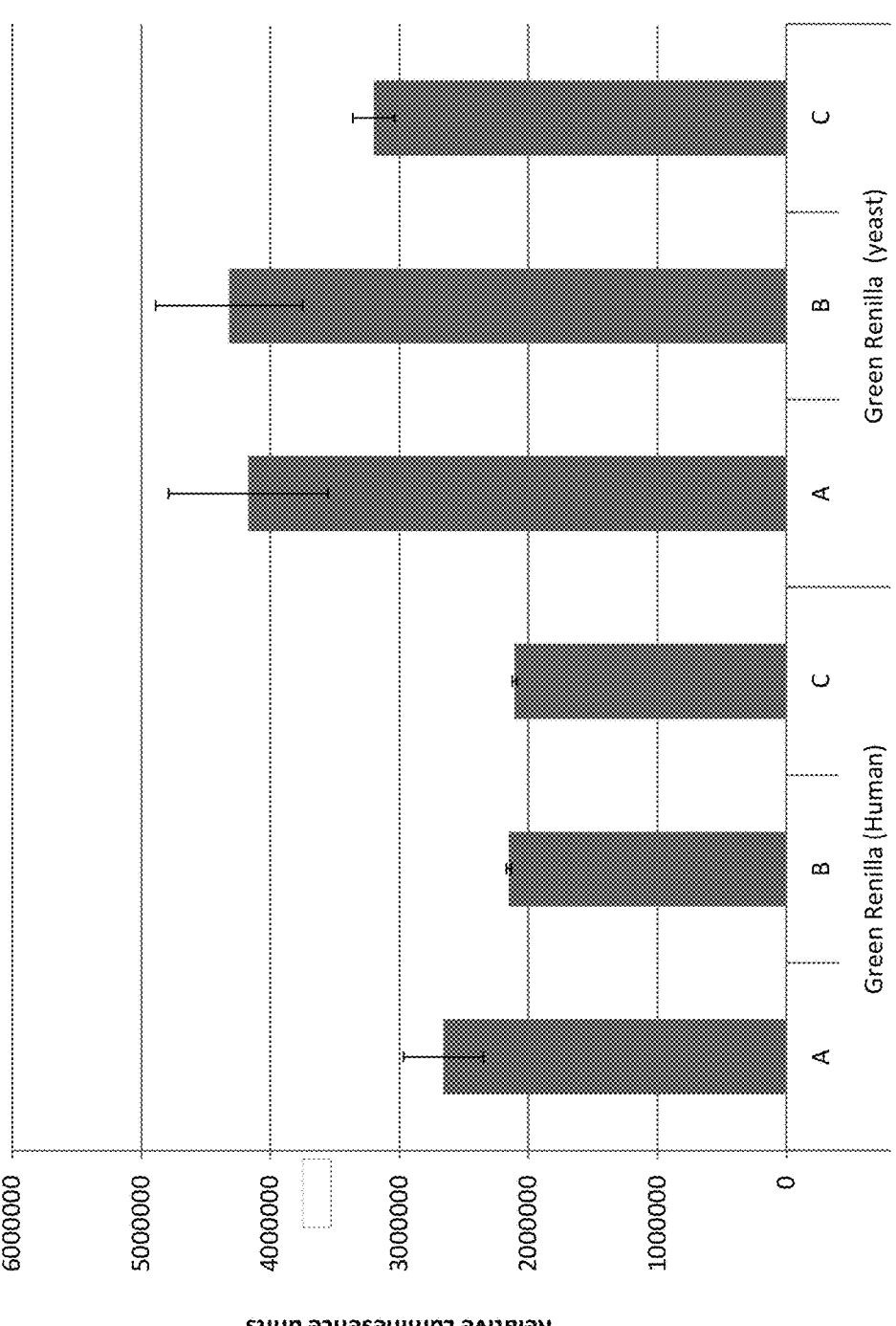
FIG. 22 shows replicated experiments for the expression of the human and yeast optimized linear DNA encoding Green *Renilla* obtained from three different lots.

Example 4: Effects of Yeast Codon Optimization on Luciferase Gene Expression in IVT1 Reactions Using Linear DNA Obtained from Three Different Lots Human in vitro translation (IVTT) reactions were set up to express the human and yeast optimized linear DNA obtained from three different lots (A, B and C) (see FIGS. 21 and 22). Similar to Example 3 above, each of the IVTT reactions contained 12.5 µl of HeLa lysate, 2.5 ul of Accessory proteins, 5 µl of Reaction Mix and respective linear DNAs. Two linear DNAs that were evaluated in these reactions included Green Renilla luciferase and Turbo luciferase (Turbo Luc) DNAs have a 6× Histidine tag sequence (SEQ ID NO: 3) appended to the C-terminal region of the gene. After incubating the reactions for 3 hours at 30° C., aliquots of samples were used to measure luciferase activity as mentioned below. First each sample was diluted 500 fold (example, 5 µl of the IVT product was taken and diluted 100 times by adding 495 µl of 1×PBS (THERMO FISHER SCIENTIFIC®, Cat. No. 28348), then 5 µl of the diluted sample was loaded in a 96 well black opaque plate (THERMO FISHER SCIENTIFIC®, Cat. No. 655077-25). The samples were further diluted 10 times by adding 45 μl of 1×PBS in each well. To obtain statistically significant values, each sample was measured in triplicates.

To prepare luciferase substrates, Turbo-Luc 1-Step substrate (50×) (from THERMO FISHER SCIENTIFIC®, Cat No. 88263 TURBOLUC™ Luciferase One-Step Glow Assay Kit) was diluted using the Turbo-Luc 1-step buffer and *Renilla* Luciferase assay substrate (100×) was diluted using *Renilla* luciferase assay buffer (from THERMO FISHER SCIENTIFIC®, Cat. No. 16166 PIERCE™ RENILLA LUCIFERASE Glow Assay Kit) to prepare fresh 2× working reagent just before use. 50 μl of the appropriate luciferase reagent was added to the samples on microwell plate using a multichannel pipette. SkanIT program contained in the VARIOSKAN™ multimode wavelength instrument was used to setup the plate layout and to record the luminometric readings for 250 ms for each sample. The average of the luminescence intensities measured was plotted with +/− standard error using bar graphs.

TABLE 12

Human Codon Usage

| | T | C | A | G |
|---|---|---|---|---|
| T | TTT F 0.45 | TCT S 0.18 | TAT Y 0.43 | TGT C 0.45 |
| | TTC F 0.55 | TCC S 0.22 | TAC Y 0.57 | TGC C 0.55 |
| | TTA L 0.07 | TCA S 0.15 | TAA * 0.28 | TGA * 0.52 |
| | TTG L 0.13 | TCG S 0.06 | TAG * 0.20 | TGG W 1.00 |
| C | CTT L 0.13 | CCT P 0.28 | CAT H 0.41 | CGT R 0.08 |
| | CTC L 0.20 | CCC P 0.33 | CAC H 0.59 | CGC R 0.19 |
| | CTA L 0.07 | CCA P 0.27 | CAA Q 0.25 | CGA R0.11 |
| | CTG L 0.41 | CCG P 0.11 | CAG Q 0.75 | CGG R 0.21 |
| A | ATT I 0.36 | ACT T 0.24 | AAT N 0.46 | AGT S 0.15 |
| | ATC I 0.48 | ACC T 0.36 | AAC N 0.54 | AGC S 0.24 |
| | ATA I 0.16 | ACA T 0.28 | AAA K 0.42 | AGA R 0.20 |
| | ATG M 1.00 | ACG T 0.12 | AAG K 0.58 | AGG R 0.20 |
| G | GTT V 0.18 | GCT A 0.26 | GAT D 0.46 | GGT G 0.16 |
| | GTC V 0.24 | GCC A 0.40 | GAC D 0.54 | GGC G 0.34 |
| | GTA V 0.11 | GCA A 0.23 | GAA E 0.42 | GGA G 0.25 |
| | GTG V 0.47 | GCG A 0.11 | GAG E 0.58 | GGG G 0.25 |

TABLE 13

*Saccharomyces cerevisiae* Codon Usage

| | T | C | A | G |
|---|---|---|---|---|
| T | TTT F 0.59 | TCT S 0.26 | TAT Y 0.56 | TGT C 0.63 |
| | TTC F 0.41 | TCC S 0.16 | TAC Y 0.44 | TGC C 0.37 |
| | TTA L 0.28 | TCA S 0.21 | TAA * 0.48 | TGA * 0.29 |
| | TTG L 0.29 | TCG S 0.10 | TAG * 0.24 | TGG W 1.00 |
| C | CTT L 0.13 | CCT P 0.31 | CAT H 0.64 | CGT R 0.15 |
| | CTC L 0.06 | CCC P 0.15 | CAC H 0.36 | CGC R 0.06 |
| | CTA L 0.14 | CCA P 0.41 | CAA Q 0.69 | CGA R 0.07 |
| | CTG L 0.11 | CCG P 0.12 | CAG Q 0.31 | CGG R 0.04 |
| A | ATT I 0.46 | ACT T 0.35 | AAT N 0.59 | AGT S 0.16 |
| | ATC I 0.26 | ACC T 0.22 | AAC N 0.41 | AGC S 0.11 |
| | ATA I 0.27 | ACA T 0.30 | AAA K 0.58 | AGA R 0.48 |
| | ATG M 1.00 | ACG T 0.13 | AAG K 0.42 | AGG R 0.21 |
| G | GTT V 0.39 | GCT A 0.38 | GAT D 0.65 | GGT G 0.47 |
| | GTC V 0.21 | GCC A 0.22 | GAC D 0.35 | GGC G 0.19 |
| | GTA V 0.21 | GCA A 0.29 | GAA E 0.71 | GGA G 0.22 |
| | GTG V 0.19 | GCG A 0.11 | GAG E 0.29 | GGG G 0.12 |

TABLE 14

*Eschericia coli* Codon Usage

| | T | C | A | G |
|---|---|---|---|---|
| T | TTT F 0.58 | TCT S 0.17 | TAT Y 0.59 | TGT C 0.46 |
| | TTC F 0.42 | TCC S 0.15 | TAC Y 0.41 | TGC C 0.54 |
| | TTA L 0.14 | TCA S 0.14 | TAA * 0.61 | TGA * 0.30 |
| | TTG L 0.13 | TCG S 0.14 | TAG * 0.09 | TGG W 1.00 |
| C | CTT L 0.12 | CCT P 0.18 | CAT H 0.57 | CGT R 0.36 |
| | CTC L 0.10 | CCC P 0.13 | CAC H 0.43 | CGC R 0.36 |
| | CTA L 0.04 | CCA P 0.20 | CAA Q 0.34 | CGA R 0.07 |
| | CTG L 0.47 | CCG P 0.49 | CAG Q 0.66 | CGG R 0.11 |
| A | ATT I 0.49 | ACT T 0.19 | AAT N 0.49 | AGT S 0.16 |
| | ATC I 0.39 | ACC T 0.40 | AAC N 0.51 | AGC S 0.25 |
| | ATA I 0.11 | ACA T 0.17 | AAA K 0.74 | AGA R 0.07 |
| | ATG M 1.00 | ACG T 0.25 | AAG K 0.26 | AGG R 0.04 |
| G | GTT V 0.28 | GCT A 0.18 | GAT D 0.63 | GGT G 0.35 |
| | GTC V 0.20 | GCC A 0.26 | GAC D 0.37 | GGC G 0.37 |
| | GTA V 0.17 | GCA A 0.23 | GAA E 0.68 | GGA G 0.13 |
| | GTG V 0.35 | GCG A 0.33 | GAG E 0.32 | GGG G 0.15 |

TABLE 15

AT/GC Content of Preferred Codons of Human, *S. cerevisiae, Pichia pastoris,* and *E. coli.*

| Amino Acid | Human | *S. cerevisiae* | *P. pastoris* | *E. coli* |
|---|---|---|---|---|
| Ala - A | GCC | GCT | GCT | GCG |
| Arg - R | CGG | AGA | AGA | CGT/CGC |
| Asn - N | AAC | AAT | AAC | AAC |
| Asp - D | GAC | GAT | GAT | GAT |
| Cys - C | TGT | TGT | TGT | TGC |
| Gln - Q | CAG | CAA | CAA | CAG |
| Glu - E | GAG | GAA | GAA | GAA |
| Gly - G | GGC | GGT | GGT | GGC |
| His - H | CAC | CAT | CAT | CAT |
| Ile - I | ATC | ATT | ATT | ATT |
| Leu - L | CTG | TTG | TTG | CTG |
| Lys - K | AAG | AAA | AAG | AAA |
| Met - M | ATG | ATG | ATG | ATG |
| Phe - F | TTC | TTT | TTT | TTT |
| Pro - P | CCC | CCA | CCA | CCG |
| Ser - S | AGC | TCT | TCT | AGC |
| Thr - T | ACC | ACT | ACT | ACC |
| Trp - W | TGG | TGG | TGG | TGG |
| Tyr - Y | TAC | TAT | TAC | TAT |
| Val - V | GTG | GTT | GTT | GTG |
| Stop | TGA | TAA | TAA | TAA |
| % CG | 63% | 30% | 37% | ~53% |
| C-G Bases | (34/60) | (19/60) | (22/60) | (31-32/60) |

TABLE 16

Preferred Codons of Human, *S. cerevisiae* and *E. coli* with a CG content of Two or Three.

| | Human | Yeast | *E. coli* |
|---|---|---|---|
| Three Bases | Ala, Arg, Gly, Pro | None | Ala, Arg, Gly, Pro |
| Two Bases | Asp, Gln, Glu, His, Leu, Ser, Thr, Trp, Val | Ala, Gly, Pro, Trp, | Gln, His, Leu, Ser, Thr, Trp, Val |

While the foregoing embodiments have been described in some detail for purposes of clarity and understanding, it will be clear to one skilled in the art from a reading of this disclosure that various changes in form and detail can be made without departing from the true scope of the embodiments disclosed herein. For example, all the techniques, apparatuses, systems and methods described above can be used in various combinations.

Exemplary Subject Matter of the Invention is Represented by the Following Clauses:

Clause 1. A method of producing a protein, the method comprising:

(a) designing a nucleic acid molecule encoding the protein, (b) generating oligonucleotides encoding subportions of the nucleic acid molecule, (c) assembling the oligonucleotides to produce a population of nucleic acid molecules encoding the protein, (d) contacting the population of nucleic acid molecules encoding the protein with a first mixture suitable for the in vitro transcription and translation of members of the population of nucleic acid molecules encoding the protein to form a second mixture, and (e) incubating the second mixture of (d) under conditions suitable for the production of (1) mRNA encoding the protein and (2) the protein, wherein the first mixture suitable for the in vitro transcription and translation of members of the population of nucleic acid molecules comprises cellular components from cells of a first organism, wherein some or all of the codons of the nucleic acid molecules encoding the protein are optimized for translation in a second organism, and wherein the first organism and the second organism are of different species.

Clause 2. The method of clause 1, wherein the population of nucleic acid molecules encoding the protein are linear.

Clause 3. The method according to clause 2, wherein the linear nucleic acid molecules comprise a promoter operable linked to the protein coding regions.

Clause 4. The method according to clause 3, wherein the population of nucleic acid molecules encoding the protein are circular nucleic acid molecules.

Clause 5. The method of clause 4, wherein the circular nucleic acid molecules are plasmids.

Clause 6. The method according to any of the preceding clauses, wherein the second mixture of (d) contains transfer RNA molecules obtained from an organism other than the first organism.

Clause 7. The method according to clauses 1 through 5, wherein the second mixture of (d) contains transfer RNA from the second organism.

Clause 8. The method according to any of the preceding clauses, wherein the second mixture of (d) contains at least one synthetically produced transfer RNA molecule.

Clause 9. The method of clause 8, wherein the synthetically produced transfer RNA molecule is produced by transcription of a DNA molecule.

Clause 10. The method according to any of the preceding clauses, wherein some or all of the codons of the nucleic acid molecule encoding the protein are optimized for translation in cells of the second organism are selected to have a GC content below 55%.

Clause 11. The method of clause 10, wherein the GC content of the coding region is in a range selected from the group consisting of:

(a) from 30% to 54%, (b) from 35% to 54%, (c) from 35% to 50%, (d) from 40% to 54%, (e) from 40% to 50%, (f) from 30% to 45%, and (g) from 35% to 54%.

Clause 12. The method according to any of the preceding clauses, wherein the second organism is *Saccharomyces cerevisiae*.

Clause 13. The method according to any of the preceding clauses, wherein at least half of the population of nucleic acid molecules encoding are the most preferred codons *Saccharomyces cerevisiae*.

Clause 14. The method according to any of the preceding clauses, wherein, for at least 75% of proteins, expression of nucleic acid molecules containing codons for preferred codons of the first organism results in the production of less protein than expression of nucleic acid molecules containing codons for preferred codons of the second organism.

Clause 15. The method according to any of the preceding clauses, wherein expression of nucleic acid molecules containing codons for preferred codons of the first organism results in the production of less protein than expression of nucleic acid molecules containing codons for preferred codons of the second organism and wherein the difference in protein production averages greater than 10%.

Clause 16. The method according to any of the preceding clauses, wherein transfer RNA molecules are exogenously added to the first mixture suitable for the in vitro transcription and translation.

Clause 17. The method of clause 16, wherein the first mixture suitable for the in vitro transcription and translation is obtained from a mammalian cell.

Clause 18. The method of clause 17, wherein the cell is a yeast cell.

Clause 19. The method of clause 18, wherein the yeast cell is *Saccharomyces cerevisiae*.

Clause 20. The method of clause 16, wherein the first mixture suitable for the in vitro transcription and translation comprises exogenously added transfer RNA molecules are obtained from a fungal cell.

Clause 21. A method of producing a protein, the method comprising:

(a) assembling the oligonucleotides to produce a population of nucleic acid molecules encoding the protein, (b) contacting the population of nucleic acid molecules encoding the protein with a first mixture suitable for the in vitro transcription and translation of members of the population of nucleic acid molecules encoding the protein to form a second mixture, and (c) incubating the second mixture of (d) under conditions suitable for the production of (1) mRNA encoding the protein and (2) the protein, wherein (i) the first mixture suitable for the in vitro transcription and translation of members of the population of nucleic acid molecules comprises cellular components from cells of a first organism and/or (ii) some or all of the codons of the nucleic acid molecules encoding the protein are optimized for translation in a second organism, and wherein the first organism and the second organism are of different species.

Clause 22. A method of producing a protein, the method comprising:

(a) contacting a nucleic acid molecule encoding the protein with a first mixture suitable for the in vitro transcription and translation to form a second mixture, and (b) incubating the second mixture of (a) under conditions suitable the production of (1) mRNA encoding the protein and (2) the protein, wherein the first mixture suitable for the in vitro transcription and translation comprises cellular components from cells of a first organism, wherein some or all of the codons of the nucleic acid molecule encoding the protein are optimized for translation in cells of a second organism that is different than the organism from which the in vitro transcription and translation mixture is derived from, wherein transfer RNA molecules derived from the second organism are included in the second mixture during step (b), and wherein the first organism and the second organism are of different species.

Clause 23. The method of clause 22, wherein the second organism is a fungus.

Clause 24. The method according to clause 23, wherein the fungus is a yeast.

Clause 25. The method of clause 24, wherein the yeast is *Saccharomyces cerevisiae*.

Clause 26. The method according to any of the preceding clauses, wherein the GC content of the coding region is in a range selected from the group consisting of:

(a) from 30% to 54%, (b) from 35% to 54%, (c) from 35% to 50%, (d) from 40% to 54%, (e) from 40% to 50%, (f) from 30% to 45%, and (g) from 35% to 54%.

Clause 27. A reaction mixture comprising:

(a) a cell extract obtained from mammalian cells, (b) a nucleic acid molecule encoding a protein, wherein at least half of the codons encoding the protein are not preferred codons of the mammalian cells, and (c) transfer RNA molecules obtained from non-mammalian cells;

wherein the average GC content of the codons encoding the protein is less than 50%.

Clause 28. The reaction mixture of clause 27, wherein the mammalian cell is a human cell.

Clause 29. The reaction mixture of clause 28, wherein the human cell is a HeLa cell.

Clause 30. The reaction mixture according to clause 27 to 29, wherein the population of nucleic acid molecules encoding the protein are linear.

Clause 31. The reaction mixture of clause 30, wherein the linear nucleic acid molecules comprise a promoter operable linked to the protein coding regions.

Clause 32. The reaction mixture according clause 27 to 31, wherein mammalian cells is a mouse cell.

Clause 33. The reaction mixture according to clause 27 to 32, wherein the non-mammalian cells is a yeast cell.

Clause 34. A mechanical device comprising:

(a) a control device capable of performing the following functions:

(1) accepting the input of nucleotide or amino acid sequence data, (2) designing nucleic acid molecules corresponding to the input nucleotide sequence or encoding the amino acid sequence, (3) directing reagent flows and incubation times for the synthesis and assembly of nucleic acid molecules designed in (2), and (4) directing reagent flows and incubation times for the in vitro transcription and translation of nucleic acid molecules synthesized by the device using the reagent flows and incubation times for directed in (3), (b) one or more reagent storage reservoirs, (c) one or more reaction sites for the synthesis and assembly of nucleic acid molecules and the in vitro transcription and translation of nucleic acid molecules to produce proteins, (d) one or more ports for the removal of a nucleic acid molecules and/or proteins produced by the device, and (e) optionally, one or more means for detecting and/or purifying and/or quantifying the proteins produced by the device.

Clause 35. The device of clause 34, wherein the control device is further capable of directing reagent flows and incubation times for one or more error correction and/or selection processes.

Clause 36. The device according to clause 34 to 35, further comprising a waste reservoir for the storage of reagents that have been removed from one or more reaction site.

Clause 37. The device according to any of the preceding clauses, wherein one or more reagent reservoirs contain one or more reagent selected from the group consisting of:

(a) a washing solution, (b) a mis-match repair endonuclease, (c) a cellular extract suitable for in vitro transcription and/or in vitro translation, and (d) one or more nucleoside phosphoramidite.

Clause 38. A method for the production of a protein using a mechanical device, the method comprising entry of the amino acid sequence of the protein into the mechanical device, wherein the mechanical device:

(a) designs of a nucleic acid molecule encoding the amino acid sequence, (b) generates the nucleic acid molecule encoding the amino acid sequence, and (c) performs in vitro transcription and translation reactions using the nucleic acid molecule generated in step (b).

Clause 39. A device for performing the method of clause 38.

Clause 40. A method for identifying a nucleic acid molecule encoding a protein of interest, the method comprising:

(a) generating an array of nucleic acid molecules in an expressible format, (b) performing in vitro transcription and translation on a plurality of the arrayed nucleic acid molecules to produce proteins encoded by the nucleic acid molecules, (c) screening the proteins produced in step (b) to identify one or more proteins of interest, and (d) identifying one or more nucleic acid molecules encoding one or more of the one or more proteins of interest.

Clause 41. The method of clause 40, wherein each locus of the array is designed to encode nucleic acid molecules having the same amino acid sequence.

Clause 42. The method of clause 40, wherein the array is designed to encode a plurality of nucleic acid molecules comprising a library.

Clause 43. The method of clause 42, wherein the library is a cDNA library.

Clause 44. The method of clause 40, wherein the array is designed to contain nucleic acid molecules encoding a plurality of variants of one or more proteins.

Clause 45. The method of clause 44, wherein the variants of one or more proteins are designed to differ in amino acid sequence at one or more locations.

Clause 46. The method of clause 45, wherein the variants of one or more proteins are designed to contain different amino acids at a single location.

Clause 47. The method of clause 40, wherein the variants of one or more proteins are designed to contain different amino acids at two or more locations.

Clause 48. The method of any one of clauses 44 to 47, wherein an amino acid that naturally occurs at one or more loci of the variants of one or more proteins is designed to be replaced with an amino acid that does not naturally occur at the one or more loci.

Clause 49. The method of any one of clauses 40 to 48, further comprising isolating one or more nucleic molecules encoding at least one of the one or more proteins of interest.

Clause 50. The method of clause 49, wherein the one or more nucleic molecules are attached to solid supports located in wells of a multiwell plate.

Clause 51. The method of any one of clauses 40 to 50, wherein the GC content of the coding regions of one or more the nucleic acid molecules of (a) are in a range selected from the group consisting of:

(a) from 30% to 54%, (b) from 35% to 54%, (c) from 35% to 50%, (d) from 40% to 54%, (e) from 40% to 50%, (f) from 30% to 45%, and (g) from 35% to 54%.

Clause 52. The method of any one of clauses 40 to 51, wherein in vitro transcription and translation is performed using a reaction mixture comprising (a) a cell extract obtained from mammalian cells, (b) a nucleic acid molecule encoding a protein, wherein at least half of the codons encoding the protein are not preferred codons of the mammalian cells, and (c) transfer RNA molecules obtained from non-mammalian cells;

wherein the average GC content of the codons of one or more of the nucleic acid molecules encoding the one or more proteins of interest is less than 50%.

Clause 53. A method for identifying a nucleic acid molecule encoding a protein of interest, the method comprising:

(a) generating an array of nucleic acid molecules in an expressible format, (b) performing in vitro transcription and translation on a plurality of the arrayed nucleic acid molecules to produce proteins encoded by the nucleic acid molecules, (c) screening the proteins produced in step (b) to identify one or more protein of interest, (d) identifying one or more nucleic acid molecules encoding the proteins of interest, and (e) isolating one or more of the one or more nucleic acid molecules encoding the proteins of interest identified in (d).

Clause 54. The method of clause 53, wherein isolation of the one or more of the one or more nucleic acid molecules encoding the proteins of interest is mediated by cleavage of the nucleic acid molecules from a surface of a well of a multiwell plate.

Clause 55. The method of clause 53, wherein isolation of the one or more of the one or more nucleic acid molecules encoding the proteins of interest is mediated by the removal of one or more beads from a well of a multiwell plate.

Clause 56. The method of clause 54, wherein removal of the one or more beads from a well of a multiwell plate is mediated by a mechanical device.

Clause 57. The method of clause 56, wherein the mechanical device is a suction device or tweezers.

Clause 58. The method of clause 55, wherein removal of the one or more beads from a well of a multiwell plate occurs by lifting of the beads with a gas bubble.

Clause 59. The method of clause 58, wherein the gas bubble is generated by an electrical current in the well.

Clause 60. The method of clause 50 or 58, wherein the beads are lifted from the well into a flow stream.

Clause 61. The method of any one of clauses 55 to 60, wherein the beads are transported to one or more locations where nucleic acid molecules are released from the beads.

Clause 62. The method of any one of clauses 53 to 61, wherein the one or more nucleic acid molecules are linked to one or more other nucleic acid molecules.

Clause 63. The method of clause 62, wherein at least one of the one or more other nucleic acid molecules has an origin of replication.

Clause 64. The method of clause 62 or 63, wherein at least one of the one or more other nucleic acid molecules is a plasmid.

---

What is claimed is:

1. A method of producing a protein, the method comprising:

a) designing a codon optimized nucleic acid molecule, wherein the codon optimized nucleic acid molecule encodes a mammalian protein, and wherein codons of the nucleic acid molecule are optimized for translation in a yeast, (b) generating oligonucleotides encoding subportions of the codon optimized nucleic acid molecule, (c) assembling the oligonucleotides generated in (b) to produce the codon optimized nucleic acid molecule, (d) contacting the codon optimized nucleic acid molecule assembled in (c) with a coupled in vitro translation/transcription reaction mixture under conditions that result in the production of (1) mRNA encoding the protein encoded by the codon optimized nucleic acid molecule and (2) the protein encoded by the codon optimized nucleic acid molecule, wherein the codons of the nucleic acid molecule are selected to avoid inverse complementary repeats that are capable of forming secondary structures in the mRNA produced in the coupled in vitro translation/transcription reaction mixture, and wherein the reaction mixture of (d) comprises mammalian cell components.

2. The method of claim 1, wherein the codon optimized nucleic acid molecule encodes a human protein.

3. The method of claim 1, wherein the production of the mammalian protein encoded by the codon optimized nucleic acid molecule optimized for translation in a yeast provides at least 20% higher yield of the mammalian protein than if the codon optimized nucleic acid molecule is optimized for translation in a mammal.

4. The method of claim 1, wherein the production of the mammalian protein encoded by the codon optimized nucleic acid molecule optimized for translation in a yeast provides 10% to 40% higher yield of the mammalian protein than if the codon optimized nucleic acid molecule is optimized for translation in a mammal.

5. The method of claim 1, wherein the codon optimized nucleic acid molecule has an average GC content of from 35% to 50%.

6. The method of claim 1, wherein the codon optimized nucleic acid molecule is linear.

7. The method of claim 6, wherein the linear codon optimized nucleic acid molecule comprises a promoter operably linked to the codon optimized nucleic acid molecule.

8. The method of claim 1, wherein the reaction mixture of (d) contains exogenously added transfer RNA molecules.

9. The method of claim 8, wherein the exogenously added transfer RNA molecules are from yeast.

10. The method of claim 1, wherein the yeast is *Saccharomyces cerevisiae*.

11. The method of claim 1, wherein at least half of the codon optimized nucleic acid molecule population is codon optimized for *Saccharomyces cerevisiae*.

* * * * *